United States Patent [19]

Uehara et al.

[11] Patent Number: 5,609,561

[45] Date of Patent: Mar. 11, 1997

[54] ELECTRONIC TYPE ENDOSCOPE IN WHICH IMAGE PICKUP UNIT IS DISMOUNTED TO EXECUTE DISINFECTION/STERILIZATION PROCESSING

[75] Inventors: Masao Uehara; Katsuyuki Saito, both of Hachioji; Masahito Goto, Oi-machi; Shinji Yamashita, Hachioji; Akinobu Uchikubo, Ome; Akihiro Miyashita, Hachioji; Takehiro Nakagawa, Hachioji; Kazunari Kobayashi, Hachioji; Akira Murata, Hino; Mototsugu Ogawa; Seiji Yamaguchi, both of Hachioji, all of Japan

[73] Assignee: Olympus Optical Co., Ltd, Tokyo, Japan

[21] Appl. No.: 362,731

[22] Filed: Dec. 22, 1994

Related U.S. Application Data

[63] Continuation of Ser. No. 936,015, Aug. 27, 1992, abandoned.

[30] Foreign Application Priority Data

| Jun. 9, 1992 | [JP] | Japan | 4-149705 |
| Jun. 10, 1992 | [JP] | Japan | 4-150927 |
| Jun. 10, 1992 | [JP] | Japan | 4-150928 |
| Jun. 10, 1992 | [JP] | Japan | 4-150930 |

[51] Int. Cl.$^6$ ........................ A61B 1/04
[52] U.S. Cl. .............. 600/112; 600/132; 600/133; 348/75
[58] Field of Search ................ 600/109, 112, 600/130, 133, 160, 132; 348/73, 75

[56] References Cited

U.S. PATENT DOCUMENTS

| 4,545,369 | 10/1985 | Sato . | |
| 4,756,304 | 7/1988 | Watanabe | 128/6 |
| 4,777,524 | 10/1988 | Nakajima et al. | 358/98 |
| 4,779,130 | 10/1988 | Yabe | 358/98 |
| 4,779,613 | 10/1988 | Hashiguchi et al. | 128/6 |
| 4,839,723 | 6/1989 | Yoshinaga et al. | 358/98 |
| 4,905,082 | 2/1990 | Nishigaki et al. | 358/98 |
| 4,914,521 | 4/1990 | Adair | 128/6 X |
| 4,918,521 | 4/1990 | Yabe et al. | 358/98 |
| 4,998,182 | 3/1991 | Krauter et al. | 128/6 X |
| 5,051,824 | 9/1991 | Nishigaki | 358/98 |
| 5,096,292 | 3/1992 | Sakamoto et al. | 128/6 X |
| 5,125,394 | 6/1992 | Chateneuer et al. | 128/4 |

*Primary Examiner*—Richard J. Apley
*Assistant Examiner*—John P. Leubecker
*Attorney, Agent, or Firm*—Armstrong, Westerman, Hattori, McLeland & Naughton

[57] ABSTRACT

An image pickup unit provided with an image pickup element is of structure capable of being detachably received in an endoscope body or a TV camera. After having been used in observation, the image pickup unit is dismounted, whereby disinfection processing and sterilization processing of the endoscope body from which the image pickup unit is dismounted, or the TV camera can be executed without inviting deterioration and the like of a characteristic of the image pickup unit by a disinfection unit, a sterilization unit or the like.

16 Claims, 39 Drawing Sheets

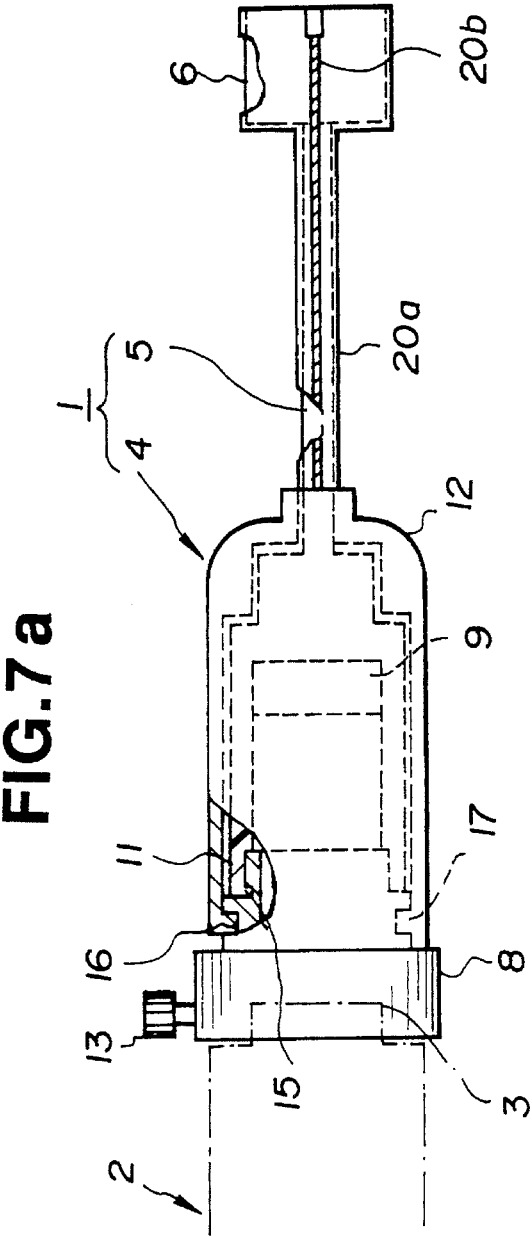
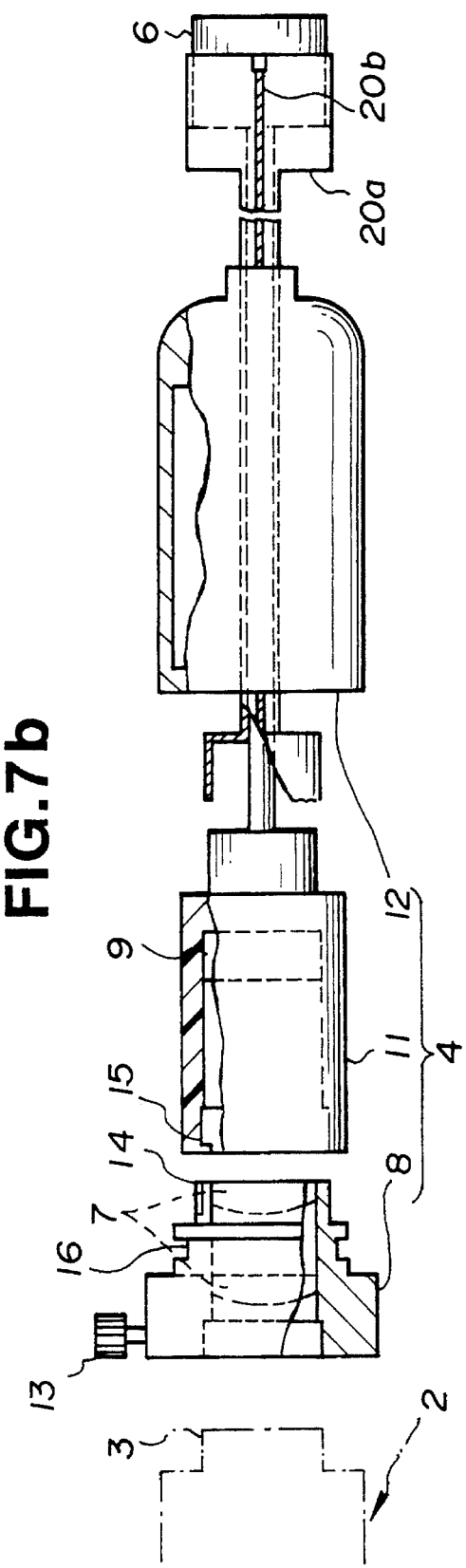

18a  19  18b 18a  19  18b

| KIND | SETTING CONTENT | | | |
|---|---|---|---|---|
| 1. ELECTRONIC ENDOSCOPE | 80° | 90% | 1.2 atms | 120 MINUTES |
| 2. OCULAR CAMERA | 80° | 90% | 1.3 atms | 100 MINUTES |
| 3. WATERPROOF ENDOSCOPE | 150° | 100% | 1.5 atms | 15 MINUTES |
| 4. TREATMENT TOOL | 200° | 100% | 1.5 atms | 10 MINUTES |
| 5. OTHERS | | | | |

PROCESSING TEMPERATURE
Ta > Tb

PROCESSING TIME
ta < tb

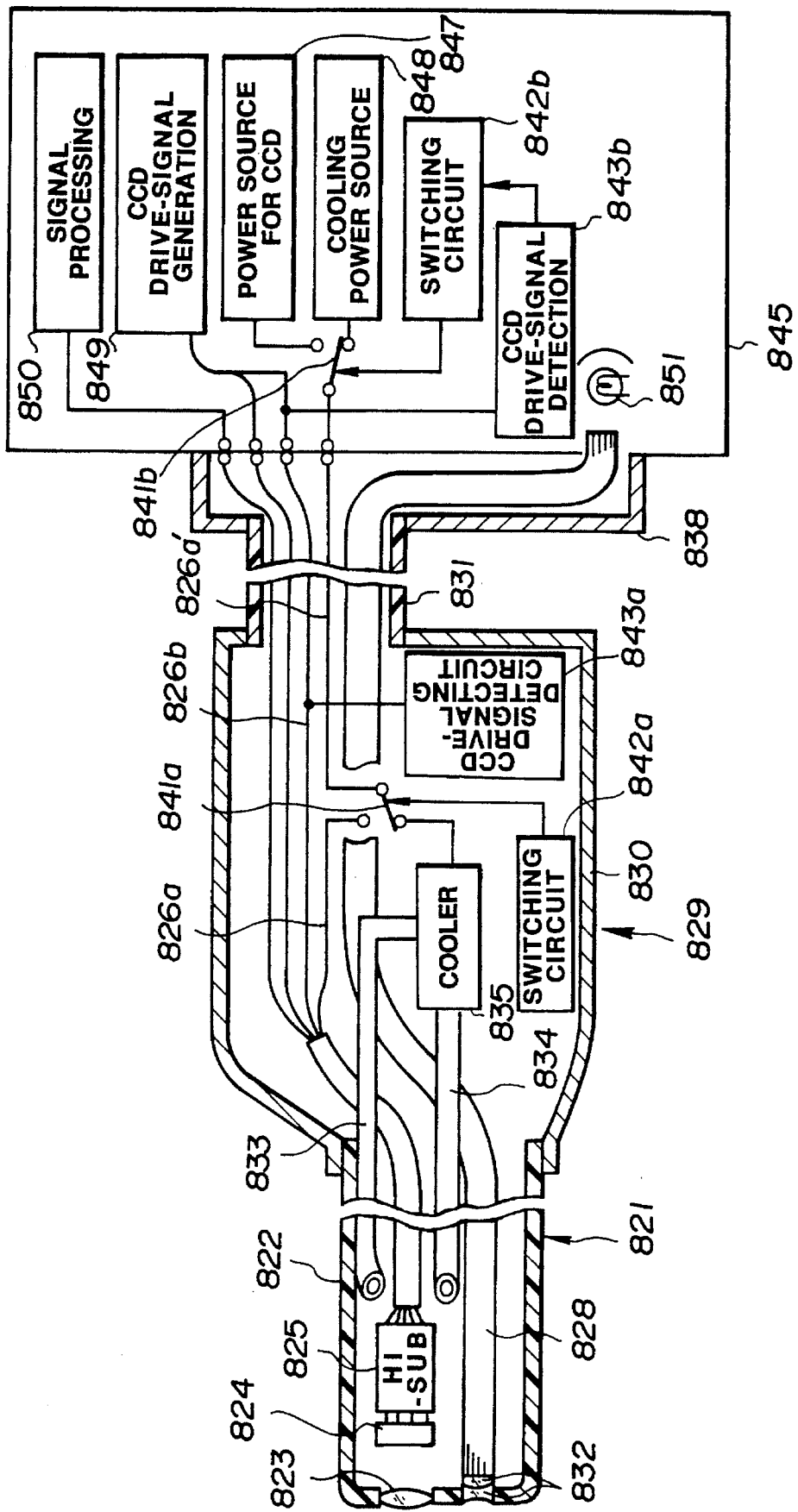

ELECTRONIC TYPE ENDOSCOPE IN WHICH IMAGE PICKUP UNIT IS DISMOUNTED TO EXECUTE DISINFECTION/STERILIZATION PROCESSING

This application is a continuation of application Ser. No. 07/936,015 filed Aug. 27, 1992, now abandoned.

BACKGROUND OF THE INVENTION

1. Field of the Invention

The present invention relates to an electronic type endoscope having a dismounting mechanism for an image pickup unit including an image pickup element in which the image pickup unit is dismounted to execute disinfection/sterilization processing or treatment.

2. Description of the Related Art and Prior Art Statement

In recent years, endoscopes have been widely utilized in a field of medical processing art. Particularly, a medical processing instrument inserted into an organism, such as an endoscope or the like, is used which is sufficiently disinfected or sterilized such that an infection condition or the like does not occur. Further, after such a medical processing instrument has been used, a body fluid within an organism, solid matter and the like are adhered to the medical processing instrument. Accordingly, after the medical processing instrument has been cleaned to remove the adhered fluid and matter, the medical processing instrument is dipped in disinfection liquid and is disinfected.

In a case where a harmful material is used for sterilization processing, or for disinfection or sterilization by sterilization gas such as EOG or the like, the harmful material must be treated or processed after the sterilization processing. Accordingly, in recent years, it has been desirable to execute sterilization processing by using a reduced amount or quantity of such poisonous material or by the use of harmless steam without the use of a poisonous material.

An electronic type endoscope using a solid-state image pickup element as image pickup means, that is, an electronic endoscope and an outside mounted camera mounted on an optical endoscope, cannot withstand thermal sterilization processing apparatus using steam normally exceeding 100° C., that is, autoclave processing, because of the characteristic of the solid-state image pickup element. On the other hand, a rigid endoscope belonging to an optical endoscope and having a hard inserting section has a resistance to the autoclave processing.

In this manner, there are endoscopes different from each other in resistance to disinfection and sterilization processing. A disinfection/sterilization unit for executing disinfection and sterilization processing at a hospital or the like is also used with conditions of disinfection and sterilization processing set, depending upon the used endoscopes. Furthermore, there may also be a case where a disinfection/sterilization unit is so used as to be capable of executing disinfection or sterilization processing with respect to existing endoscopes, or the existing endoscopes are in a disinfection/sterilization unit or disinfection/sterilization conditions in which more resistance is required.

An electronic endoscope provided with an image pickup element, or an outside mounted camera, has a low resistance to high temperatures when not protected by a heat-resisting or heat proof structure or the like. The electronic endoscope or the camera also have low resistance to humidity as well as to temperature. Accordingly, in a case where the electronic endoscope or the camera is disinfected or sterilized, it is required that the disinfection or sterilization processing is executed under a condition that the characteristic of the image pickup element is not deteriorated, or is not thermally destroyed. In this case, deterioration in the characteristic of the image pickup element due to disinfection or sterilization is high in probability whenever the deterioration is caused by repeated disinfection or sterilization processing, and there may be a case where recognizable deterioration does not occur for only one disinfection or sterilization processing cycle. For this reason, there may occur the following case. That is, disinfection or sterilization processing is repeatedly executed while the conditions of the disinfection or sterilization processing produce an environment suitable for another type endoscope having a higher resistance, without taking into account the fact that the conditions of disinfection or sterilization processing are set to an environment suited for the lower resistance of an electronic endoscope or an outside mounted camera. Thus, deterioration of the characteristic would occur.

Specifically, in a case where an electronic endoscope or an outside mounted camera is disinfected or sterilized, disinfection or sterilization processing must be executed carefully more than with other more resistant types of endoscopes. However, the electronic endoscope or the outside mounted camera is typically disinfected or sterilized without sufficient attention being paid to a resistance thereof. Thus, there may be a case where the characteristic of an expensive electronic endoscope or outside mounted camera deteriorates or fails completely.

SUMMARY OF THE INVENTION

It is an object of the invention to provide an electronic type endoscope having flexibility and provided with a mechanism capable of coping with various disinfection or sterilization processings.

It is another object of the invention to provide an electronic type endoscope capable of executing disinfection or sterilization processing in accordance with a resistance of the remaining ones of elements from which an image pickup element is dismounted.

According to the invention, there is provided an electronic type endoscope comprising:

an endoscope body having an elongated inserting section;

illuminating-light projection means for projecting an illuminating light from a distal end portion of the inserting section;

an objective optical system provided at the forward end portion of the inserting section for imaging a subject illuminated by the illuminating light;

an image pickup unit provided with an image pickup element for photoelectrically transferring an optical image based on the objective optical system, to generate an image pickup signal;

a pickup unit receiving body which receives and fully encloses the image pickup unit including a first detaching means for detachably mounting the pickup unit receiving body on the endoscope body; and a second detaching means for detaching the image pickup unit from the pickup unit receiving body, said second detaching means being located on at least one of the endoscope body and the pickup unit receiving body.

When the endoscope is used in an organism, the image pickup unit is maintained in a manner preventing contamination. After the use, the image pickup unit is released from the unit receiving element, so that elements other than the image pickup unit can be processed in disinfection and sterilization.

According to the present invention, there is also provided a TV camera comprising:

a housing element having a mount mechanism capable of being detachably mounted on an ocular portion of an optical endoscope having an observing optical system and an illuminating optical system at an elongated inserting section;

an image pickup unit received within the housing element and provided with an image pickup element photoelectrically transferring an optical image to generate an image signal; and a detachable mechanism mountable at a location opposite to the ocular portion within the housing element, and arranged such that the image pickup unit is releasable to the outside of the housing element.

With the above arrangement of the invention, the image pickup unit is dismounted so that the remaining elements can be processed in disinfection and sterilization.

BRIEF DESCRIPTION OF THE DRAWINGS

FIG. 2 is a cross-sectional view showing the outside mounted camera with an image pickup unit removed;

FIG. 3 is a view showing an aspect in which the outside mounted camera from which the image pickup unit is dismounted is received in an autoclave unit;

FIG. 4 is a view showing an aspect in which the outside mounted camera from which an image pickup unit is dismounted is received in an EOG sterilization unit together with the endoscope;

FIGS. 7a through 9 show a second embodiment of the invention, FIG. 7a being a view showing an outside mounted camera in accordance with the second embodiment, while FIG. 7b is a side elevational view showing FIG. 7a in decomposition or resolution;

FIG. 9 is a view showing an aspect in which reception is made in an autoclave unit to execute sterilization processing;

FIG. 13 is a cross-sectional view showing a structure of a forward end portion of the electronic scope;

FIG. 14 is a cross-sectional view showing a condition under which an image pickup unit is dismounted from FIG. 13;

FIG. 17 is a cross-sectional view showing a structure of a forward end portion of an electronic scope;

FIG. 18 is a cross-sectional view showing a condition on the way that an image pickup unit is dismounted from FIG. 17;

FIG. 20 is a cross-sectional view showing a condition under which the image pickup unit is mounted;

FIGS. 21 through 22b are views showing a sixth embodiment of the invention, FIG. 21 being a side elevational view showing the entirety of an electronic scope in accordance with the sixth embodiment of the invention;

FIGS. 22a and 22b are cross-sectional views showing a condition under which an image pickup unit is mounted and a condition under which the image pickup unit is dismounted;

FIG. 33 is a view showing a switch panel;

FIG. 37 is a view for explanation, showing contents of a menu when executing autoclave processing;

FIG. 38 is a flow chart showing contents of the autoclave processing;

FIG. 63 is an arrangement view showing an electronic scope in accordance with a modification of FIG. 62;

DETAILED DESCRIPTION OF THE PREFERRED EMBODIMENTS

Various embodiments of the invention will hereunder be described with reference to the accompanying drawings.

Figure 1:
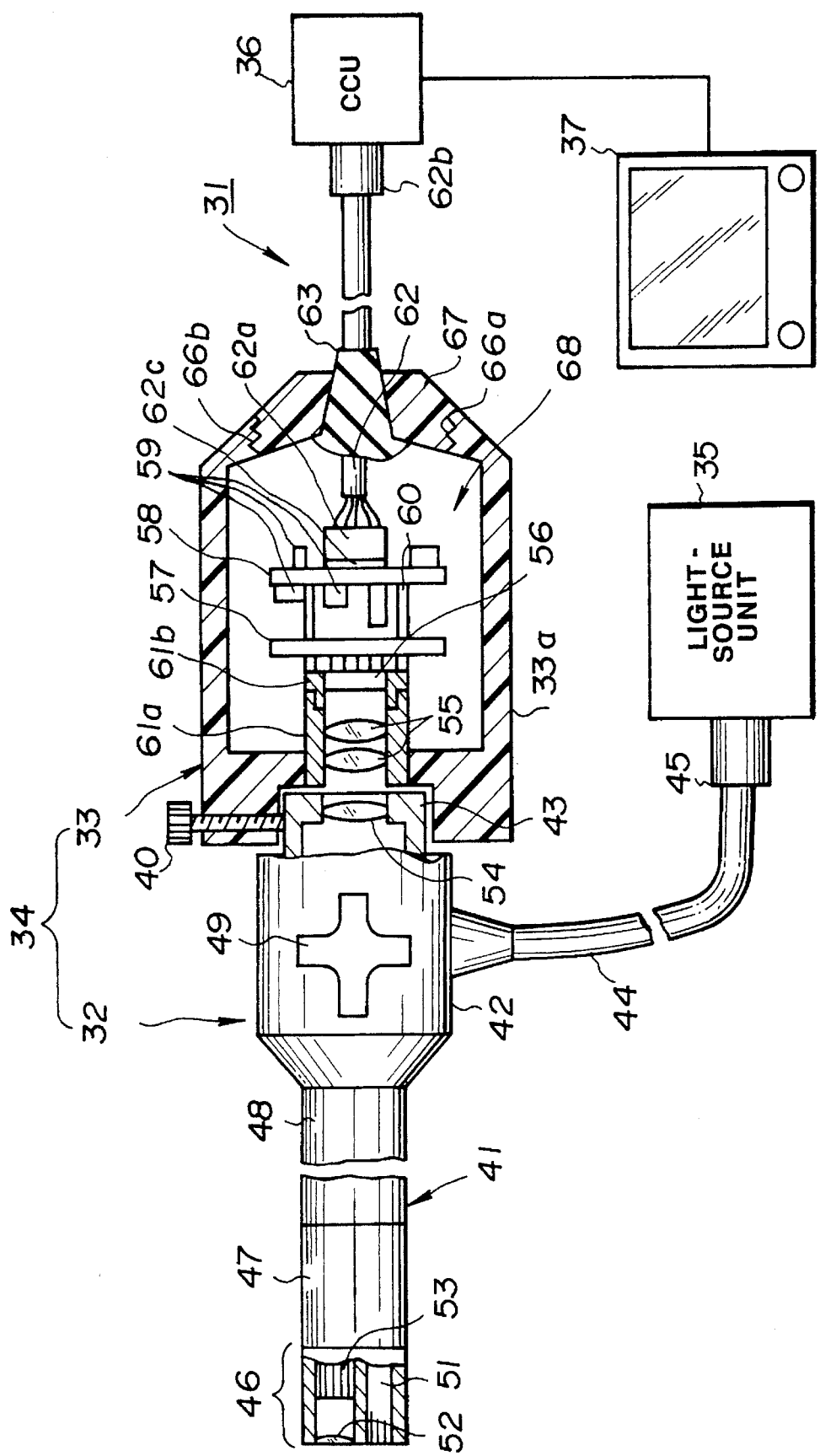
FIGS. 1 through 4 show a first embodiment of the invention, FIG. 1 being an arrangement view showing an endoscope system provided with an endoscope of camera outside mounted type, according to the first embodiment.

FIG. 1 shows an endoscope system 31 provided with an electronic type endoscope (having image pickup means) in accordance with a first embodiment of the invention.

The endoscope system 31 comprises an endoscope 34 with an outside mounted camera, serving as an electronic endoscope in accordance with the first embodiment of the invention having a flexible endoscope (referred also to as a "fiber scope") 32 and an outside mounted camera 33 mounted on the fiber scope 32, a light-source unit 35 for supplying an illuminating light to the fiber scope 32, a camera control unit (simply referred to as a "CCU") 36 for executing signal processing with respect to the outside mounted camera 33, and a monitor 37 for displaying an image signal outputted from the CCU 36.

The fiber scope 32 has an elongated flexible inserting section 41, an operating section 42 large in diameter connected to a rearward end of the inserting section 41, an ocular section 43 formed at a rearward end of the inserting section 42, and a light guide cable 44 extending from a side of the operating section 42. A connector 45 provided at a proximal end of the light guide cable 44 can detachably be connected to the light-source unit 35. The fiber scope 32 is made of, for example, a material capable of processing in sterilization within EOG (ethylene oxide gas).

The inserting section 41 has, from its forward end side, a rigid forward end portion 46, a curving portion 47 capable of being curved, and a flexible tube portion 48 having flexibility. A curving knob 49 provided at the operating section 42 is operated whereby the curving section 47 can be curved.

The connector 45 of the light guide cable 44 is connected to the light-source unit 35, whereby a white light from a lamp (not shown) within the light-source unit 35 is irradiated to an end surface of a light guide 51 formed by a flexible fiber bundle. The illuminating light transmitted by the light guide 51 is projected forwardly from an illuminating window whose end surface is mounted adjacent to the forward end portion 46, and illuminates a subject (not shown).

An optical image of the subject illuminated by the illuminating light projected forwardly from the illuminating window is imaged to a forward end surface of an image guide 53 fixedly mounted on a focus surface of an objective lens 52, by the objective lens 52 which is mounted on the observation window provided on the forward end portion 46. The image guide 53 is formed by a flexible fiber bundle. The optical image is transmitted to an end surface adjacent to the ocular portion 43, and can be observed in enlargement through an ocular lens 54 arranged in opposed relation to the end surface.

A mount mechanism in which a camera head body 33a forming the outside mounted camera 33 is capable of being detachably mounted by a pinch 40 provided with a screw or thread is formed on the ocular portion 43.

The camera head body 33a is substantially cylindrical, and a recess fitted over the ocular portion 43 is formed in one of opposite end surfaces which serves as a front surface. A tapped or thread bore is provided which extends from an outer peripheral surface adjacent to the end surface to an inner peripheral surface of the recess, and a screw of the pinch 40 is threadedly engaged with the recess. Under a condition in which the ocular portion 43 is fitted in the recess, the pinch 40 is rotatively operated whereby it is possible to mount the camera head body 33a on the ocular portion 43, or dismount the camera head body 33a from the ocular portion 43.

The camera head body 33a is formed into a cylindrical housing using a material having heat resistance capable of withstanding the thermal conditions produced from sterilization processing due to an ordinary or normal autoclave unit such as high function engineering plastic or the like, for example.

An imaging lens system 55 fixedly mounted on a frame 61a is mounted on the camera head body 33a at a location adjacent to one end surface on which the mount mechanism is formed, at a location opposite to the ocular lens 54 in a case of being mounted on the ocular portion 43. By the imaging lens system 55, imaging can be executed on a photoelectric transfer surface of a CCD 56 serving as an image pickup element. The CCD 56 is arranged such that a lead terminal is mounted or is packaged on a printed circuit board 57. Electric parts 59 such as an IC, a capacitor, a resistor and the like for operating the CCD 56 are mounted on a printed circuit board 58 arranged in parallel relation to the printed circuit board 57, to form a peripheral circuit.

The CCD 56 is fixedly mounted on a frame 61b which is provided with a click mechanism capable of being detachably mounted on a terminal end of a fitting portion which is fitted on the frame 61a on which the imaging lens system 55 is mounted. The printed circuit boards 57 and 58 are also fixedly mounted on the frame 61b through spacers 60. Further, the printed circuit board 58 is formed with a connector receptor 62c to which a connector 62a of a signal cable 62 is detachably connected. The signal cable 62 passes through a rubber-like bushing 63, and a connector 62b provided at the other end is capable of being connected to the CCU 36.

In this embodiment, the camera head body 33a has a rearward end thereof which is provided therein an opening whose size is such that an image pickup unit 68 can pass through the opening. The opening is provided with a female threaded portion 66a.

A closure or lid element 67 in the form of a ring formed with a male threaded portion 66b is threadedly engaged with the female threaded portion 66a, whereby the closure element 67 can detachably be mounted on the camera head body 33a. As shown in FIG. 1, under this mounting condition, an image pickup unit 68 housed within the camera head body 33a has a periphery thereof which is perfectly covered. Accordingly, in a case of being used for observation under this condition, it is possible to maintain or retain the image pickup unit 68 housed or received within the camera head body 33a in a clean condition.

When threaded engagement of the closure element 67 is released to disengage the closure element 67 from the camera head body 33a, it is possible to mount and dismount the image pickup unit 68 on and from the frame 61a, the image pickup unit 68 having the CCD 56 and the electronic parts 59 mounted on the printed circuit boards 57 and 58 which are mounted on the frame 61b through the spacer 60. It is possible to take out the image pickup unit 68 to the outside from the opening in the rearward end of the camera head body 33a.

Figure 2:
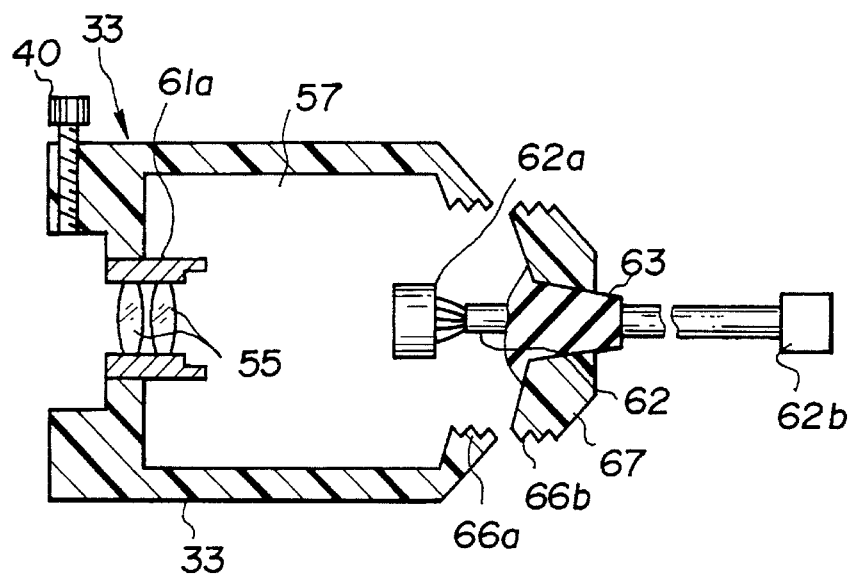
Figure 3:
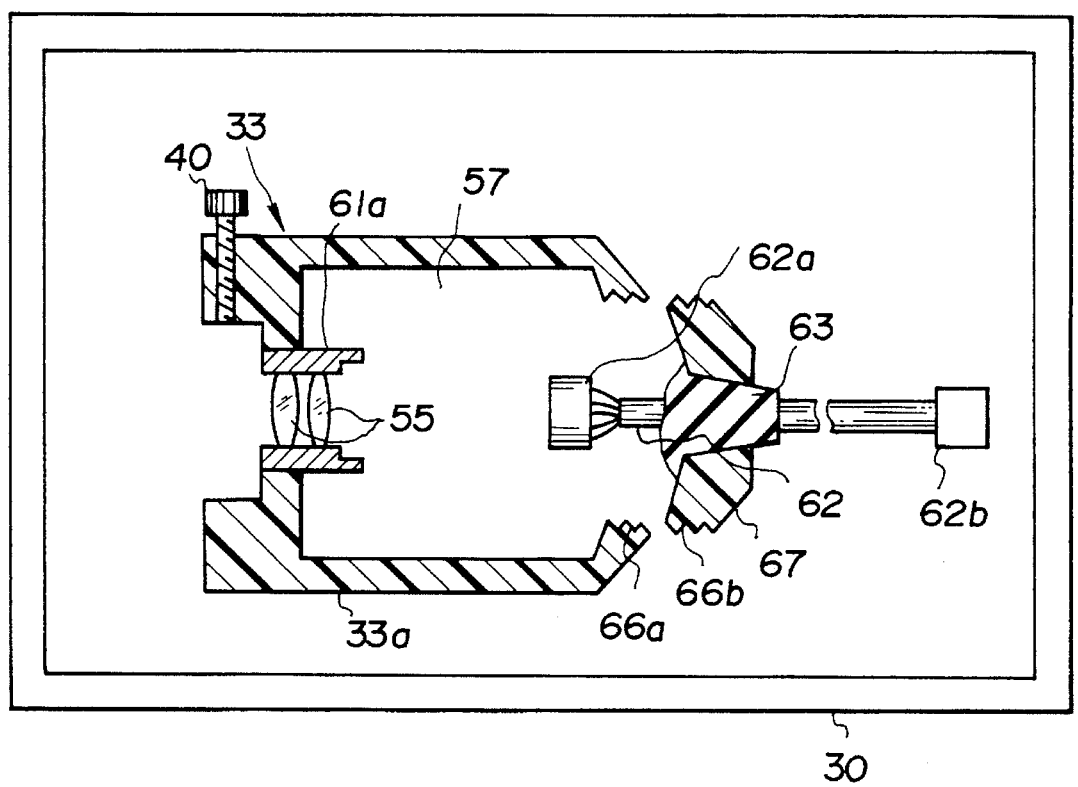
Figure 4:
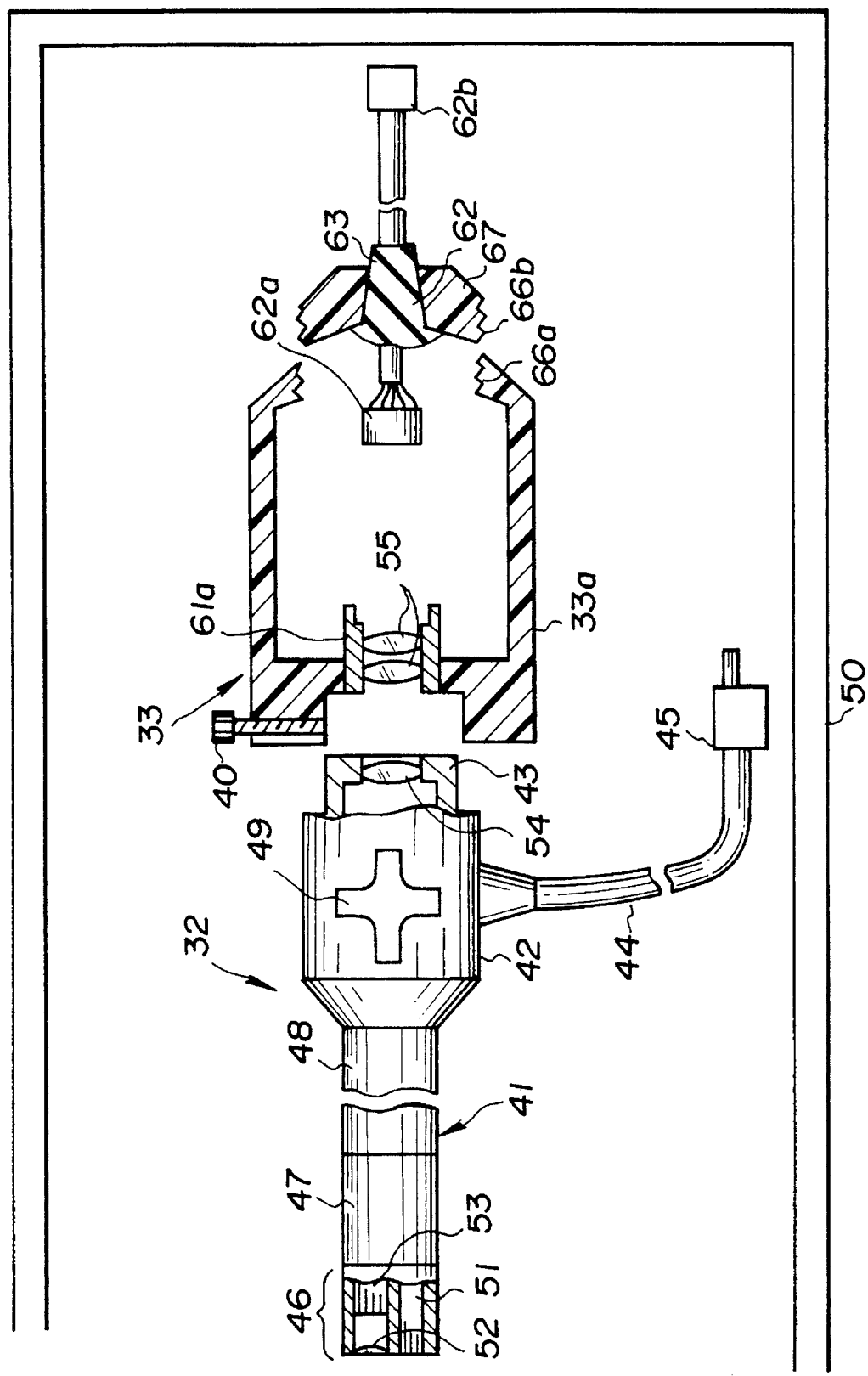

As shown in FIG. 2, it is possible to dismount the image pickup unit 68 from the outside mounted camera 33 and the cable 62. The outside mounted camera 33 and the cable 62 from which the image pickup unit 68 is dismounted are formed by a material capable of executing autoclave processing. Accordingly, as shown in FIG. 3, the outside mounted camera 33 and the cable 62 are formed by a material in which the outside mounted camera 33 and the cable 62 are received within the housing portion in the autoclave unit 30 so as to be capable of executing autoclave processing. Furthermore, the outside mounted camera 33 and the cable 62 from which the image pickup unit 68 is dismounted are formed of a material having a resistance with respect to EOG. Accordingly, as shown in FIG. 4, it is possible to receive the outside mounted camera 33 and the cable 62 from which the image pickup unit 68 is dismounted, within the receiving portion in an EOG sterilization unit 50 to execute EOG sterilization processing, together with the fiber scope 32 serving as the endoscope body.

In a case where the fiber scope 32 is also formed by a material provided with a resistance with respect to autoclave processing, it is possible to autoclave-process also the fiber scope 32 by the autoclave unit 30. (The fiber scope 32, the TV camera 33 and the cable 62 from which the image pickup unit 68 is dismounted have at least a higher resistance than the resistance of the image pickup unit 68 with respect to heat, humidity and disinfection medicine of the CCD 56.)

The CCU 36 illustrated in FIG. 1 has means for generating a drive signal for adequately driving the CCD 56, and signal processing means for converting an electric signal outputted from the CCD 56 to a standard image signal (an NTSC image signal, for example) by application of the drive signal. The image signal outputted from the CCU 36 is inputted into the monitor 37, and a subject image is displayed by the monitor 37.

According to the first embodiment of the invention, the image pickup unit 68 having the CCD 56 and the like which is received within the camera head body 33a and which has no resistance with respect to the autoclave processing can be dismounted from the camera head body 33a and can be separated therefrom. Accordingly, in a case where the first embodiment of the invention is used for observation, inspection or the like of an organism under a condition illustrated in FIG. 1, the image pickup unit 68 is maintained clean without becoming dirty because the image pickup unit 68 is received within the camera head body 33a.

After this use, the image pickup unit 68 is dismounted from the camera head body 33a. As shown in FIG. 3, the outside mounted camera 33 and the cable 62 from which the image pickup unit 68 is dismounted can be received within the autoclave unit 30 to execute autoclave processing.

By the autoclave processing, the outside mounted camera 33 and the cable 62 can again be brought to a clean condition. Accordingly, the image pickup unit 68 which is not processed in autoclave and which is maintained clean is received within the camera head body 33a, and is set as shown in FIG. 1. Thus, it is possible to use the first embodiment of the invention again for observation or the like.

Without the use of the autoclave unit 30, it is also possible that the outside mounted camera 33 and the cable 62 from which the image pickup unit 68 is dismounted are received within the receiving portion of the EOG sterilization unit 50, together with the fiber scope 32, as illustrated in FIG. 4, to execute EOG sterilization processing.

Since the first embodiment of the invention is arranged such that the image pickup unit 68 can be received and dismounted with respect to the housing of the camera head body 33a, the image pickup unit 68 can be received within the housing and can be maintained clean under the using condition. Thus, it is possible that the image pickup unit 68 is dismounted, and the outside mounted camera 33 and the cable 62 from which the image pickup unit 68 is dismounted are processed in sterilization by the autoclave unit 30, or are processed in sterilization and disinfection by other units. In this case, since it is possible to raise the resistance of the camera and cable far more than the resistance of the image pickup unit 68, it is possible to execute disinfection and sterilization under a more severe disinfection/sterilization condition than that which could be withstood when the image pickup unit 68 is mounted.

Moreover, according to the first embodiment of the invention, since it is not required to disinfect and sterilize the image pickup unit 68 by the normal or usual disinfection/sterilization unit, it is possible to secure that the characteristic of the image pickup unit 68 is not deteriorated in the manner caused by disinfection and sterilization processing by a usual disinfection/sterilization unit as in the prior art example.

According to the first embodiment of the invention, it is possible to execute disinfection and sterilization processing in accordance with a resistance of each of the remaining ones of the elements from which the image pickup unit 68 is dismounted. Generally, it is easy to raise the resistance of each of the remaining elements higher than the image pickup element, and it is possible to execute various disinfection and sterilization processings as compared with a case where the image pickup unit 68 cannot be dismounted. For this reason, it is possible to use the existing disinfection/sterilization unit, and the like, so that it is possible to widen an applied range.

Figure 5:
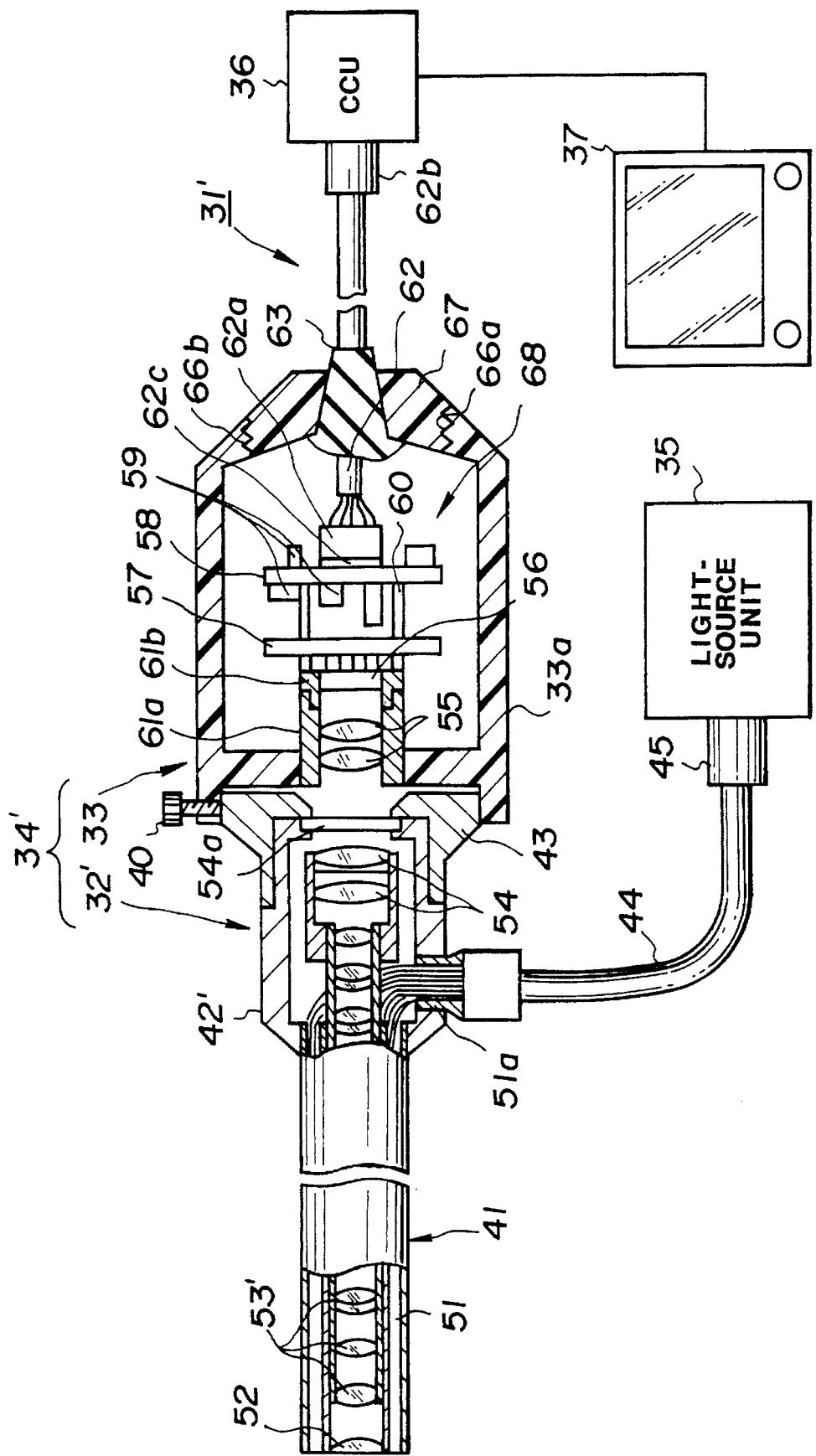
FIG. 5 is an arrangement view showing an endoscope system provided with an endoscope of camera outside mounted type in accordance with a modification of the first embodiment of the invention.

FIG. 5 shows an endoscope system 31' provided with a modification of the first embodiment of the invention. The endoscope system 31' uses a rigid endoscope 32' in place of the fiber scope 32 illustrated in FIG. 1. Specifically, the electronic endoscope in accordance with the modification comprises the rigid endoscope 32' and an outside mounted camera 33 detachably mounted on an ocular portion 43 of the rigid endoscope 32'.

The rigid endoscope 32' is arranged such that, in the fiber scope 32 illustrated in FIG. 1, an optical image of the objective lens 52 is transmitted toward the ocular portion 43 by a relay lens system 53' serving as an image guide. The relay lens system 53' transmits the optical image rearwardly by a plurality of lenses. Further, the rigid endoscope 32' has no curving section 47 and no flexible tube section 48, but an inserting section 41 is formed by a rigid pipe.

Furthermore, since the rigid endoscope 32' has no curving portion 47, a gripper 42' has no curving knob 49. A light guide 51 inserted in the inserting section 41 has an end thereof which is fixedly mounted on the gripper 42', and which is provided with a mouthpiece or base 51a to which a connector at one end of a light cable 44 is connected. The other end of the light guide cable 44 is connected to a light-source unit 35 by a connector 45. An ocular window opposed to ocular lenses 54 is closed by a cover glass material 54a.

The rigid endoscope 32' can be processed in sterilization by the autoclave unit, and can also be processed in EOG sterilization by an EOG sterilization unit.

Other arrangements are similar to those of the first embodiment illustrated in FIG. 1.

Figure 6:
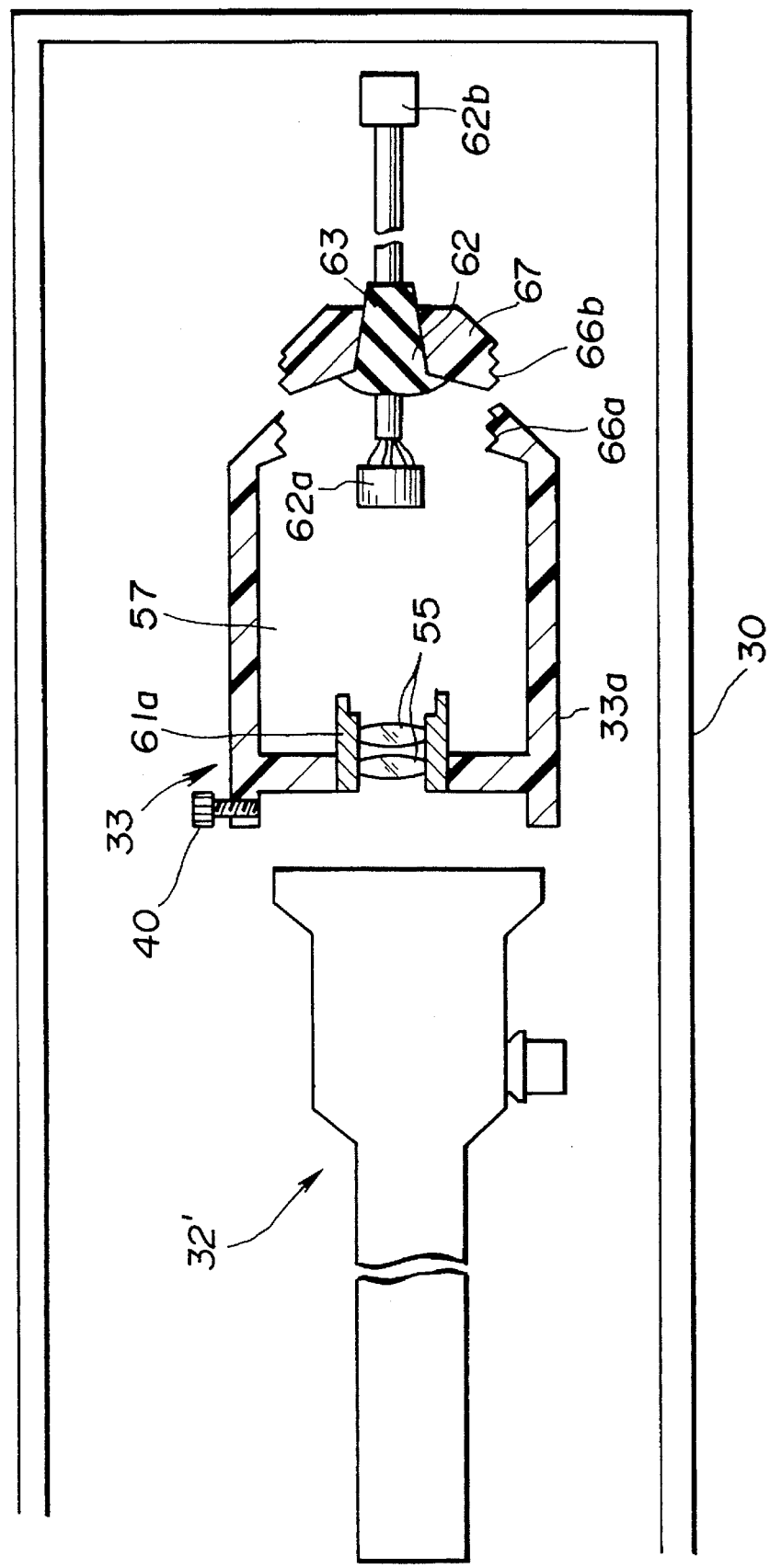
FIG. 6 is a view showing an aspect in which the outside mounted camera from which an image pickup unit is dismounted is received in an autoclave unit together with the endoscope.

In this modification, it is possible that an image pickup unit 68 is taken out after use, and is processed in sterilization by an autoclave unit 30 together with the rigid endoscope 32' as illustrated in FIG. 6.

FIGS. 7a and 7b show an outside mounted camera 1 which forms a second embodiment of the invention.

As shown in FIG. 7a, the outside mounted camera 1 forming the second embodiment of the invention comprises a camera head 4 capable of being mounted on an ocular portion 3 of an optical endoscope 2 such as the fiber scope 32 or the like illustrated in FIG. 1 or on a rigid endoscope provided with a rigid inserting section, and a camera cable 5 extending from the camera head 4. A connector 6 is provided at a proximal end of the camera cable 5, and can be connected to a CCU serving as a signal processing means (not shown).

As shown in FIG. 7b, a camera head 4 comprises an optical adaptor 8 provided with an imaging lens system 7, a TV camera body (a frame body) 11 detachably mounted on the optical adaptor 8 and having built therein a CCD 9, and a camera head cover element (referred simply also to as a "cover element") 12 detachably mounted on the optical adaptor 8 under such a condition that the TV camera body 11 is received within the camera head cover element 12 and under such a condition that the TV camera body 11 is dismounted from the camera head cover element 12.

The optical adaptor 8 is arranged such that the imaging lens system 7 is mounted on a frame substantially in the form of a ring. Thus, it is possible to rotate a gripping portion 13 of a fixed screw under such a condition that a mount opening at a forward surface is fitted over the ocular portion 3, so as to be mounted on and dismounted from the ocular portion 3. Moreover, the optical adaptor 8 has a rearward end portion thereof in a surface of which is provided therein with an axial and peripheral grooves 14. A projection 15 projecting toward an inside of a front surface of the TV camera body 11 is received in this groove 14. The projection 15 moves to a peripheral groove portion in a deepest portion of the groove 14, whereby it is possible to mount and dismount the TV camera body 11 on and from the optical adaptor 8 by opposite movement.

The optical adaptor 8 is arranged such that its frame portion and the imaging lens systems 7 are formed by a material withstanding autoclave processing. For example, the frame portion is made of a metallic material, or a material capable of withstanding the autoclave processing, such as a high function engineering plastic material or the like capable of withstanding a temperature higher than normal or ordinary plastic materials.

Under a condition illustrated in FIG. 7a that the optical adaptor 8 is mounted on the ocular portion 3, and the TV camera body 11 is further mounted on the optical adaptor 8, an optical image transmitted toward the ocular portion 3 by an image guide (not shown) of the endoscope 2 is imaged on an image pickup surface (photoelectric transfer surface) of the CCD 9 which is built in the TV camera body 11. The CCD 9 is arranged such that a periphery other than a portion adjacent to a front surface of the image pickup surface of the CCD 9 is covered by the TV camera body 11.

A projecting portion 17 formed peripherally of the inward side of the front surface of the head cover element 12 which has a diameter thereof larger than a rearward portion, which is formed with a peripheral groove 16, and which is received in the peripheral groove 16 is received in the outer peripheral surface on the front side adjacent to the rearward end portion in the optical adaptor 8, whereby it is possible to mount the head cover element 12 on the optical adaptor 8.

Figure 8A:
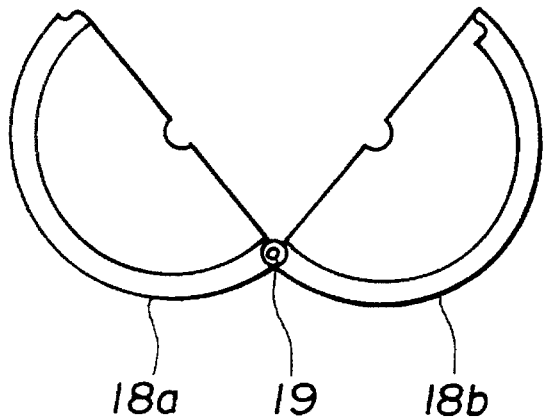
FIGS. 8a and 8b are a front elevational view showing a condition under which a head cover element is opened and a condition under which the head cover element is closed.

As shown in FIG. 8a, the head cover element 12 has a structure in which a pair of split half-cylindrical elements 18a and 18b formed such that a cylindrical element is divided into two longitudinally along a plane passing a diameter of the cylindrical element are connected to each other by a pivot element 19 in the form of a hinge, for example, and which is angularly moved about the pivot element 19. If the semi-cylindrical elements 18a and 18b formed with a click mechanism are moved angularly so that peripheral ends of the respective semi-cylindrical elements 18a and 18b are overlapped with each other, a cylindrical configuration can be obtained as shown in FIG. 8b.

Figure 8B:
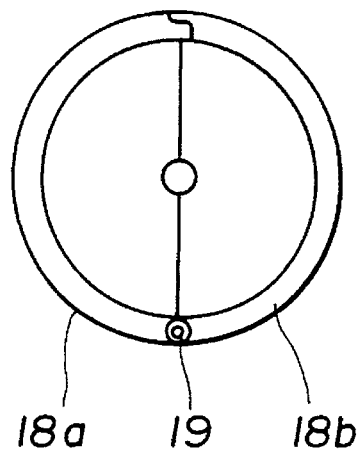

In a case where the head cover element 12 is brought to a state or condition illustrated in FIG. 8b, one end brought to a front surface side of a cylinder is open, while the other end is brought to a small opening urged against the camera cable 5.

The head cover element 12 is formed by a material which can withstand autoclave processing such as a high function engineering plastic material or the like which can withstand temperature higher than ordinary or normal plastic.

The camera cable 5 extending from the TV camera body 11 can be covered with a cable cover 20a which is formed by a high function engineering plastic material, for example.

Specifically, as shown in FIGS. 7a and 7b, a cable cover 20a covers the connector 6 from a connection with respect to the TV camera body 11. The cable cover 20a can be dismounted from the camera cable 5 by a fastener 20b which is arranged longitudinally of the cable cover 20a.

Figure 9:
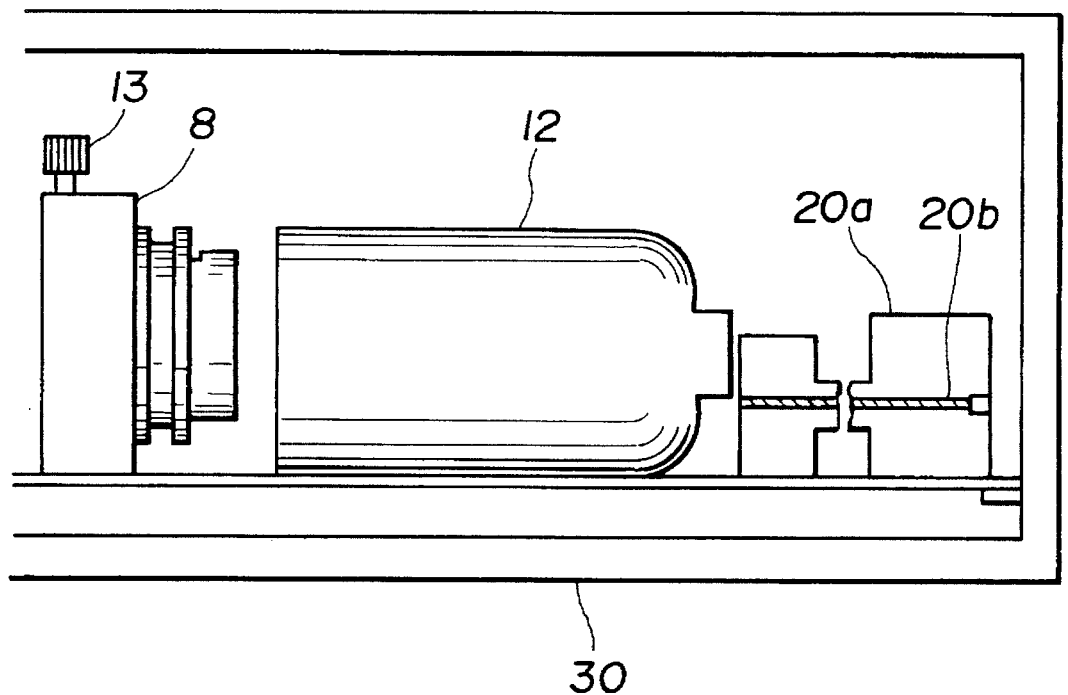

The second embodiment is normally used under a condition shown in FIG. 7a such that the optical adaptor 8 is mounted on the ocular portion 3, the TV camera body 11 is mounted on the optical adaptor 8, and the head cover element 12 is mounted on the optical adaptor 8 under such a condition that the TV camera body 11 is covered. After the use, the TV camera body 11 mounted on the optical adaptor 8 is dismounted, and the optical adaptor 8, the head cover element 12 and the cable cover 20a are received within the autoclave unit 30 as illustrated in FIG. 9, to execute autoclave processing.

In this case, since the condition is under a condition that the TV camera body 11 provided with the CCD 9 low in heat resistance is dismounted, the autoclave processing is made possible. According to the first embodiment of the invention, if the optical endoscope 2, the optical adaptor 8, the head cover element 12 and the cable cover 20a are formed by a material capable of withstanding the autoclave processing, it is possible to easily cope with the autoclave processing. In this embodiment, the head cover element 12 and the cable cover 20a can be used repeatedly.

Figure 10:
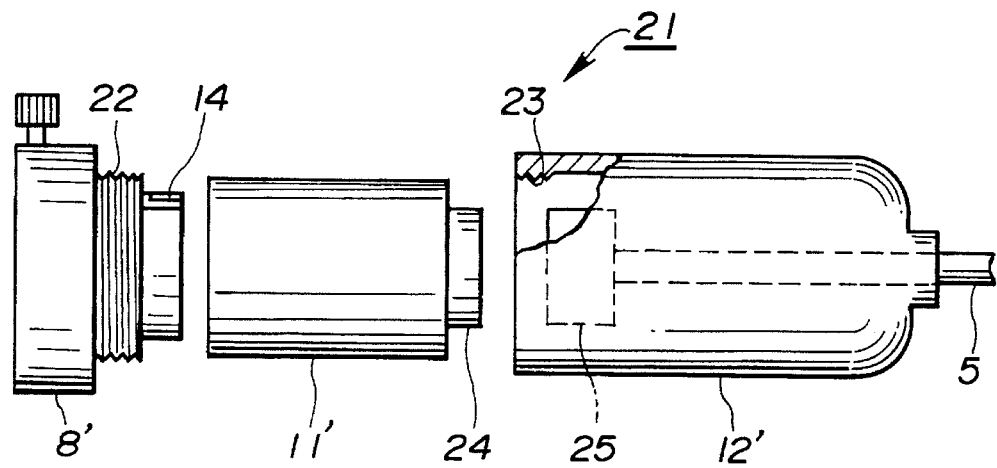
FIG. 10 is a side elevational view showing an outside mounted camera 21 in decomposition in accordance with a third embodiment of the invention.

FIG. 10 shows an outside mounted camera 21 in accordance with a third embodiment of the invention, in decomposition or resolution. The embodiment is arranged such that the detachable mechanism between an optical adaptor 8 and the head cover element 12 in accordance with the second embodiment of the invention is formed by threaded engagement, and a camera cable 5 is brought to a structure capable of being mounted on and dismounted from the optical adaptor 8. Thus, the third embodiment is arranged such that the cable cover 20a is unnecessary or is dispensed with.

Specifically, in the optical adaptor 8' in accordance with the present embodiment of the invention, a female thread portion 22 is formed on a portion where the peripheral groove 16 in the optical adaptor 8 in the first embodiment of the invention is formed, and a female threaded portion in mesh with the male threaded portion 22 is formed in the forward end of a head cover element 12'.

Furthermore, the third embodiment is arranged such that a detachable connector 25 is provided at a connector receptor 24 of the TV camera body 11' at a location at the proximal end portion of the camera cable 5. The camera cable 5 is formed by a material withstanding the autoclave processing, together with the connectors 6 and 25.

Figure 11:
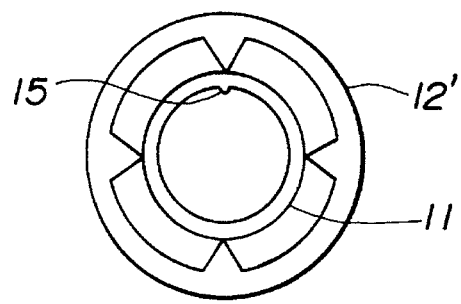
FIG. 11 is a view showing a camera head cover element.

Moreover, the head cover element 12' in the present embodiment is arranged such that a projection is provided radially on the inward side in the radial direction as shown in FIG. 11, to prevent the TV camera body 11' from being moved rotatively. Others are similar in arrangement to the first embodiment of the invention, and the description thereof will be omitted.

In this embodiment, after the outside mounted camera 21 has been used, the TV camera body 11' is dismounted to execute autoclave processing of the optical adaptor 8', the head cover element 12' the cable 5 provided with the connectors 6 and 24, and the optical endoscope 2. The present embodiment has advantages substantially similar to those of the second embodiment of the invention.

Figure 12:
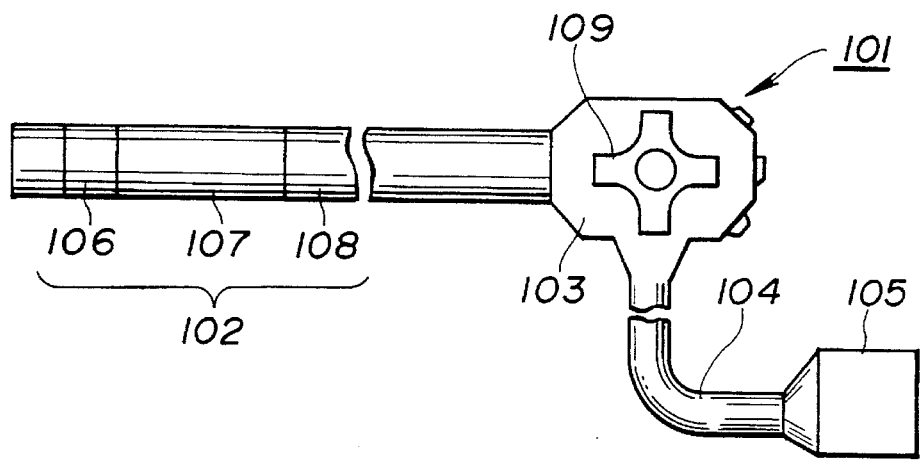
FIGS. 12 through 14 are views showing the third embodiment of the invention, FIG. 12 being a side elevational view showing the entirety of an electronic scope in accordance with the third embodiment of the invention.

FIG. 12 shows an electronic scope 101 serving as an electronic endoscope in accordance with a fourth embodiment of the invention. The electronic scope 101 comprises an elongated inserting section 102, an operating section 103 large in diameter and connected to a rearward end of the inserting section 102, and a universal cable 104 extending from a side of the operating section 103. A connector 105 provided at a proximal end of the universal cable 104 can detachably be connected to a CCU or a video processor (both not shown).

Figure 13:
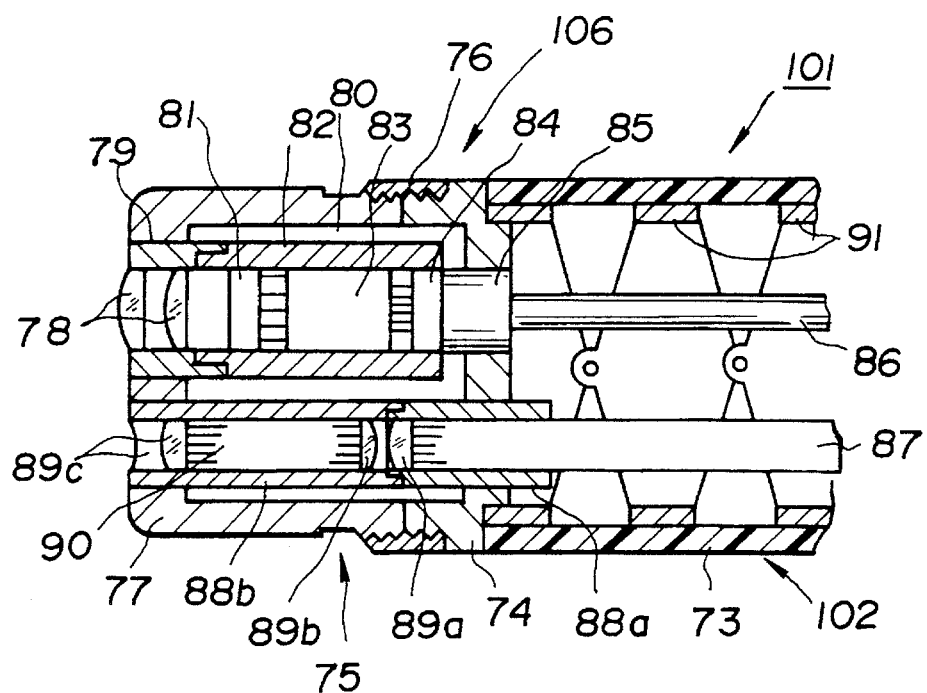

The inserting section 102 comprises a hard forward end portion 106, a curving portion 107, and a flexible tube portion 108. A curving knob 109 provided at the operating section 103 is operated whereby the curving portion 107 can be curved. The forward end portion 106 is arranged as illustrated in FIG. 13.

An armored tube 73 forming the inserting section 102 has a forward end thereof at which a hard forward end element 74 forming the forward end portion 106 is provided. The forward end element 74 has a front surface thereof on which an image pickup adaptor 75 is detachably mounted.

Specifically, an outer peripheral surface of the forward end element 74 and an outer peripheral surface of the image pickup adaptor 75 are provided with screws. Under a condition that a rearward surface of the image pickup adaptor 75 is in contact with the forward surface of the forward end element 74, both elements can be fixedly connected to each other by a connecting ring 76 provided with a female screw.

Objective lenses 78 are mounted on an observation window provided in a front surface of an armored frame 77 forming the image pickup adaptor 75, through a lens frame 79. A CCD frame 82 on which a CCD 81 forming an image pickup unit 80 is mounted is fitted in the lens frame 79, whereby the objective lenses 78 can be mounted on the lens frame 79. Under this condition, the CCD 81 is located at a focus surface of the objective lenses 78.

The CCD 81 cooperates with a hybrid substrate 83 arranged adjacent to a rear surface of the CCD 81, and a connector 84 arranged rearwardly of the hybrid substrate 83 and integrated by a connector 84 fixedly mounted on the CCD frame 82 together with the hybrid substrate 83, to form the image pickup unit 80.

A signal photoelectrically transferred by the CCD 81 passes through the hybrid substrate 83 and, subsequently, is transmitted to a connector 84 which is electrically connected to the hybrid substrate 83.

Further, a signal passes through a transmission cable 86 on which a connector receptor 85 detachably connected to the connector 84 is mounted, and reaches an electrical contact of the connector 105 of the universal cable 104.

The connector receptor 85 is fixedly mounted on the forward end element 74 so that the connector 84 can be mounted from a forward point and can be dismounted by reverse operation. Under a condition that the image pickup adaptor 75 is dismounted from the forward end element 74, when the connector 84 is dismounted from the connector receptor 85, it is possible to dismount the image pickup unit 80.

A light guide 87 for transmitting an illuminating light is inserted in the armored tube 73. The light guide 87 has a forward end thereof which is fixedly mounted on the forward end element 74 by a pipe 88a. A lens 89a is fixedly mounted on the forward end surface of the light guide 87. A pipe 88b fitted over the pipe 88a is provided also on the image pickup adaptor 75. A short light guide 90 is inserted also in the pipe 88b. A plurality of lenses 89b and 89c are mounted respectively on both ends of the pipe 88b. The arrangement is such that the two pipes 88a and 88b are of structures fitted with each other so that the illuminating light can be transmitted without leakage. The illuminating light transmitted to the light guide 90 is outgone forwardly from the lens 89c mounted on the illuminating window.

In connection with the above, a pair of curving pieces 91 and 91 forming the curving section are connected in a longitudinal row to the rearward end of the forward end element 74 so as to be capable of moving angularly. The forward end element 74 has an outer side which is covered with the armored tube 73.

As shown in FIG. 13, the present embodiment can be used for observation and the like as an electronic scope 101 under a condition that the CCD frame 82 of the image pickup unit 80 is connected to the lens frame 79, the connector 84 is connected to the connector receptor 85, and the connecting ring 76 is moved angularly so that the image pickup adaptor 75 is connected to the forward end element 74.

After the use, it is possible to angularly move the connecting ring 76 to separate the image pickup adaptor 75 from the forward end element 74. The CCD frame 82 of the image pickup unit 80 is pulled from the image pickup adaptor 75, whereby it is possible to dismount the image pickup unit 80 from the image pickup adaptor 75. A condition under which the image pickup unit 80 is dismounted is illustrated in FIG. 14.

Figure 14:
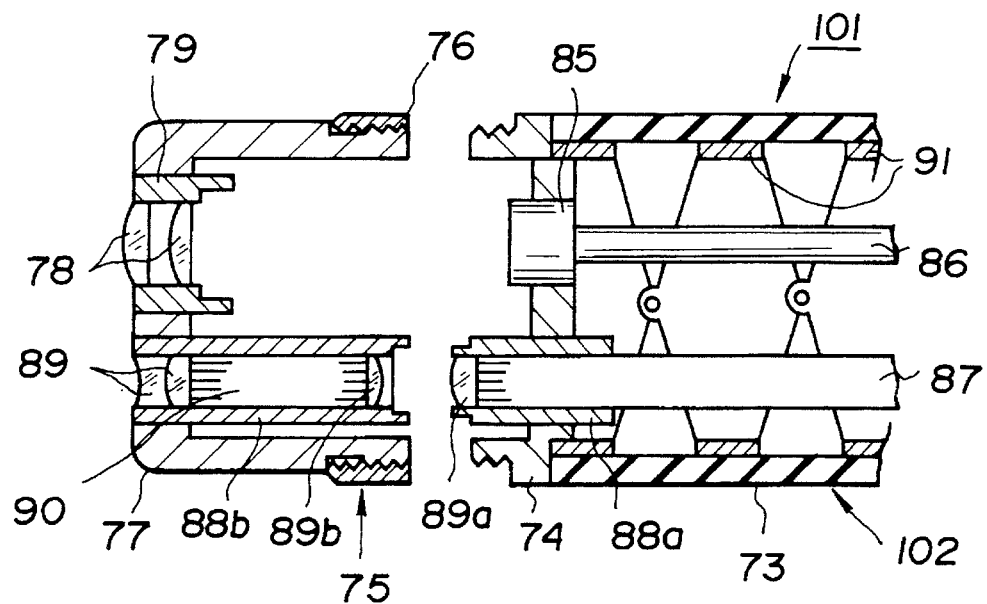

It is possible to process, in sterilization, the image pickup adaptor 75 from which the image pickup unit 89 illustrated in FIG. 14 is dismounted, by the autoclave unit.

Furthermore, it is possible to process, in sterilization, the image pickup adaptor 75 from which the image pickup unit 80 is removed or dismounted, by the EOG sterilization unit together with the electronic scope body (an article in which the image pickup adaptor 75 is removed from the forward end element 74 in FIG. 13).

Figure 15:
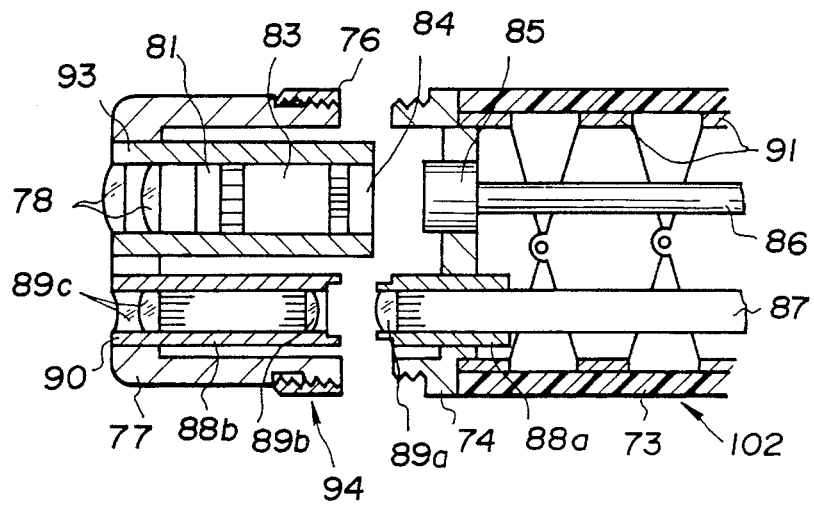
FIG. 15 is a cross-sectional view showing an arrangement of a forward end portion in accordance with a modification of FIG. 14.

FIG. 15 shows a side adjacent to the forward end of the electronic scope in a modification of the fourth embodiment. The modification is arranged such that, in FIG. 13, the lens frame 79 and the CCD frame 82 are integrated with each other to form a frame 93, to form an image pickup adaptor 94. With the arrangement, it is possible to process, such as disinfection and sterilization, the image pickup adaptor 94 and a portion adjacent to the electronic scope body from which the image pickup adaptor 94 is dismounted, under conditions different from each other. After the disinfection and sterilization processing, it is possible to again mount the image pickup unit 94 on the electronic scope body to use the electronic scope.

Specifically, the electronic scope can be separated into two elements. Resistances with respect to disinfection and sterilization processing of the two elements are different from each other. Accordingly, disinfection and sterilization processing is executed under disinfection and sterilization processing conditions different from each other, after the use in an organism.

Figure 16:
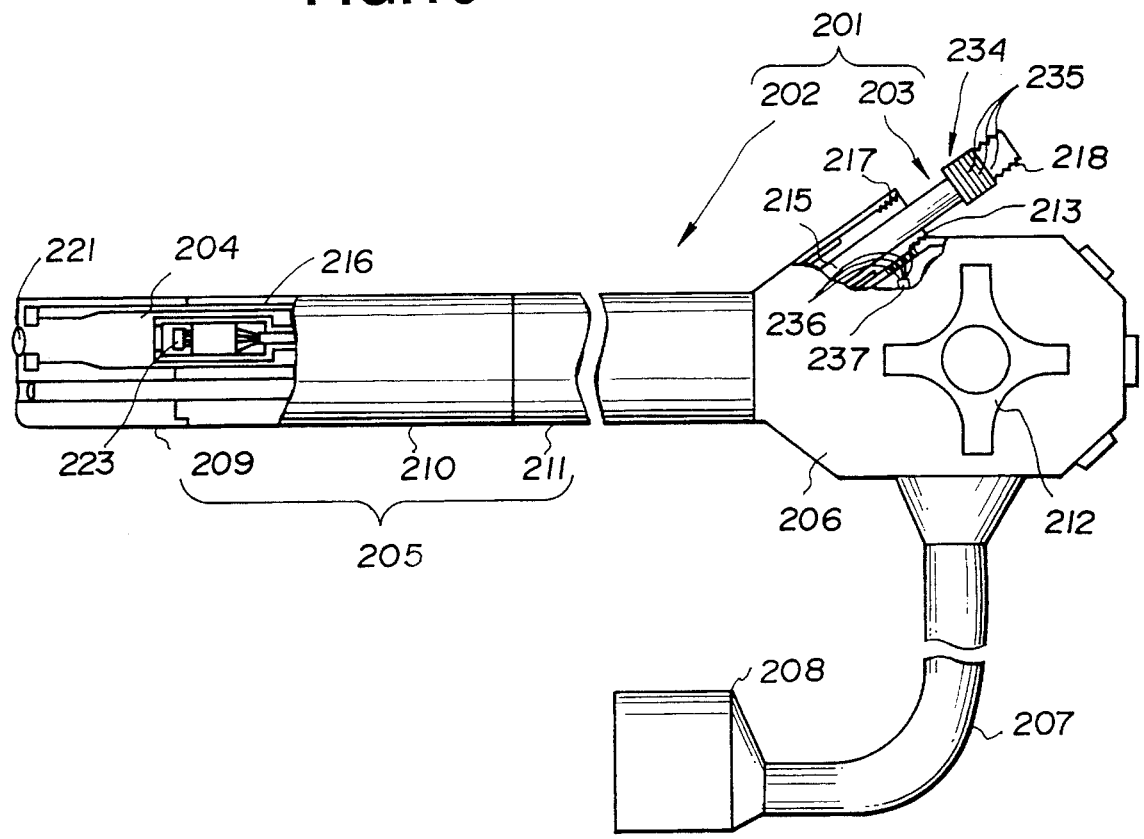
FIGS. 16 through 18 are views showing a fourth embodiment of the invention, FIG. 16 being a side elevational view showing the entirety of an electronic scope in accordance with the fourth embodiment of the invention.

FIG. 16 shows a fifth embodiment of the invention. An electronic scope 201 comprises an electronic scope body 202, and an image pickup unit 203 detachably mounted on a unit receiving line 204 provided on the electronic scope body 202.

The electronic scope body 202 comprises an elongated inserting section 205, an operating section 206 and a universal cable 207. A connector 208 provided at a terminal end of the universal cable 207 can detachably be connected to a CCU (not shown).

The inserting section 205 has a hard forward end portion 209, a curving portion 210, and a flexible tube portion 211. A curving knob 212 is provided on the operating section 206.

The operating section 206 of the electronic scope body 202 is provided therein with a unit inserting port 213. It is possible to insert the image pickup unit 204 to a location adjacent to a deep portion of the unit receiving line 204 having a line arrangement like a channel, from the unit inserting port 213, and to withdraw the inserted image pickup unit 204.

The image pickup unit 204 comprises an elongated shaft 215, an image pickup portion 216 provided at a forward end (a terminal end) of the shaft 215, and a screw portion 218 provided at a rearward end (a proximal end) of the shaft 215 and threadedly engaged with a screw portion 217 provided at the unit inserting port 213. Threaded engagement between the two screw portions 217 and 218 enables the image pickup unit 203 received in the unit receiving line 204 to be fixedly mounted.

Figure 17:
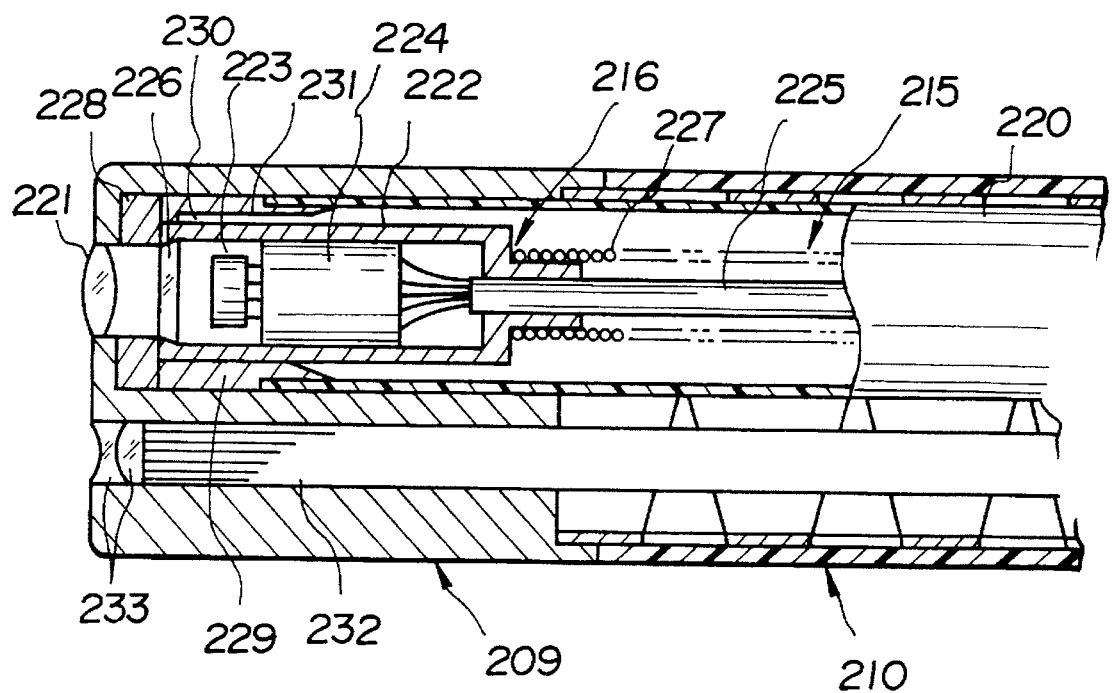

FIG. 17 shows a portion adjacent to the forward end under such a condition that the image pickup unit 203 is received in the unit receiving line 204.

A tube 220 forming the unit receiving line 204 is fixedly mounted on a through bore communicating with an observation window provided at the forward end portion 209. An objective lens 221 is mounted on the observing window. The image pickup portion 216 is received in a space on the inside of the objective lens 221. The image pickup portion 216 is arranged such that a CCD 223 and a peripheral circuit block 224 forming a CCD drive circuit and the like are received within the cylindrical frame 222. The peripheral circuit block 224 is connected to the cable 225. A cover glass material 226 serving as a transparent optical element is mounted on a front surface of the frame 222, to protect the inside CCD 223. Further, a closely wound coil 227 forming a shaft 215 has a forward end which is fixedly mounted on the proximal end of the frame 222.

The frame 222 is formed by a magnetic substance or material. The frame 222 is attracted toward a ring-like magnet 228 which is fixedly mounted on an inside of an observing window. A periphery at the front surface of the image pickup portion 216 is abutted against a rear surface of the magnet 228, whereby the image pickup portion 216 is positioned (in a direction of optical axis).

Figure 18:
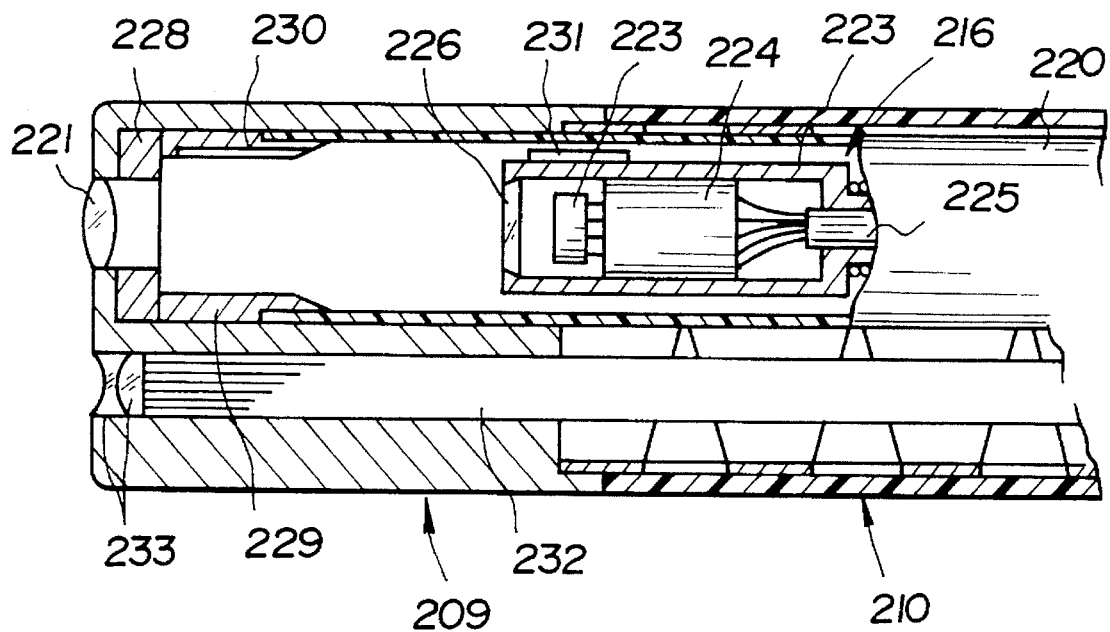

Furthermore, a ring 229 having an inner diameter substantially equal to an outer diameter of the image pickup portion 216 is fixedly mounted on a rear surface of the magnet 228, to execute positioning of the image pickup portion 216 (in a direction perpendicular to the optical axis). Moreover, the ring 229 is provided therein with a key groove 230 as shown in FIG. 18. A key projection 231 provided on the frame 222 of the image pickup portion 216 is fitted in the key groove 230, so that positioning in a peripheral direction can be executed.

The light guide 232 is inserted adjacent to the unit receiving line 204. The light guide 232 has a forward end thereof which is fixedly mounted on the illuminating window, to project the transmitted illuminating light forwardly from the forward end surface further through the illuminating lens 233, thereby illuminating a forward subject such as the affected or diseased part or the like.

In connection with the above, as shown in FIG. 16, an insulating ring 234 provided adjacent to the threaded portion 218 at a rearward end of the shaft 215 of the image pickup unit 204 is provided with ring-like contacts 235, 235, . . . which is connected to each signal line within the cable 225. In a case where the threaded portions 217 and 218 are threadedly engaged with each other, the ring-like contacts 235, 235, . . . are conducted to the contact receptors 236, 236, . . . which are provided on the inner surface of the unit inserting opening 213. Each contact receptor 236 is connected to the signal line of the cable 237, respectively. The cable 237 reaches the connector 208 through the universal cable 207.

In this embodiment, operation is executed such that the image pickup unit 204 is inserted into the unit inserting port or opening 213 and is pushed thereinto, whereby the image pickup unit 204 can be inserted toward the deep portion of the unit receiving line 204. The image pickup portion 216 at the forward end of the image pickup unit 204 is attracted by the magnet 228, and is set to a condition as illustrated in FIG. 17.

On the other hand, after the electronic scope 201 has been used, the threaded engagement is released, and the rearward end is pulled, whereby it is possible to release the image pickup unit 203 from the body 202. For example, the body 202 can be processed in sterilization by the EOG sterilization unit. In a case of being used, the image pickup portion 216 of the image pickup unit 203 and the shaft 215 are not exposed. Accordingly, it is unnecessary to process, in sterilization, the image pickup unit 203 by the EOG sterilization unit. In this connection, since the rearward end of the threaded portion 218 is exposed, wiping is executed by a cloth or the like to which disinfection liquid such as alcohol or the like is adhered. The threaded portion 218 is detachable from the shaft 215, whereby the threaded portion 218 may be processed in sterilization together with the body 202.

Figure 19:
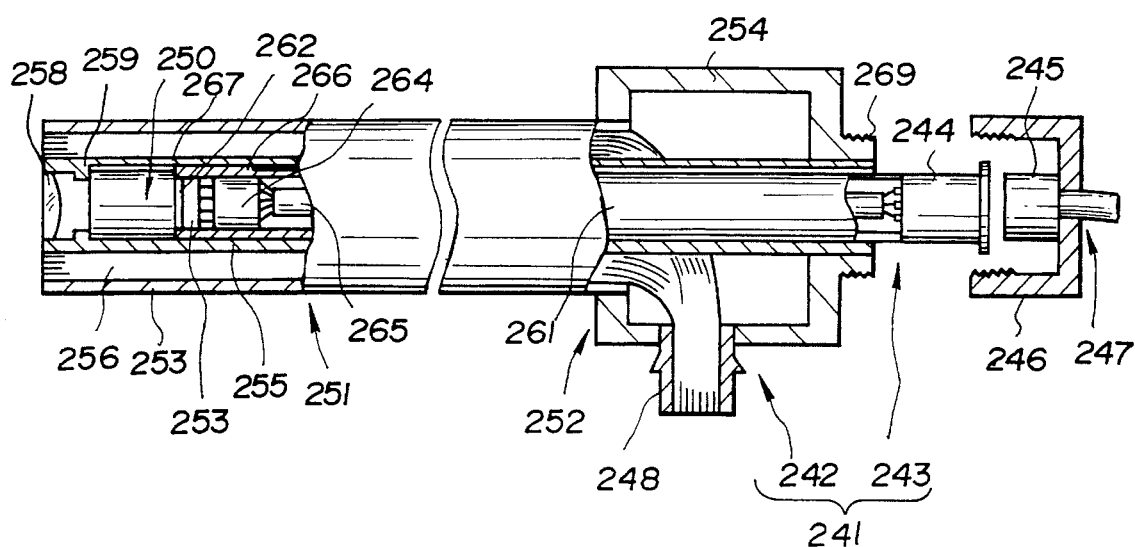
FIGS. 19 and 20 are views showing a fifth embodiment of the invention, FIG. 19 being a cross-sectional view showing an electronic scope in accordance with the fifth embodiment of the invention under a condition on the way that an image pickup unit is dismounted.

FIG. 19 shows a hard electronic scope 241 in accordance with a sixth embodiment of the invention. The hard electronic scope 241 comprises an electronic scope body 242, an image pickup unit 243 detachably (capable of being inserted) mounted on the electronic scope body 242, and a connector receptor 245 connected to a connector 244 at a proximal end of the image pickup unit 243. Further, the hard electronic scope 241 comprises a connecting cable 247 having a fixing ring 246 for fixing the image pickup unit 243 to the electronic scope body 242, and a light guide cable (not shown) connected to a light guide base 248 provided on the electronic scope body 242.

The electronic scope body 242 comprises a hard inserting section 251 and a grip section 252 wide in width and connected to a proximal end of the inserting section 251. The hard inserting section 251 is formed by a pipe 253 made of a metal such as stainless steel or the like. The proximal end of the pipe 253 is fixedly mounted on a forward end of the cylindrical frame 254 forming the grip portion 252. A pipe 255 is inserted within the pipe 253. The rearward end (proximal end) of the pipe 255 is fixedly mounted on the rearward end of the frame 254. A light guide 256 is inserted into a space between the outside pipe 253 and the inside pipe 255. The rearward end of the light guide 256 is fixed by the light guide base 248.

An objective lens 258 is fixedly mounted on the forward end of the inside pipe 255. A positioning projection 259 is provided at a location slightly rearward from the objective lens 258. A unit receiving portion 260 capable of receiving the image pickup unit 243 is formed within the pipe 255 rearwardly from the projection 259.

An opening at the rearward end of the pipe 255 forms an inserting port for the image pickup unit 243, so that the image pickup unit 243 can be inserted and withdrawn. The image pickup unit 243 is arranged such that a CCD 263 protected by the cover glass material 262 is received in and is fixedly mounted on the forward end of the pipe 261 whose outer diameter is substantially the same as the inner diameter of the pipe 255. A peripheral circuit 264 having a function of an amplifier amplifying a CCD output signal is arranged adjacent to the rear surface of the CCD 263. The peripheral circuit 264 is connected to the cable 265.

The cable 265 is connected to the connector 244 which is arranged at the rearward end of the pipe 261. A key projection 266 is provided on the outer surface of the pipe 261. The key projection 266 is fitted in the key groove 267 provided adjacent to the pipe 255, whereby it is possible to peripherally position the image pickup unit 243. Under this condition, the pipe 261 is pushed into or is depressed so that the forward end of the pipe 261 is set to a position abutted against the projection 259, whereby it is possible to execute positioning in the optical axis direction. The connector receptor 245 of the cable 247 is connected to the connector 244, and the threaded portion of the ring 246 is threadedly engaged with the threaded portion 269 at the rearward end of the grip portion 252, whereby setting can be made to a mounting condition (a condition capable of being used as an electronic scope) as shown in FIG. 20.

Figure 20:
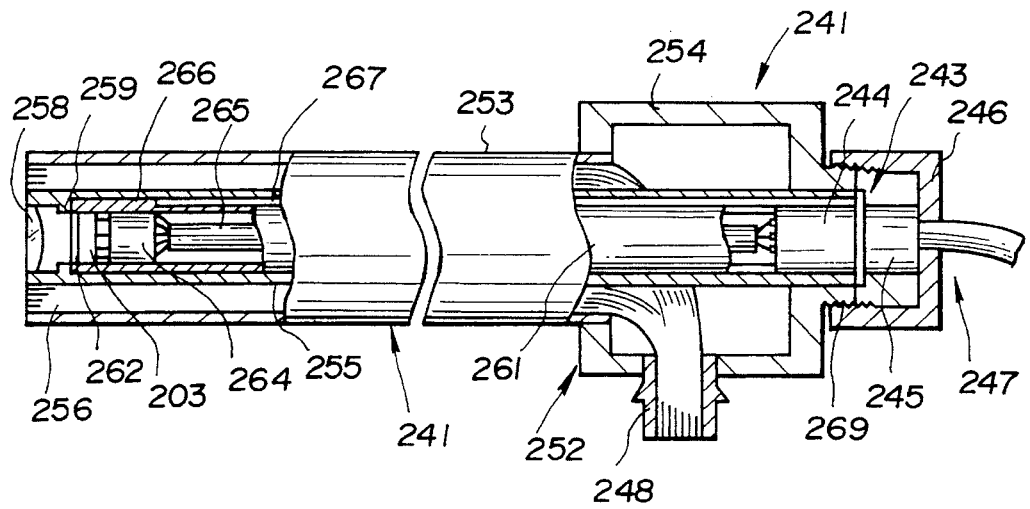

The electronic scope 241 shown in FIG. 20 is arranged such that the light-source unit 35 and the CCU 36 illustrated in FIG. 5 are connected to each other, whereby it is possible to display an endoscope image or picture image-picked-up by the CCD 263 on the monitor 37. After having been used for observation of an organism or the like, the ring 246 is dismounted from the grip portion 252 as shown in FIG. 19, whereby it is possible to dismount the image pickup unit 243 from the endoscope body 242. It is also possible to process, in autoclave, the endoscope body 242 and the cable 247 by the autoclave unit.

Figure 21:
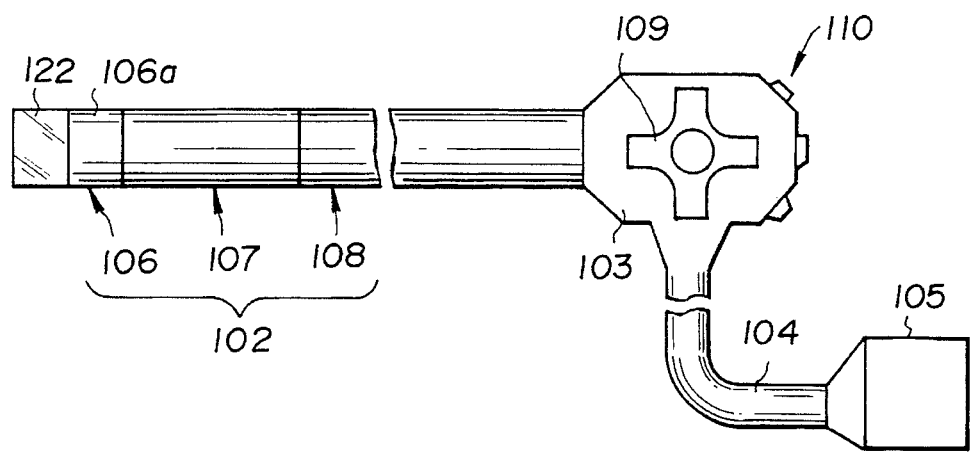
Figure 22A:
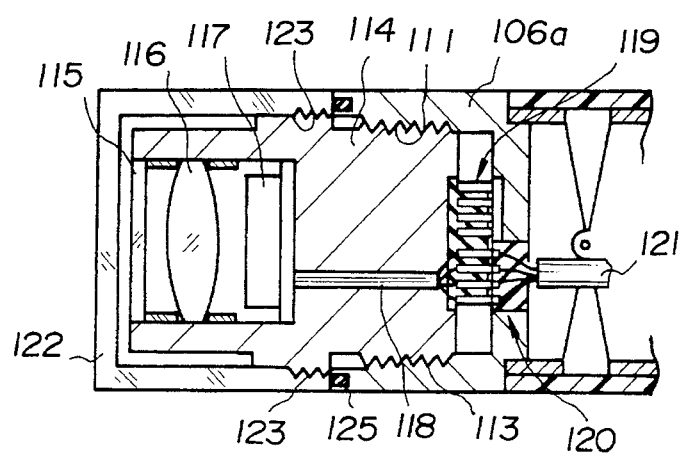
Figure 22B:
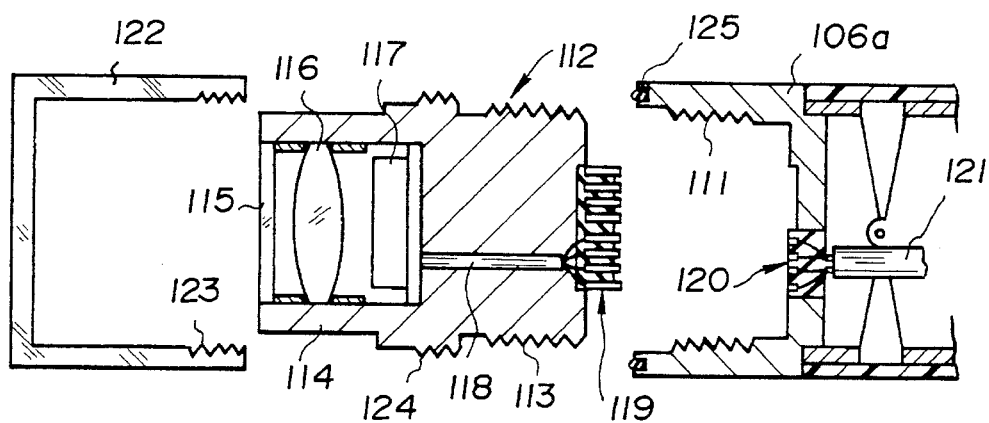

FIG. 21 shows an electronic scope 110 in accordance with a seventh embodiment of the invention. An outer configuration of the electronic scope 110 is the same as that of the electronic scope 101 illustrated in FIG. 12, and the same or identical components and parts are designated by the same or identical reference numerals. The forward end side of the electronic scope 110 is arranged such that, as shown in FIGS. 22a and 22b, a recess in the form of a column is formed adjacent to the forward surface of the forward-end body 106a forming a forward end portion 106, and a female threaded portion 111 is provided on the peripheral surface within the recess. A portion adjacent to the proximal end of the image pickup unit 112 can detachably be received in the recess. That is, a male threaded portion 113 provided on the outer peripheral surface adjacent to the proximal end of the image pickup unit 112 is threadedly engaged with the female threaded portion 111 so that mounting can be made.

The image pickup unit 112 is arranged such that a unit body portion 114 is formed substantially into a columnar configuration, a recess symmetrical in rotation with respect to the central axis of the column is formed adjacent to the forward end of the image pickup unit 112, and the cover glass material 115, the objective lens 116 and the CCD 117 are received in and are fixedly mounted in the recess. The CCD 117 is electrically conducted to a contact portion 119 which is provided on a rear surface of the unit body portion 114 by the cable 118 through a substrate on the rear surface.

The contact portion 119 is arranged such that a plurality of contacts formed by a plurality of rings and arranged concentrically about a central axis, for example, are provided on an insulating element. When the image pickup unit 112 is mounted in the recess in the forward end portion 106, the contact portion 119 provided in projection on the rear surface of the unit body portion 114 is in contact with a contact receipt portion 120 which is formed by a plurality of radially spaced contacts provided on the recess in the forward end portion 106a. The contact receptor 120 reaches an electric contact of the connector 105 through the cable 121.

A threaded portion 124 threadedly engaged with the threaded portion 123 provided adjacent to the rearward end of the transparent cover element 122 is provided on the outer peripheral surface of the unit body portion 114. A portion of the unit body portion 114 mounted on the recess, which is exposed from the recess, can be covered by the cover 122. A packing 125 is received in a groove portion between the rearward end surface of the cover 122 and the forward end surface of the forward-end body portion 106 so that the cover 122 is mounted so as to compress the packing 125, whereby invasion of liquid or the like toward the image pickup unit 112 which is received within the cover 122 is prevented. Specifically, the image pickup unit 112 is prevented from being contaminated by use. After having been used under the mounting condition illustrated in FIG. 20a, the cover 122 is dismounted, and the image pickup unit 112 is dismounted from the forward-end body portion 106a, so that a condition can be brought to a condition illustrated in FIG. 20b.

Constitutional elements other than the image pickup unit 112, that is, the cover 122 and the endoscope body (a portion to the right from the forward-end body 106a in FIG. 19) can be processed in sterilization by the EOG sterilization unit, and can be processed in sterilization by the autoclave unit. The present embodiment is arranged such that the objective lens 116 and the CCD 117 are received within the image pickup unit 112 whose front surface is protected by the cover glass material 115. Accordingly, it is possible to easily process in sterilization the image pickup unit 112 per se by the EOG sterilization unit, and to dip the image pickup unit 112 per se in disinfection liquid to process in disinfection the image pickup unit 112.

The electronic scope and the outside mounted camera which are of an adiabatic structure in which heat is difficult to be transmitted to the image pickup means, to improve head insulation of image pickup means so that autoclave processing is possible, or thermal sterilization processing is possible under a condition approximate to the autoclave processing will be described with reference to FIGS. 23 to 31.

Figure 23A:
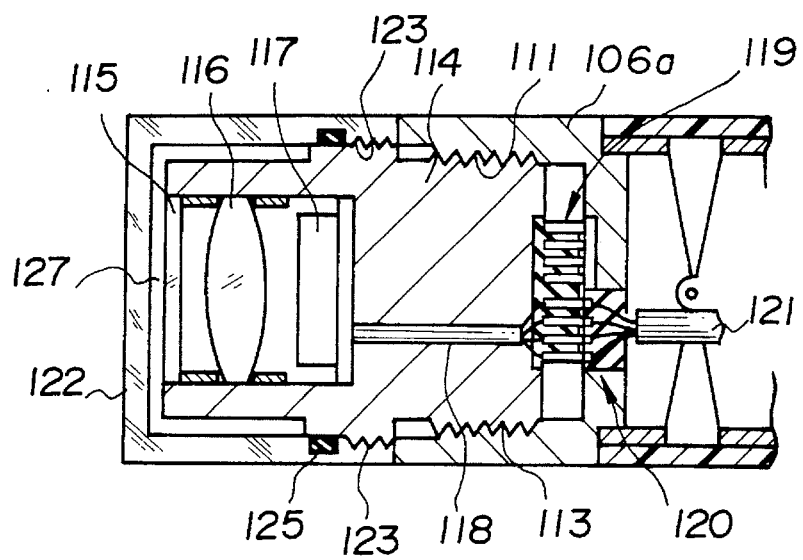
FIGS. 23a and 23b are cross-sectional views showing a structure of a forward end portion of an electronic scope having an adiabatic or heat-insulated structure under a condition in which an image pickup unit is mounted and under a condition in which the image pickup unit is dismounted.
Figure 23B:
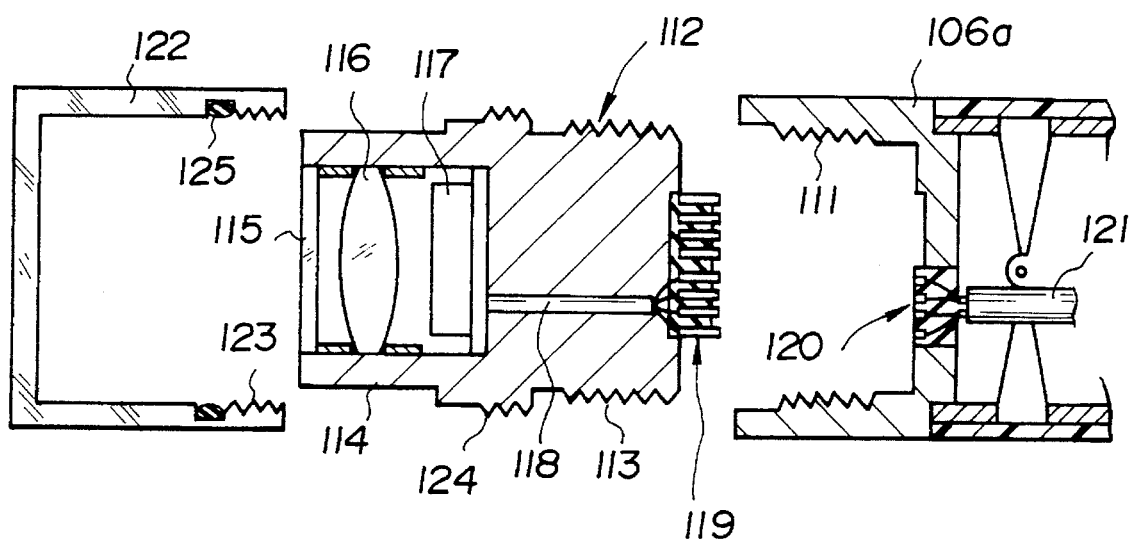

FIG. 23 shows a portion adjacent to the forward end of the electronic scope 301. The electronic scope 301 has an outer configuration thereof which is the same as FIG. 21. The electronic scope 301 is of structure in which a peripheral groove is provided in an inner peripheral surface of the cover 122 as shown in FIG. 22, a packing 125 is received in the peripheral groove, and a space inside from the packing 125 is kept air-tightly. In a case where the cover 122 is mounted on the image pickup unit 112, a structure is adopted in which the image pickup unit 112 and the cover 122 do not come in contact with each other except for a portion where the threaded portion 123 and the threaded portion 124 are threadedly engaged with each other, and except for a closely contact portion by the packing 125, as shown in FIG. 23a.

Accordingly, when the cover 122 is mounted on the image pickup unit 112, mounting or attachment is made within a vacuum tank together with the image pickup unit 112 dismounted from the body portion 106a at the forward end portion, whereby a vacuum layer 127 superior in adiabatic function can be formed between the image pickup unit 112 and the cover 122.

In a case where processing is made in the autoclave unit by the vacuum layer 127, the CCD 117 and the like are prevented from being elevated or raised to a temperature exceeding a resistance thereof. Further, the unit body portion 114 of the image pickup unit 112 is formed by a material having a low thermal conductivity. Other arrangements are similar to those illustrated in FIG. 22a and the description thereof will be omitted.

Figure 24:
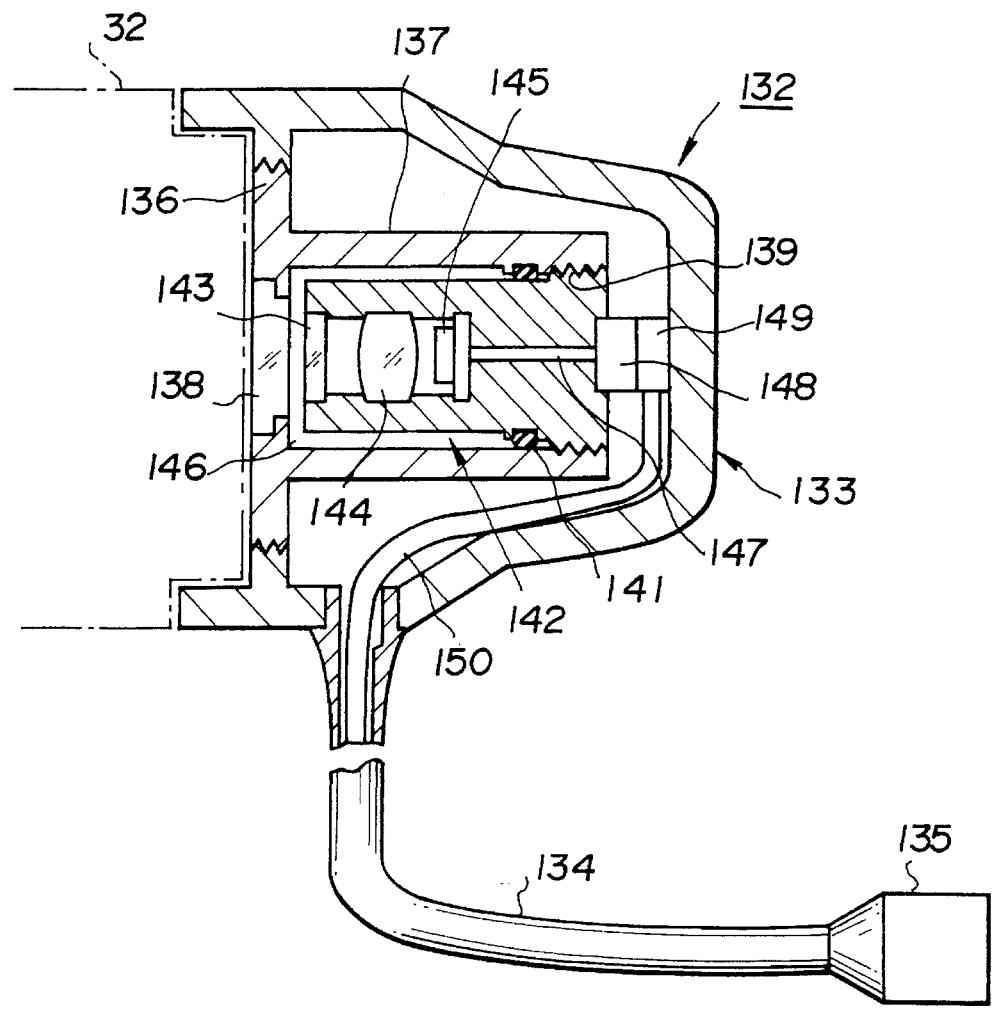
FIG. 24 is a cross-sectional view showing an outside mounted camera having an adiabatic structure.

FIG. 24 shows an outside mounted camera 132 of a camera outside mounted endoscope. The outside mounted camera 132 can detachably be mounted on the fiber scope 32 illustrated in FIG. 1, for example. The outside mounted camera 132 comprises a camera head portion 133 and a camera cable 134 extending from the camera head portion 133. A connector 135 is mounted on a terminal end of the camera cable 134.

The camera head portion 133 is detachable with respect to the cover 137 by the threaded engaging portion 136. The image pickup unit 142 can further be detachably mounted on the cover 137.

The cover 137 is substantially cylindrical having a columnar receiving space. The cover 137 has one end thereof which is closed by a transparent element 138 such as a glass plate, and the other end which is open. The cover 137 is provided with a threaded portion 139 on an inner peripheral surface of the cover 137. Furthermore, a peripheral groove is provided in a deep portion of the threaded portion 137 so that a packing 141 is received. An image pickup unit 142 provided with a threaded portion threadedly engaged with the threaded portion 139 can be mounted on the cover 137.

The image pickup unit 142 is formed with a recess in a body having a substantially columnar configuration so that a cover glass material 143, an imaging lens 144 and a CCD 145 are received and arranged. The image pickup unit 142 has an outer diameter which is set smaller than an inner diameter of the cover 137. In a case where the image pickup unit 142 is mounted on the cover 137, an outer peripheral surface of a major portion of the image pickup unit 142 is spaced away from an inner peripheral surface of the cover 137.

Further, the front surface of the image pickup unit 142 is also spaced away from the inside at the front surface of the cover 137. A vacuum layer 146 maintained under a vacuum condition similar to FIG. 23 is formed in a space of a circumference of the image pickup unit 142.

The CCD 145 is conducted with the contact portion 148 which is provided in projection on the side of the rear surface of the image pickup unit 142, by the cable 147. The contact portion 148 is electrically connected to the contact receptor 149 which is provided at a location opposite to the camera head portion 133. The cable 150 connected to the contact receptor 149 reaches the connector 135.

Figure 25:
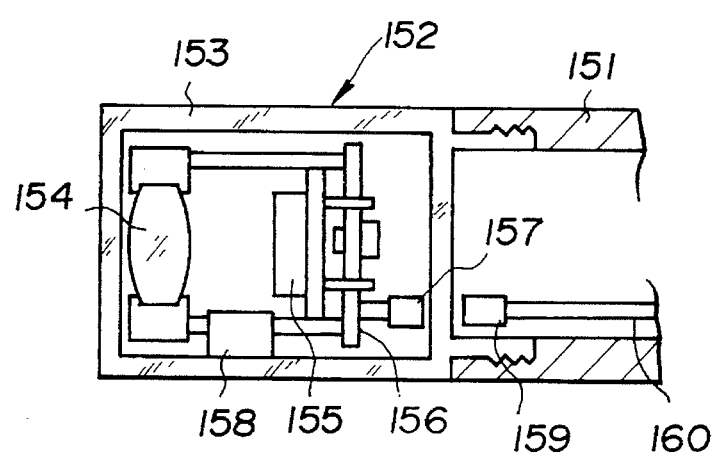
FIG. 25 is a view showing a structure of a forward end portion of an electronic scope having an adiabatic structure.

For example, the forward end portion 106 in the electronic scope 101 illustrated in FIG. 21 is arranged as shown in FIG. 25, thereby being capable of improving a heat resistance and a moisture resistance.

An image pickup unit 152 is detachably mounted on the forward-end body 151 by threaded engaging means. The image pickup unit 152 is arranged such that an objective lens 154 fixedly mounted on a lens frame, a CCD 155, an electronic circuit board 156, an optical communication element 157, and a battery 158 for operating the CCD 155, the electronic circuit board 156 and the like are received within the cylindrical frame 153 whose at least body end surfaces are closed by a transparent glass material or the like. The interior of the cylindrical frame 153 is maintained vacuum.

An optical communication element 159 is arranged also adjacent to the forward-end body 151 in opposed relation to the optical communication element 157. The optical communication element 159 is connected to the connector 105 (refer to FIG. 12) by the cable 160. With the arrangement, since the CCD 155 and the like are received within the vacuum, it is possible to secure a heat resistance in a case of autoclave processing.

Figure 26:
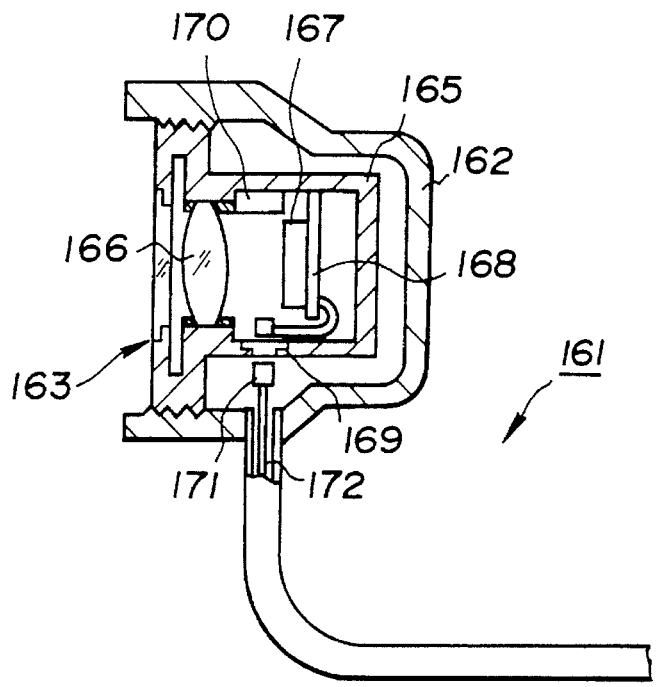
FIG. 26 is a cross-sectional view showing a structure of a modification of FIG. 24.

Furthermore, the outside mounted camera 132 shown in FIG. 24 may be arranged as illustrated in FIG. 26.

The outside mounted camera 161 is arranged such that the image pickup unit 163 is detachable to the camera head frame 162 by threaded engagement means. The image pickup unit 163 is arranged such that the imaging lens 166, a CCD 167, an electronic circuit board 168, an optical communication element 169, and a battery 170 for operating the CCD 167 and the like are received within the frame 165 of a hermetic structure. The interior of the frame 165 is brought to a vacuum. Moreover, an optical communication element 171 for communicating with the optical communication element 169 is also arranged on the outside of the frame 165 opposed against the optical communication element 169. The optical communication element 171 is connected to the cable 172. With this arrangement, the electronic scope 101 has mechanisms similar to those illustrated in FIG. 25.

In the endoscope system 31 illustrated in FIG. 1, the outside mounted camera 33 is arranged such that the image pickup unit 68 can be separated and be taken out. However, in the outside mounted camera 33' in an endoscope system 31' illustrated in FIG. 27, the outside mounted camera 33 is not separated, but is brought to an adiabatic structure so that the outside mounted camera 33 can be processed in autoclave. An imaging lens 55 and a CCD 56 are mounted on a frame 61 within the camera head body 33a of the outside mounted camera 33'. Further, a pair of printed circuit boards 57 and 58 are mounted through the spacer 60.

The printed boards 57 and 58 on which the CCD 56 and the electronic part 59 are packaged or mounted are received within a heat insulator 64 in which a material having a heat resistance such as a high-function engineering plastic material or the like is brought to a foamed plastic material and is formed into a box. The printed boards 57 and 58 are of a structure so as to prevent heat or thermal conduction into the thermal insulator 64 from the outside as far as possible by the insulator 64 when thermal processing in sterilization of the CCD 56 and the electronic part 59. That is, the printed boards 57 and 58 are of a heat insulating structure so as to be cable of preventing temperature rise within the thermal insulator 64. The circumference of the thermal insulator 64 is covered by a mold element 65 formed into a box by a high-function engineering plastic material or the like.

In the present embodiment, an irregular portion is formed on the outer surface of the heat or thermal insulator 64. A contact area with respect to the mold element 65 serving as an outside housing is made small as far as possible so that heat from the outside mold element 65 is not transmitted to the thermal insulator 64 as far as possible.

Figures 28A, 28B:
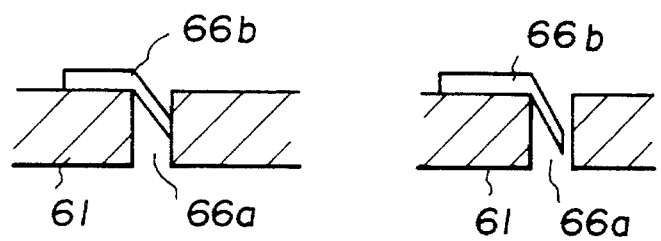
FIGS. 28a and 28b are views showing a mechanism for regulating internal pressure.

Further, in the present embodiment, a ventilating bore 66a for regulating an internal pressure is provided in the frame 61. The ventilating bore 66a is of a structure opened and closed by a valve 66b. That is, in a case where a pressure difference between the inside and the outside is not so large, the ventilating bore 66a is maintained to a condition closed by the valve 66b as shown in FIG. 28a. The valve 66b is opened as shown in FIG. 28b as the internal pressure is raised considerably more than the external or outside pressure.

Figure 29:
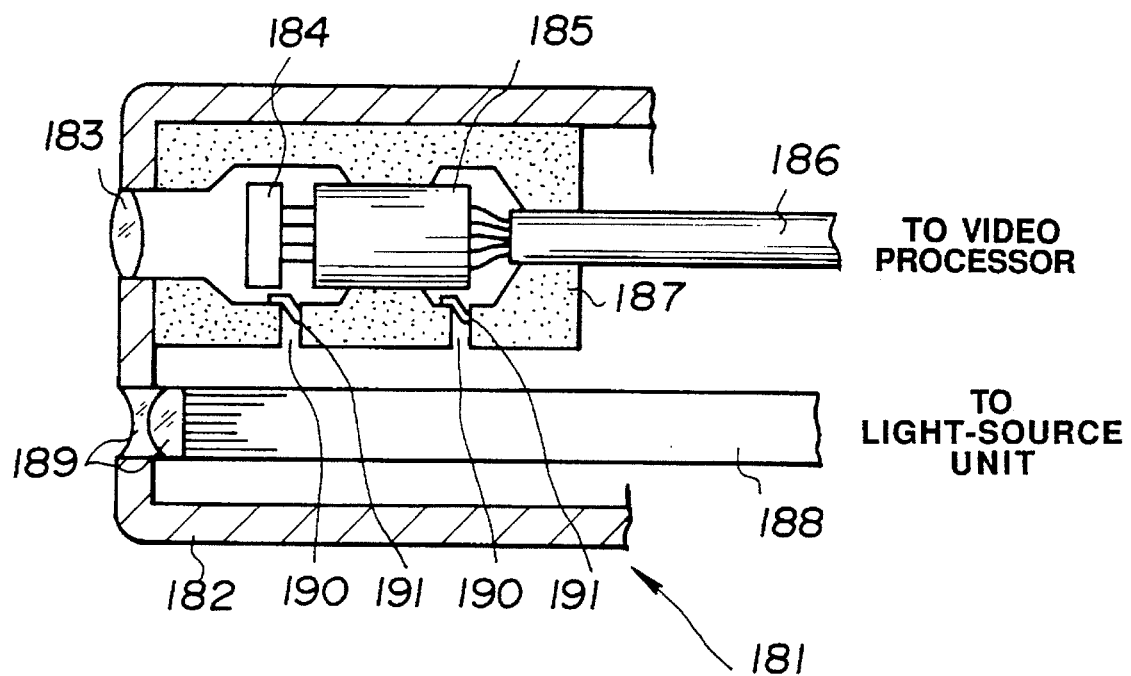
FIG. 29 is an arrangement view showing a forward end portion of an electronic scope provided with a mechanism for regulating internal pressure.

A forward end portion 181 of an electronic scope provided with a regulating mechanism for the internal pressure is illustrated in FIG. 29.

An objective lens 183 is mounted on an observation window provided in the outside frame 182. The CCD 184 has a photoelectric transfer surface which is arranged at the focus surface of the objective lens 183. The CCD 184 is of a structure integrated with the hybrid substrate 185. A signal photoelectrically transferred by the CCD 184 passes through the hybrid substrate 185, and passes through a transmitting cable 186 connected to the hybrid substrate 185, and is inputted into a video processor (not shown).

The video processor transfers an output signal from the CCD 184 into a standard image signal. An adiabatic element 187 is received within the outside frame 182. By the adiabatic element 187, the CCD 184 and the hybrid substrate 185 are covered. The adiabatic element 187 is formed by, for example, polystyrene foam. Head or thermal conductivity of the polystyrene foam is equal to or less than 1/10 as compared with the outside frame 182. A material low in thermal conductivity may be used in place of the polystyrene foam.

A light guide 188 for transmitting an illuminating light is inserted in the outside frame 182. An end of the light guide 188 adjacent to the hand is connected to a light-source unit (not shown). The illuminating light from the light-source unit is transmitted, further passes through the illuminating lens 189 from the forward end surface, and is projected forwardly toward the subject.

Also in the present embodiment, the CCD 184 and the hybrid substrate 185 are covered by the heat insulating element 187. Furthermore, the heat insulating element 187 is provided with a ventilating bore 190 and a valve 191 for regulating an internal pressure. When the internal pressure rises, the valve 191 is opened.

Figure 30:
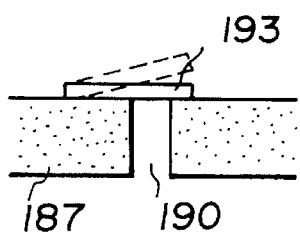
FIG. 30 is a view showing a mechanism for regulating internal pressure.
Figure 27:
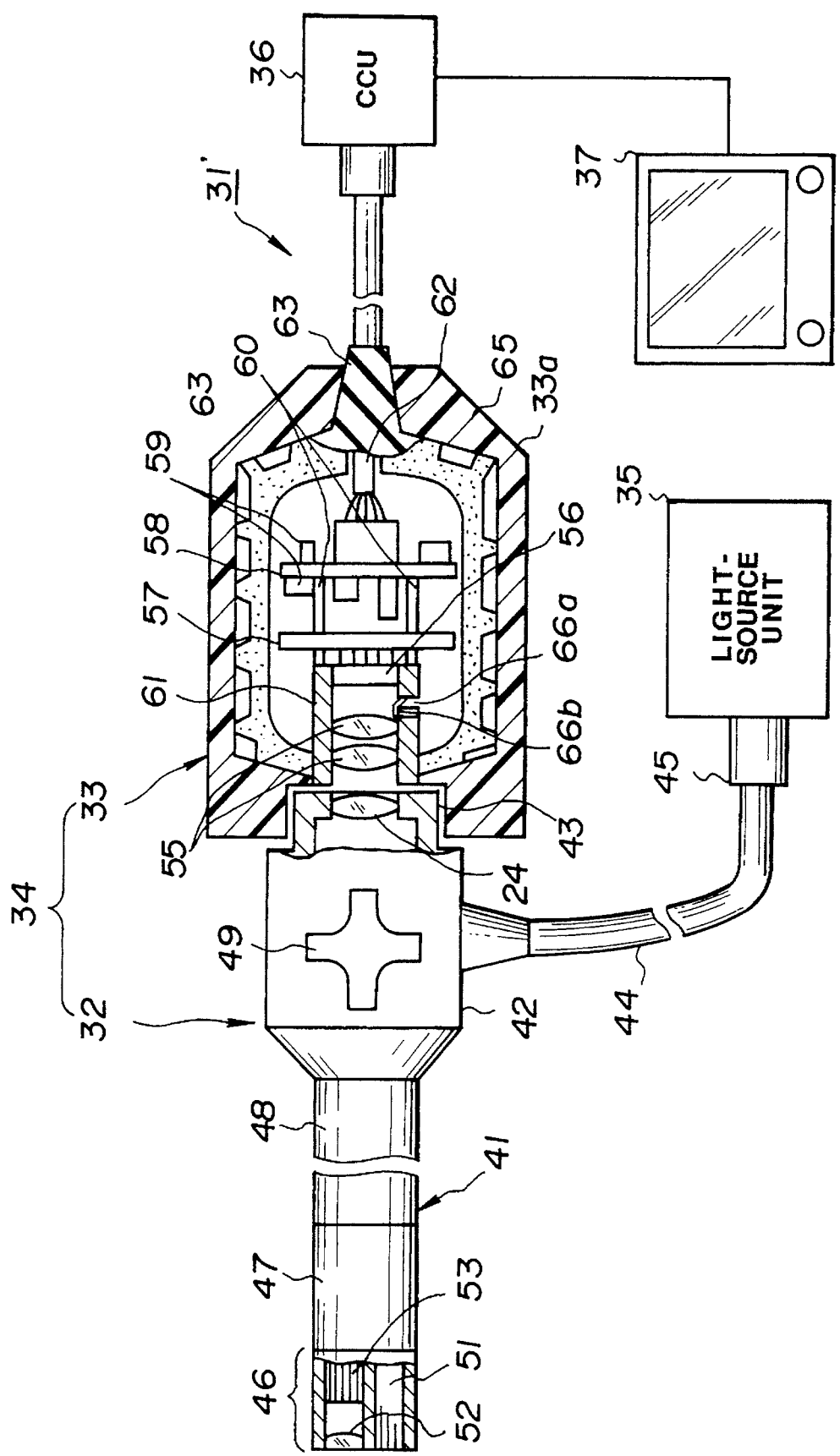
FIG. 27 is an arrangement view showing an endoscope system provided with a camera outside mounted endoscope having an adiabatic structure.

In connection with the above, as shown in FIG. 30, the arrangement may be such that a valve 193 using a shape memory alloy is mounted on the ventilating bore 190, and valve 193 is bent by heat at autoclave processing as indicated by the broken lines, thereby opening the ventilating bore 190.

Figure 31:
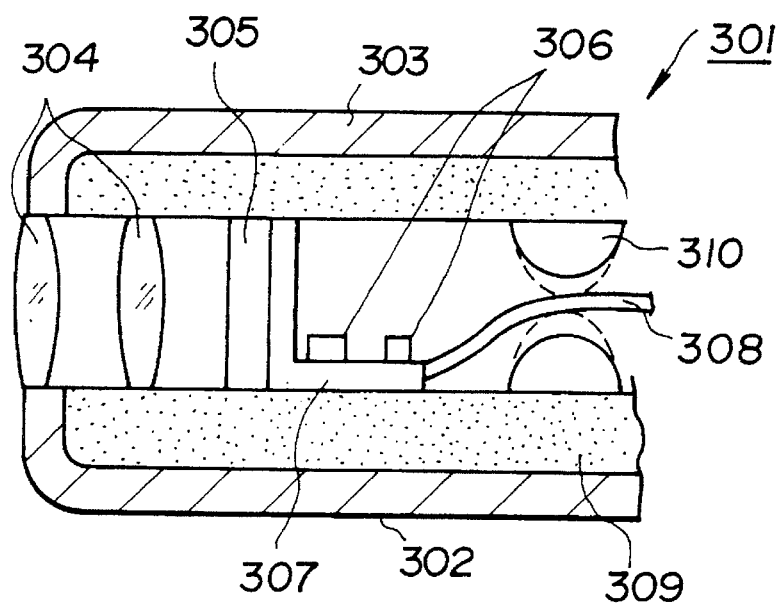
FIG. 31 is an arrangement view showing a forward end portion of an electronic scope mirror provided with a mechanism for preventing steam from invading.

In the electronic scope 301 illustrated in FIG. 31, an objective lens 304 is mounted on an observation window which is provided on the armored frame 303 forming the forward end portion 302 of the inserting section, and a CCD 305 is arranged in rear of the objective lens 304. A substrate 307 on which the circuit component or part 306 is packaged or mounted is arranged on the side of the rear surface of the CCD 305. A signal cable 308 is connected to the substrate 307, and extends toward a rearward operating section (not shown). A heat insulating material 309 is arranged cylindrically on the circumference of the CCD 305 and the like. A thermal expanding element 310 in the form of a doughnut is arranged at a location in rear of the substrate 307.

The thermal expanding element 310 opens such that, normally, front and rear portions of the thermal expanding element 310 communicate with each other as indicated by the solid lines. At autoclave processing, the thermal expanding element 310 is thermally expanded so that both sides of the thermal expanding element 310 are isolated or cut off as indicated by dotted lines, thereby preventing steam from invading toward the CCD 305 which is arranged in front of the thermal expanding element 310.

With the above arrangement, it is possible to effectively prevent characteristics of the CCD 305 and the like from being deteriorated by moisture at autoclave processing.

An autoclave unit 401 provided with a cleaning function on the autoclave unit for processing in autoclave the above-described scope and the like will next be described.

Figure 32:
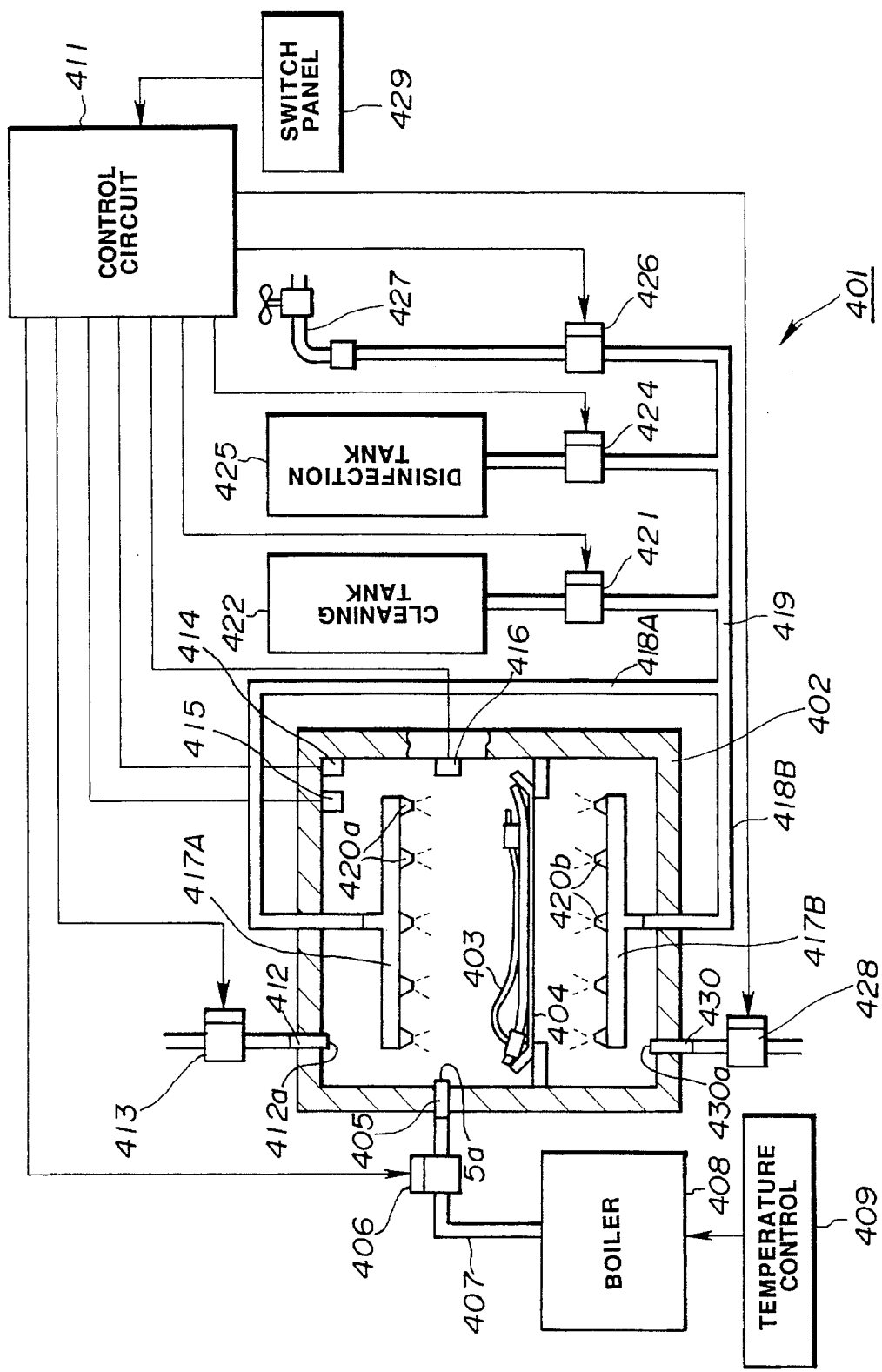
FIGS. 32 and 33 are views showing a first embodiment of an autoclave unit, FIG. 32 being a view showing the entire arrangement of the autoclave unit.

As shown in FIG. 32, the autoclave unit 401 is formed with an autoclave unit body 402 by a container or vessel withstanding high pressure and temperature. Medical instruments such as an endoscope 403 and the like can be received within the autoclave unit body 402.

The endoscope 403 is received such that an endoscope receiving table 404 is engaged with a projection on an inner wall surface of the autoclave unit body 402 under a condition mounted on the endoscope receiving table 404 formed by, for example, a net-like tray. A base element 45 serving as a steam injection portion 405a into which steam is injected is fixedly mounted on a bore extending through the wall of the autoclave unit body 402. The base element 405 is connected to a boiler 408 for generating steam, through a pipe 407 on which a first control valve 406 is provided, at a location on the outside of the autoclave unit body 402.

The boiler 408 is controlled by a temperature control circuit 409 such that a temperature of the steam generated within the boiler is made constant, and a relief valve and the like (not shown) are provided such that pressure is not brought to a value equal to or more than a permitted pressure. The steam having a constant temperature can be supplied to the autoclave unit body 402.

The first control valve 406 is formed by an electromagnetic valve. Opening and closing of the first control valve 406 are controlled by a drive signal from the control circuit 411. For example, under a condition being opened, a condition is brought to a condition flowing steam from the boiler 408. Steam is injected from the steam injection port 405a to the inside of the autoclave unit body 402.

Moreover, a base element 412 brought to the steam discharge port 412a for discharging the steam is fixedly mounted on a bore extending through the wall of the autoclave unit 402 at, for example, an upper portion. The base element 412 opens outside at a location on the outside of the autoclave unit body 402 through the second control valve 413. Opening and closing of the second control valve 413 are controlled by a control circuit 411 such that the inside air is discharged before the steam is injected toward the inside of the autoclave unit body 402 from the steam injection port 405a.

A temperature of the steam injected into the inside of the autoclave unit body 402 is detected by a temperature sensor 414. An output from the temperature sensor 414 is inputted into a control circuit 411. Moreover, the internal pressure within the autoclave unit body 402 is detected by the pressure sensor 415. An output from the pressure sensor 415 is inputted into a control circuit 411. With this information used, the control circuit 411 retains a condition of the steam of high temperature and high pressure with respect to medical instruments such as an endoscope 403 and the like received within the autoclave unit body 402, to execute sterilization processing, that is, autoclave processing.

In connection with the above, the autoclave processing is executed upon confirmation that a door of the control circuit 411 is closed, depending upon whether or not the microswitch 416 is brought to an ON condition.

Further, the autoclave unit 401 has a cleaning and disinfection function in addition to the autoclave processing, and can execute cleaning and disinfection processing with respect to the medical instruments such as the endoscope 403 and the like which are received within the autoclave unit body 402.

A pair of nozzle elements 417A and 417B for jetting fluid have respective proximal ends thereof which are fixedly mounted on a bore which extends through upper and lower wall portions, for example, of the autoclave unit body 402. These nozzle elements 417A and 417B are connected to one end of respective liquid feeding lines 418A and 418B at a location outside the autoclave unit body 402. Portions adjacent to the other ends of the respective liquid feeding lines 418A and 418B are brought to a common line 19. The nozzle elements 417A and 417B have a plurality of jetting nozzle openings 420a, 420a, . . . and 420b, 420b at a line portion in the form of a line.

The jetting nozzle openings 420a, 420a, . . . in the nozzle element 417A are directed downwardly, while jetting nozzle openings 420b, 420b, . . . in the nozzle element 417B are directed upwardly. Cleaning liquid or disinfection liquid are poured from below and from above with respect to the medical instruments such as the endoscope 403 and the like arranged between the nozzle element 417A and the nozzle element 417B, so as to be able to execute cleaning and disinfection.

The common line 419 is connected to the cleaning tank 422 through the third control valve 421, and is connected to the disinfection liquid tank 425 through the fourth control valve 424. The common line 419 further passes through the fifth control valve 426, and has an end thereof connected to a faucet of a water pipe (water pipe plug) 427.

These third, fourth and fifth control valves 421, 423 and 426 are controlled in their opening and closing by the control circuit 411. Further, a base element 430 forming a liquid discharge port 430a for discharging liquid is fixedly mounted on a bore which extends through the lower wall portion, for example, of the autoclave unit body 402. The base element 430 opens to the outside air through a sixth control valve 428 at a location outside the autoclave unit body 402. Opening and closing of the sixth control valve 428 are also controlled by the control circuit 411.

Figure 33:
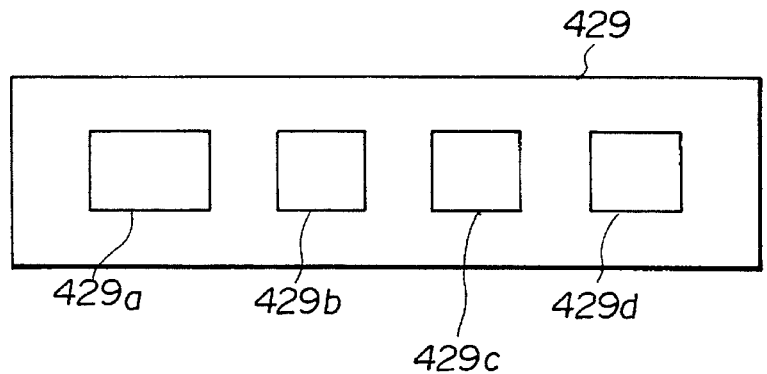

A switch panel 429, for example, as shown in FIG. 33 is connected to the control circuit 411. Operation is executed in which an automatic autoclave switch 429a serving as a selective switch, a cleaning switch 429b, a disinfection switch 429c, and an autoclave switch (sterilization switch) 429d in the switch panel 429 are depressed, whereby functions had by the autoclave unit 401 are used to enable operations to be executed under various modes.

Figure 35:
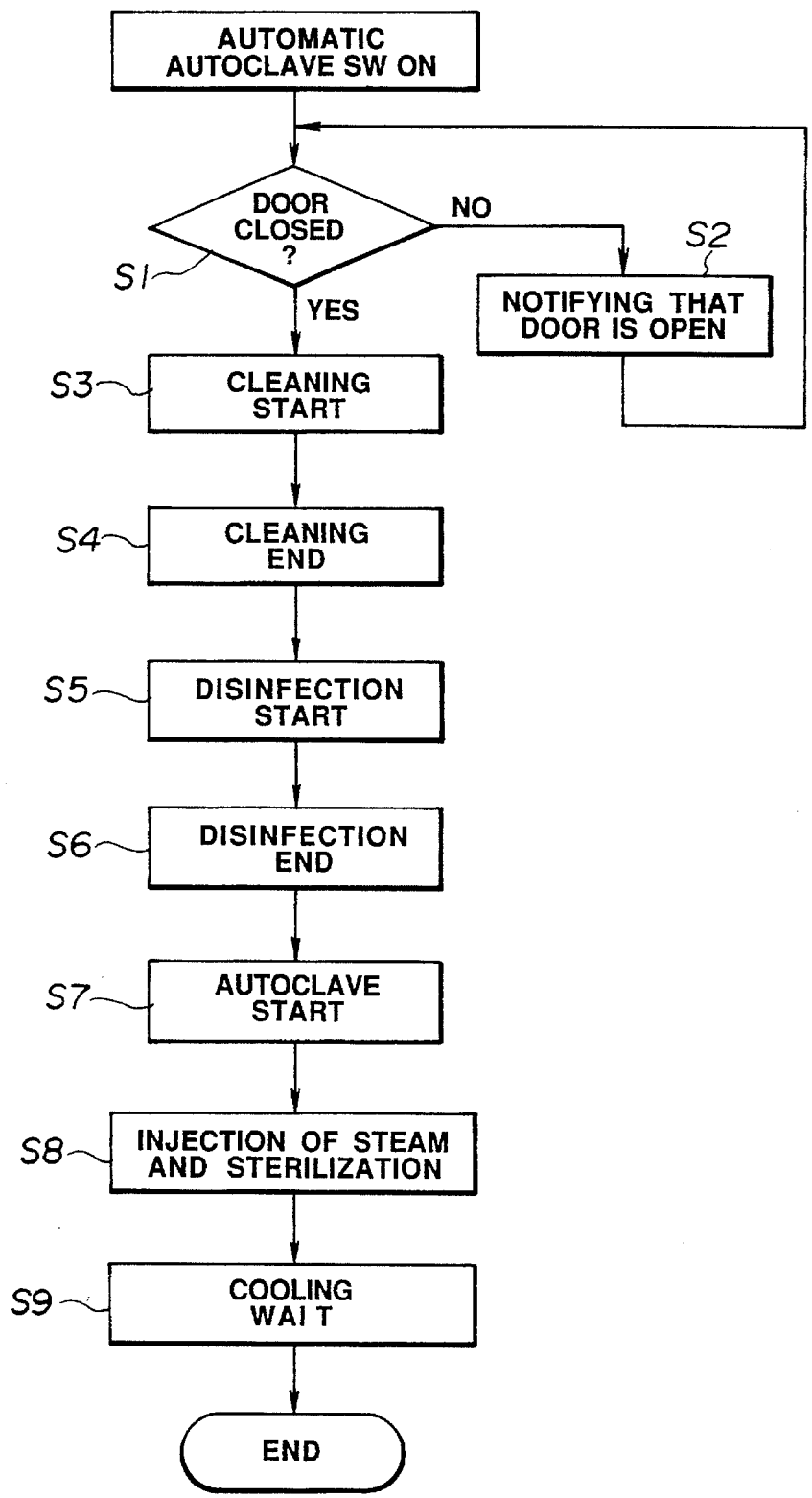
FIG. 35 is a flow chart showing an example of operational contents of an autoclave unit.

Specifically, in a case where the automatic autoclave switch 429a is operated, various processings such as cleaning, disinfection and sterilization are successively executed with time sharing as shown in FIG. 35. In a case where the autoclave switch 29d is operated, processing of cleaning and disinfection are not executed, but processing of sterilization is executed. Furthermore, when the cleaning switch 29b or the disinfection switch 29c is operated, cleaning or disinfection processing is executed.

Figure 34:
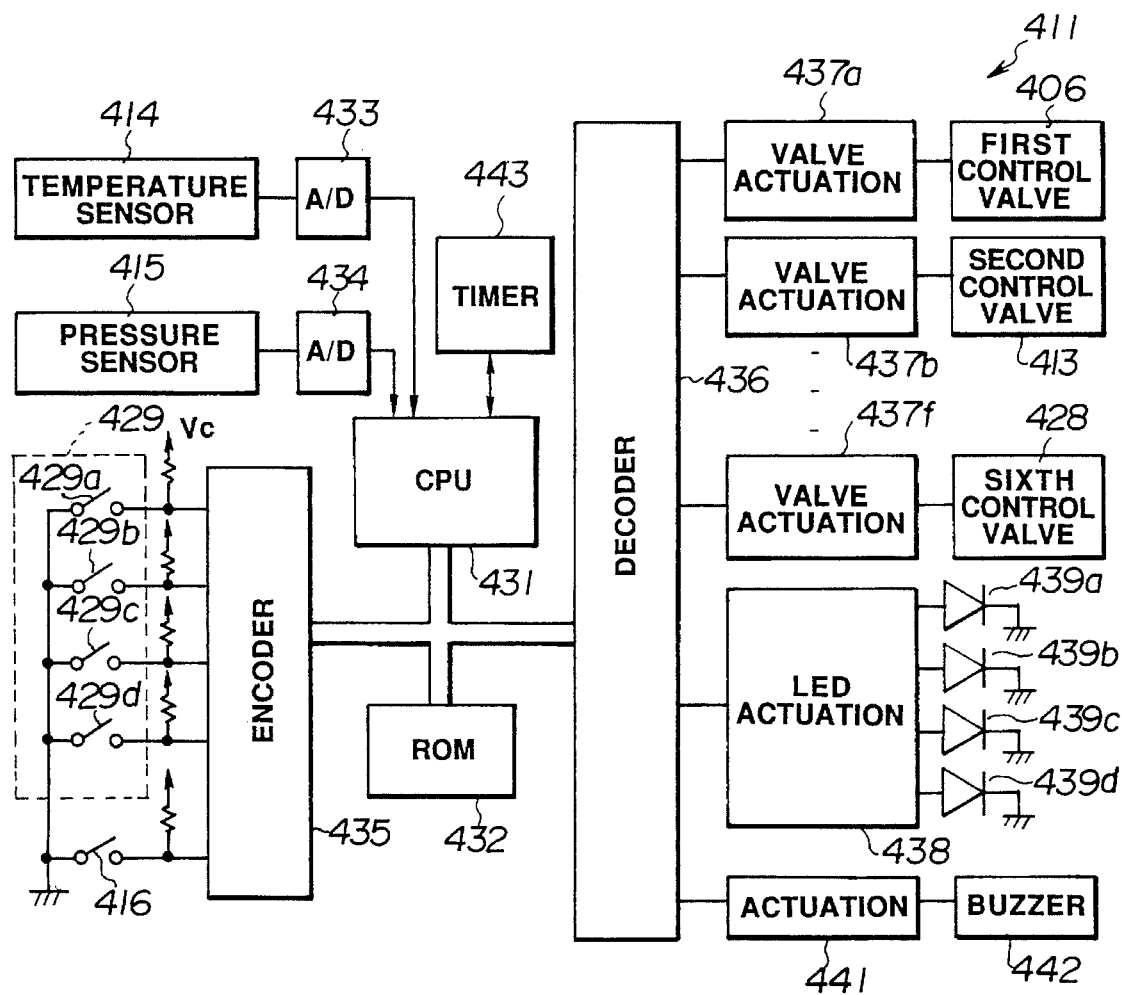
FIG. 34 is a block diagram showing an arrangement of a control circuit.

A schematic arrangement of the control circuit 411 for controlling these processing operations is next shown in FIG. 34. A CPU 431 for executing whole control is connected to a ROM 432 which stores therein program data and the like of various processing operations through a bus line. The CPU 431 refers to the stored contents of the ROM 432 to execute control so as to execute various processing operations.

A temperature detecting signal from the temperature sensor 414 is converted into a digital signal by an A/D converter 433 which converts the temperature detecting signal into serial data, for example, and subsequently, is inputted into the CPU 431 through a serial line. Furthermore, a pressure detecting signal from the pressure sensor 415 is converted into a digital signal by an A/D converter 434 which converts the pressure detecting signal into serial data, for example, to output the same and subsequently, is inputted into the CPU 431 through a serial line.

Moreover, an automatic autoclave switch 429a, a cleaning switch 429b, a disinfection switch 429c and an autoclave switch 429d in the switch panel 429 are connected to the CPU 431 through the encoder 435. These switches are connected to the CPU 431 through I/O ports having their numbers different from each other. The CPU 431 monitors whether or not these I/O ports are brought to an L-level. In a case where the I/O ports are brought to the L-level, the CPU 431 executes such a control as to execute corresponding processing.

Further, the CPU 431 can control opening and closing of a first control valve 406, a second control valve 413, . . . , a sixth control valve 428 through valve drive circuits 437a, 437b, . . . , 437f which are connected to I/O ports different from the abovedescribed numbers, through a decoder 436. An LED drive circuit 438 is connected to the decoder 436. The LED drive circuit 438 sets four (4) LEDs 439a, . . . , 439d to light-emitting conditions correspondingly to selective operation of the four (4) switches on the switch panel 429. An operator can recognize which switch is selected.

Furthermore, a (buzzer) drive circuit 441 is connected to the decoder 436. In a case where an optional switch on the switch panel 429 is operated under a condition that the microswitch 416 is turned OFF, that is, under a condition that the door is open, the buzzer 442 is operated to execute warning. In this connection, the microswitch 416 for detecting opening and closing of the door is connected to the CPU 431 through the encoder 435.

Moreover, in a case where various processings are executed, the CPU 431 controls operations of the control valve and the like by time sharing so as to execute various processings, by a signal outputted from the timer 443 at the time the timer 443 starts up and set time elapses from time of operation or actuation.

With the autoclave unit 401 arranged as described above, when the automatic autoclave switch 429a, for example, is operated, the CPU 431 executes controlling so as to execute processing illustrated in FIG. 35.

By the operation of the switch 429a, judgment on whether or not the door is closed is first executed depending upon whether or not the microswitch 416 is turned ON, as indicated by a step S1. When the microswitch 416 is not turned ON, it is notified by the buzzer 442 that the door is open, as indicated by a step S2. The program is returned to a step S1.

On the other hand, when the microswitch 416 is turned ON, the timer 443 starts up, and cleaning processing starts as indicated by the step S3. When the cleaning processing starts, the CPU 431 outputs a signal driving the valve drive circuit 437c such that the third control valve 421 is turned from closing to opening, and outputs a signal driving the valve drive circuit 437e such that the fifth control valve 426 is turned from closing to opening. Then, cleaning liquid within the cleaning tank 422 and water in the water pipe are jetted through the jetting nozzle openings 420a, 420a, . . . in the nozzle element 417A, the jetting nozzle openings 420a, 420a, . . . , and 420b, 420b in the nozzle element 417B, so that the endoscope 403 is cleaned.

When time set beforehand elapses from start of cleaning, a signal representing that time elapses is inputted from the timer 443. Accordingly, the CPU 431 outputs a signal to the valve drive circuits 437c and 437e such that the third control valve 421 and the fifth control valve 426 are switched from opening to closing. Further, the sixth control valve 428 is open so that cleaning water is discharged from the liquid discharge opening 427a. After a period of time discharge is completed, the sixth control valve 428 is closed to finish or complete cleaning processing as illustrated in a step S4.

In connection with the above, the sixth control valve 428 may be open from start of the cleaning always to discharge the cleaning liquid during the cleaning operation from the liquid discharge opening 427a. Further, cleaning may be executed only by the cleaning liquid and, subsequently, the cleaning liquid may be washed away by water in the water pipe.

Disinfection processing subsequently starts as indicated by a step S5. When the disinfection processing starts, the timer 443 starts up, and the CPU 431 outputs such a signal that the valve drive circuit 437d is driven so that the fourth control valve 424 is switched from closing to opening. Then, disinfection liquid within the disinfection tank 425 is jetted through the jetting nozzle openings 420a, 420a, . . . in the nozzle element 417A and the jetting nozzle openings 420a, 420a, . . . and 420b, 420b, . . . in the nozzle element 417B so that the endoscope 403 is disinfected.

When time set beforehand elapses from start-up of disinfection, a signal representing that time elapses is inputted from the timer 443. Accordingly, the CPU 431 outputs a signal of the valve drive circuit 437d such that the fourth control valve 424 is switched from opening to closing. The valve drive circuit 437e is driven such that the fifth control valve 426 is switched from closing to opening. Processing is executed such that the disinfection liquid is washed away by the water in the water pipe.

After the processing washing away by the water in the water pipe, the fifth control valve 426 is closed. Subsequently, the sixth control valve 428 is open to discharge the disinfection liquid and the water in the water pipe from the liquid discharge opening 427a. After time in which discharge has been completed, the sixth control valve 428 is closed so that the disinfection processing is completed as indicated in the step S6.

In connection with the above, the arrangement may be such that the sixth control valve 428 is open from start-up of the disinfection to always discharge the disinfection liquid during the disinfection operation from the liquid discharge opening 427a, and to always discharge the water in the water pipe from the liquid discharge opening 427a, so that the sixth control valve 428 is closed at the time the disinfection processing has been completed.

Autoclave processing subsequently starts up as indicated in a step S7. When the autoclave processing starts up, the CPU 431 outputs a signal driving the valve drive circuit 437a such that the first control valve 406 is switched from closing to opening. Then, steam within the boiler 408 starts to be injected into the autoclave unit body 402 through the steam injection opening.

Then, the CPU 431 monitors an output from the temperature sensor 414 and an output from the pressure sensor 415, and starts the timer 443 at time a temperature and a pressure suitable for sterilization are reached. The CPU 431 control the valve drive circuit 437a such that the first control valve 406 is switched from opening to closing, and processes in sterilization the endoscope 403. That is, as indicated in a step S8, injection of steam and sterilization processing are executed. The CPU 431 monitors the output from the temperature sensor 414 and the output from the pressure sensor 415. When a temperature and a pressure within the body decrease, the CPU 431 control the first control valve 406 so as to be opened, and retaining is executed to a set temperature and a set pressure so that sterilization processing is executed.

When the set time has elapsed, a signal representing that time has been elapsed is inputted from the timer 443. Accordingly, the CPU 431 outputs a signal to the valve drive circuit 437b such that the second control valve 4313 is switched from closing to opening, to discharge steam from the discharge opening 412a. Further, in order to prevent a burn or the like from occurring during operation, the wait required for cooling the autoclave unit body 402 and the inside endoscope 403 is executed as indicated in a step S9, or it is confirmed that the output from the temperature sensor 414 is reduced to a temperature close to the normal or ordinary temperature. Then, the CPU 31 rings the buzzer 442 through the drive circuit 441, to inform completion.

In connection with the above, FIG. 35 shows the processing contents in a case where the automatic autoclave switch 429a is operated. In a case where other switches are operated, processing of a portion in FIG. 35 is executed. For example, when the cleaning switch 429b is turned ON, processings from the step S1 to the step S4 in FIG. 35 are executed. Furthermore, when the disinfection switch 429c is turned ON, processings in the steps S1 and S2 and in the steps S5 and S6 in FIG. 35 are executed. When the autoclave switch 429d is further turned ON, the processings in the steps S1 and S2 and in the steps S7 to S9 in FIG. 35 are executed.

The unit 401 has cleaning and disinfection functions in addition to the autoclave function, and cleaning and disinfection can be executed before the autoclave processing. Accordingly, even in a case where a condition is a condition insufficient in cleaning or the like, and even in a case where cleaning is not executed, operation of the automatic autoclave switch enables the cleaning or the like to be executed before the autoclave processing.

Accordingly, it effectively prevents the disinfection processing from being executed under a condition where dirt or the like are adhered to medical instruments which are received within the autoclave unit.

Further, this apparatus can execute only cleaning processing or only disinfection processing. Accordingly, it is possible to reduce an occupied area less than a case where various elements are provided separately. In this connection, the arrangement may be such that the autoclave unit is provided with a cleaning function in addition to a function executing the autoclave processing.

An autoclave unit will next be described in which a condition in a case where autoclave processing is executed in accordance with a resistance of an endoscope and the like processed in autoclave is set variably.

Figures 36, 37:
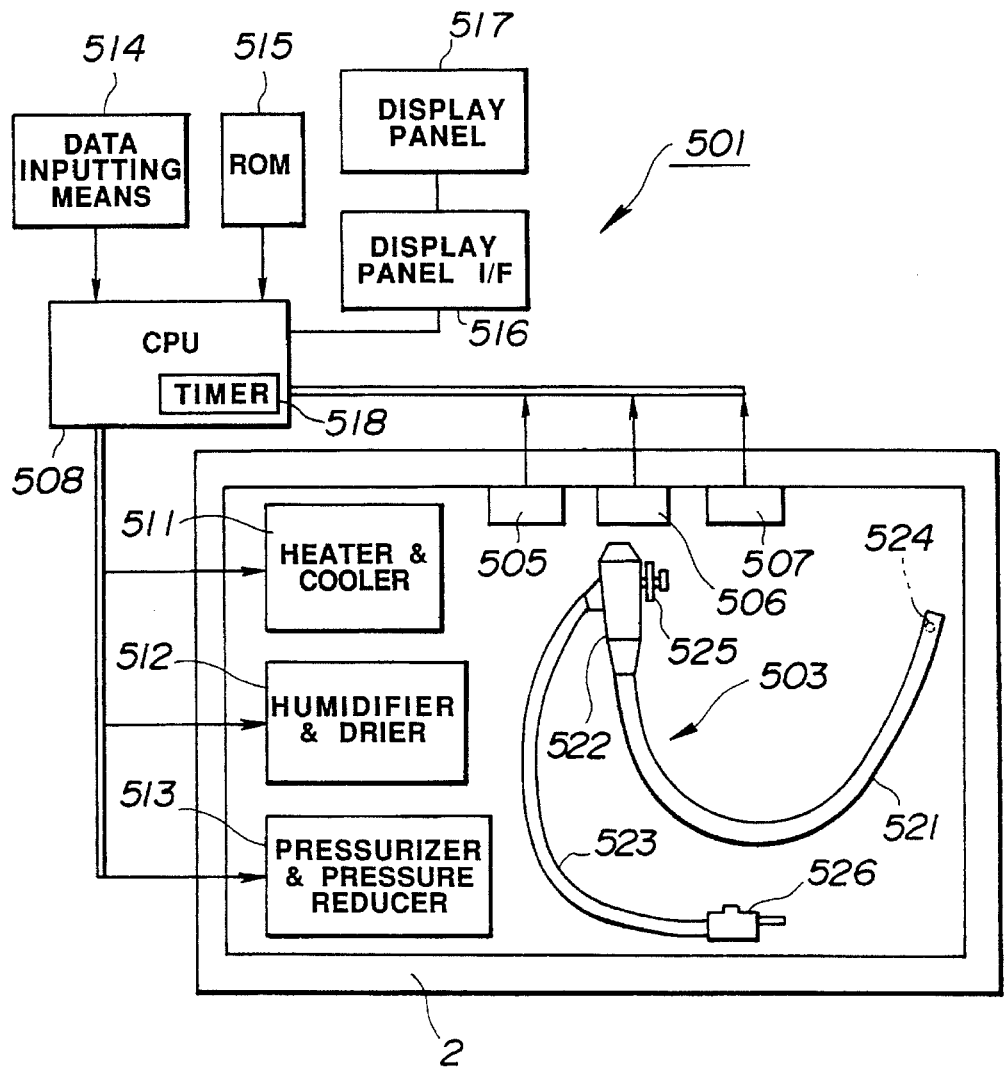
FIGS. 36 through 38 are views showing a second embodiment of the autoclave unit, FIG. 35 being an arrangement view showing the autoclave unit according to the second embodiment of the invention.

As shown in FIG. 36, an autoclave unit 501 in accordance with the second embodiment is arranged such that an autoclave unit body (or an autoclave tank) 502 is formed by a receiving container withstanding a high pressure and a high temperature. A door provided on a front surface of the autoclave unit body 502 so as to be movable angularly is opened so that medical instruments such as an electronic scope 503 and the like can be received.

A temperature sensor 505 for detecting a temperature within the autoclave unit body 502, and a humidity sensor 506 for detecting a humidity within the autoclave unit body 502, and a pressure sensor 507 for detecting a pressure within the autoclave unit body 502 are built within the autoclave unit body 502. Outputs therefrom are inputted to the CPU 508 through input ports. A heater and cooler 511 provided with a function of heating and cooling for executing maintenance to a set temperature, a humidifier and dryer 512 provided with a function of humidifying and drying for executing maintenance to a set humidity, and a presser and reducer 513 provided with a function of pressurizing and pressure-reducing for executing maintenance to a set pressure are connected to the output and input port of the CPU 508. The heater and cooler 511, the humidifier and dryer 512 and the pressure and pressure-reducer 513 are arranged such that values of a temperature, a humidity and a pressure at executing autoclave processing by a command from the CPU 508 are determined.

Data inputting means 514 formed by a key board or the like is connected to the CPU 508 so that data such as a kind or type of medical instruments associated with the endoscope and the like can be inputted from the data inputting means 514. Further, the CPU 508 is connected to a ROM 515 which stores therein data such as the kind of medical instruments associated with the endoscope and the like and constant data of the autoclave processing condition corresponding to the data of the kind and the like.

In a case where the autoclave processing is executed, the CPU 508 reads out the stored contents in the ROM 515, to display the autoclave processing condition contents corresponding to the kind of the medical instruments on a display panel 517 through a display panel I/F 516 in the form of a menu, as illustrated in FIG. 37. When the kind of the medical instruments are inputted by the data inputting means 514, the corresponding autoclave processing condition contents are set to a condition being autoclave by the autoclave unit 501.

Furthermore, a program executing the autoclave processing sequentially is written into the ROM 515. The CPU 508 controls operations of the various constitutional elements so that the autoclave processing is executed in accordance with the program contents.

Moreover, in a case where a user executes the autoclave processing, the medical instruments associated with the endoscope processed in autoclave by the data inputting means 514 are selected, whereby the autoclave processing condition can be set by a default condition (established condition), and the setting contents of the autoclave processing condition can also be changed or altered.

Further, in a case where the CPU 508 executes the autoclave processing, the CPU 508 starts up a built-in timer 518. When set time elapses from time coincident with the set condition, operations of the heater and cooler 511 and the like are controlled such that an elapse signal outputted from the timer 518 is referred to complete the autoclave processing.

In the present embodiment, the CPU 508 fetches the output from the temperature sensor 505, the humidity sensor 506, and the pressure sensor 507, and transmits the outputs to the heater and cooler 511, the humidifier and dryer 512, and the presser and reducer 513, to control so as to execute the autoclave processing by the feedback control so as to maintain the set conditions.

The electronic scope 503 processed in autoclave by the autoclave unit 501 has an elongated inserting section 521, an operating section 522 provided at a rearward end of the inserting section 521, and a universal cable 523 extending to the outside from the operating section 522. A CCD 524 serving as an image pickup element is built in the forward end portion of the inserting section 521. Furthermore, a curved knob 525 at the operating section 522 is operated so as to be moved angularly, whereby it is possible to operate in curvature the curved section which is arranged adjacent to the forward end portion. Moreover, a connector 526 is provided at the forward end of the universal cable 523, and can be connected to a video processor (not shown).

Figure 38:
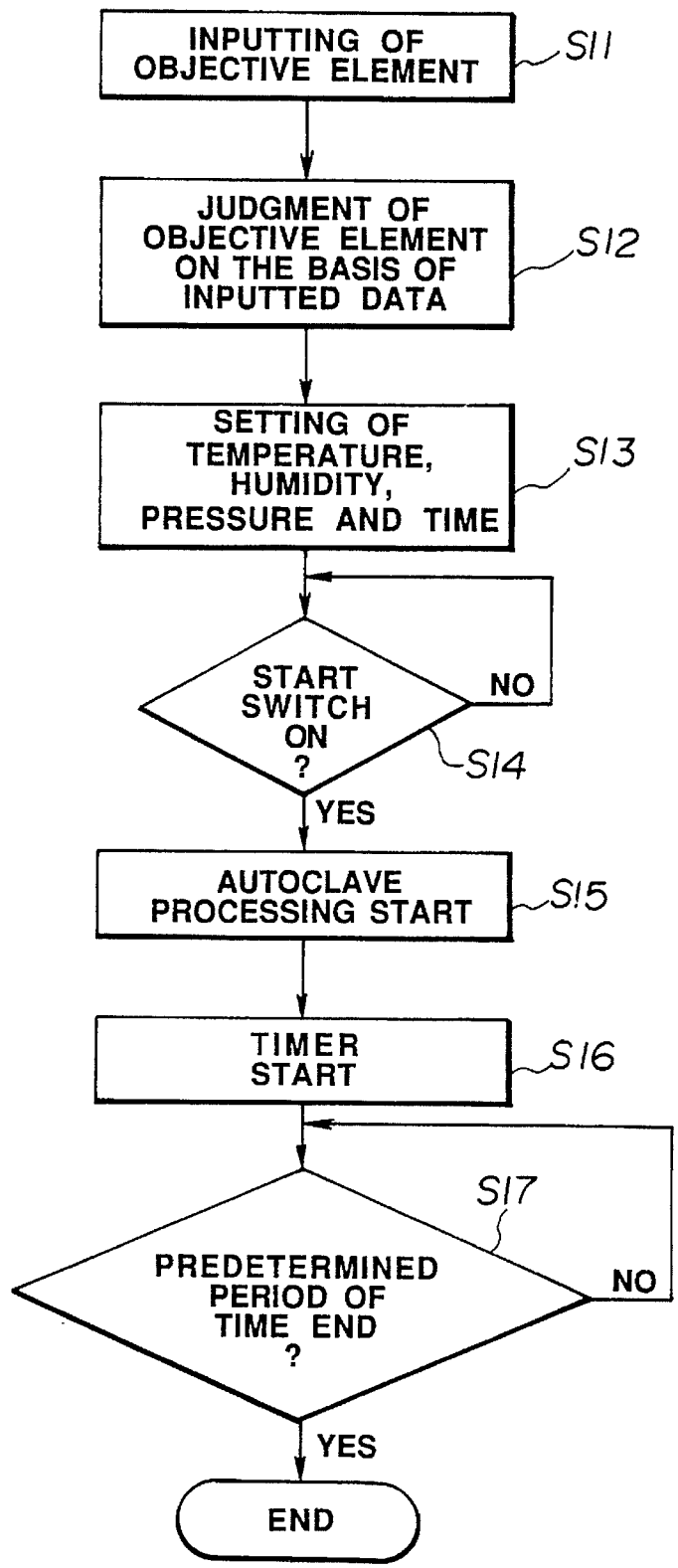

Function of the autoclave unit 501 according to the present embodiment will next be described. When the power source switch of the autoclave unit 501 is turned ON, the CPU 508 starts up in accordance with the program contents of the ROM 515, and executes processing urging inputting to a subject element as indicated in a step 11 in FIG. 38. In this case, the CPU 508 displays the kinds of the endoscope associated instruments registered on the ROM 515 as illustrated in FIG. 36, and the contents in terms of default values of setting conditions of the autoclave processing corresponding to the various kinds, on the display panel 517, and further executes display as to what instruments are selected.

For example, when the number 1 is inputted from the data inputting means 514 in a case where the electronic scope 503 is selected, the CPU 508 judges that the number is the electronic scope 503, as indicated in the step S12. Further, when "YES" is responded with respect to a question as to whether or not established-value conditions are satisfied, conditions of the autoclave processing are set to a temperature, a humidity, a pressure and time of set conditions corresponding to the electronic scope illustrated in FIG. 37 (step S13).

When "NO" is answered to a question as to whether or not the established-value conditions are satisfied, whereby it is possible to set the condition of the autoclave processing by setting conditions different from the established-value condition. In this connection, if it is responded by the number 5 in a case where the instruments are selected, it is possible to execute autoclave processing with respect to instruments other than the endoscope associated instruments which are already registered, and it is also possible to register the kinds and the setting contents of the instruments.

When the processing is completed through step S13, a condition is brought to a condition awaiting inputting of a start switch as indicated in a step S14. When the start switch is turned ON, the autoclave processing starts as indicated in a step S15, and heating and the like of the heater and cooler 511 and the like are brought to an operating condition so as to coincide with the selected conditions. It is monitored by the CPU 508 whether the operating condition is coincident with temperature or the like of the set condition. When the set condition is reached, the autoclave processing under the set condition substantially starts (that is, sterilization processing operation within steam of set high temperature and high pressure starts), and the timer 518 starts up as indicated in a step S16.

When predetermined or constant time elapses, the timer 518 outputs an elapsing signal representing to the CPU 508 that the predetermined or constant time has elapsed, whereby the CPU 508 detects that set time has elapsed, as indicated in a step S17, to output a command so as to stop operation of the heater and cooler 511 and the like. Accordingly, the condition within the autoclave unit body 502 approximates a condition under a normal temperature and a normal pressure with an elapse of time. Thus, the autoclave processing is completed.

According to the autoclave unit body 501 according to the second embodiment, setting can be selectively done by the menu so as to be able to execute autoclave processing under a processing condition in accordance with the instruments processed in autoclave. Accordingly, in a case of instruments low in heat resistance, for example, time is set long at a low temperature, in consideration of a heat resistance thereof so that it is possible to execute autoclave processing under conditions with heat resistance or the like considered.

In connection with the above, setting positions of the dial are variably set in place of the menu, whereby setting may be made so as to execute the autoclave processing under the processing condition in accordance with the instruments processed in autoclave.

Figure 39:
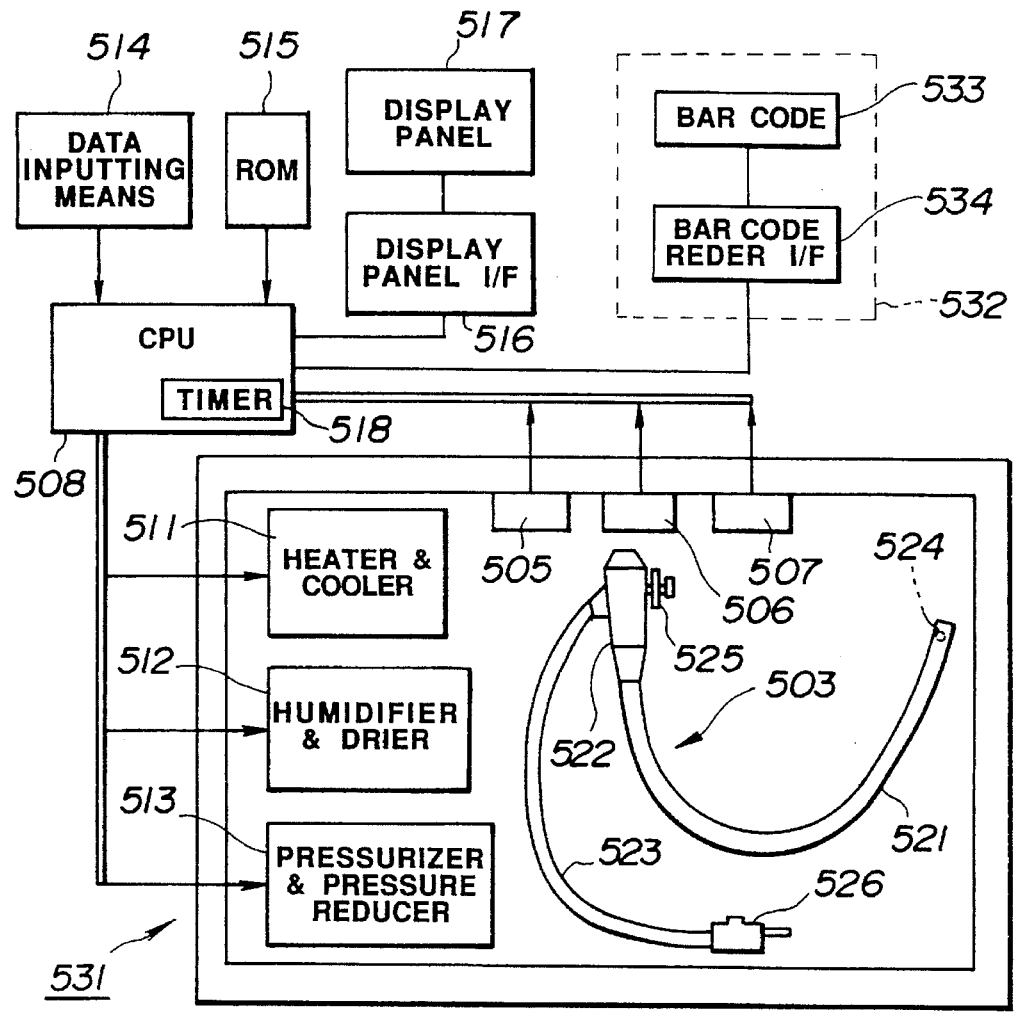
FIG. 39 is an arrangement view showing an autoclave unit according to a third embodiment of the invention.

FIG. 39 shows an autoclave unit 531 according to a third embodiment of the invention. In the autoclave unit 502 illustrated in FIG. 36, the autoclave unit 531 further has a bar code reader unit 532. The bar code reader unit 532 has a bar coder reader 533 reading out bar codes, and a bar coder reader I/F 534 serving as an interface outputting a signal read out by a bar code reader 533 to a CPU 508.

On the other hand, as an electronic scope 503 serving as an instrument processed in autoclave by the autoclave unit 531, a bar code section 535 on which a bar code representing kinds of an instrument that the instrument is an electronic scope 503 is provided on an operating section 522, for example. Thus, it is possible to read out bar codes by the bar code reader 533. When the bar code reader 533 reads out the bar code, a signal corresponding to the bar code is transmitted to a CPU 508 through the bar code reader I/F 534. The CPU 508 refers information corresponding to the signal to the stored contents of the ROM 515, and judges that the instrument is an electronic scope 3. The CPU 508 reads out autoclave processing conditions (temperature, humidity, pressure and time) registered beforehand with respect to the electronic scope 503 are read out from the ROM 515 and are displayed on the display panel 517.

In a case where confirmation is asked as to whether the autoclave processing may be done under the registered autoclave processing conditions, if a user selects "YES" the autoclave processing starts under the processing conditions (in this connection, the arrangement may be such that judgment asking the confirmation is omitted, the bar code reader is used to judge instruments processing in autoclave, and autoclave processing automatically starts under the corresponding autoclave processing conditions. Further, the default may be set in this manner).

Further, in a case where the autoclave processing conditions are changed, or in a case where instruments newly processed in autoclave are registered and the corresponding autoclave processing conditions are registered, data can be inputted by the data inputting means 514.

According to the autoclave unit 531, autoclave processing can be executed in accordance with autoclave processing conditions suitable for instrument processed in autoclave, without inputting operation of data specifying the instrument processed in autoclave. In this connection, the bar code section 535 may be provided on a connector 526, for example, or the like other than the operating section 522.

Figure 40:
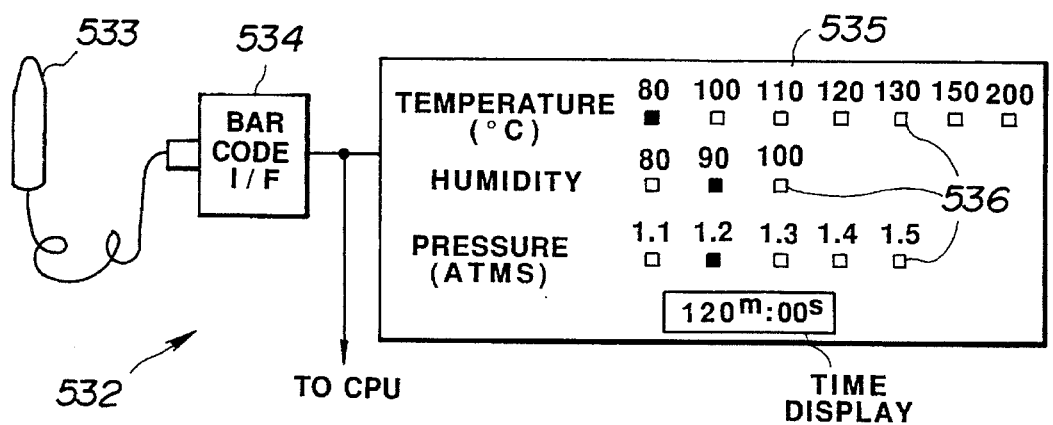
FIG. 40 is an arrangement view showing an arrangement of a bar code reader unit.

In connection with the above, as shown in FIG. 40, the arrangement may be such that the bar code reader unit 532 has a display portion 535, and LEDs 536 on a portion corresponding to various values of the contents read out by the bar code reader 533, that is, a temperature, a humidity and a pressure are turned on, and time are also displayed on the display section 535.

Further, the arrangement may also be such that color marks are provided on the instruments such as the electronic scope, the outside mounted camera and the like, in which the color marks are read out to automatically judge the object element, a temperature, time and the like are automatically set in accordance with the judgment results, and the operation of the autoclave processing starts.

Figure 41:
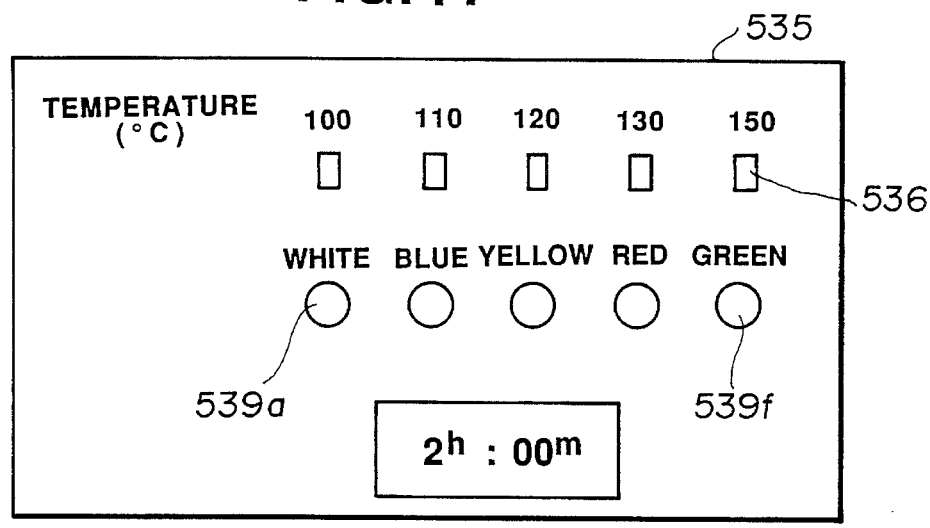
FIG. 41 is a view for explanation showing a display section of the bar code reader unit.

Furthermore, the arrangement is such that color marks are provided on the electronic scope, the outside mounted camera and the like, and a user manually selects switches 539a . . . , 539f (refer to FIG. 41) the same in color as the color marks, whereby time or the like is automatically displayed in accordance with the selected switch 539i (shown in FIG. 41 in a simplified form).

Figure 42:
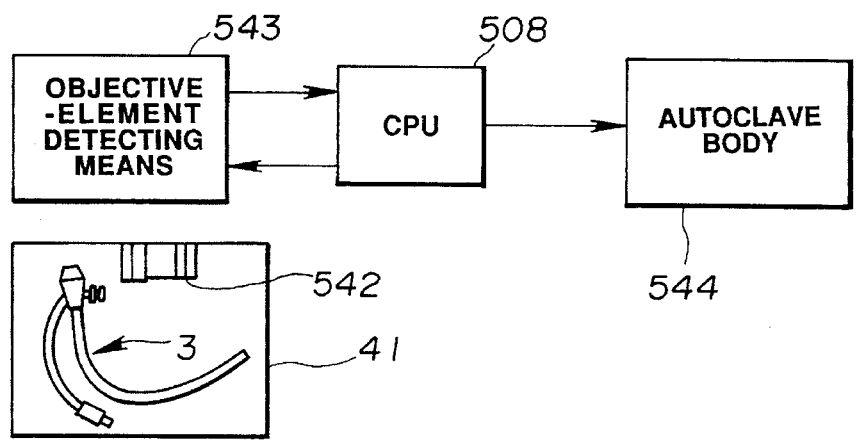
FIG. 42 is an arrangement view showing a modification of FIG. 39.

In connection with the above, as shown in FIG. 42, the arrangement may be such that exclusive trays 541 are provided respectively on instruments such as an electronic scope 503 and the like received in the autoclave unit, marks for identification such as bar codes, color marks 542 and the like are applied respectively to the exclusive trays 541, the marks are detected by an objective-element detecting unit 543 such as a bar code reader unit, a color mark reader unit or the like, an output from the objective-element detecting unit 543 is transmitted to the CPU 508, the CPU 508 judges an objective element, to display the setting contents on a display portion of an objective-element detecting unit 542, and a temperature or the like of a heater and cooler 511 or the like forming the autoclave unit body 544 is automatically set to automatically start the autoclave processing.

In connection with the above, the arrangement may be such that an objective element is judged by image processing, so that setting is made to an autoclave processing condition corresponding to the judgment, thereby automatically executing the autoclave processing.

Figure 43:
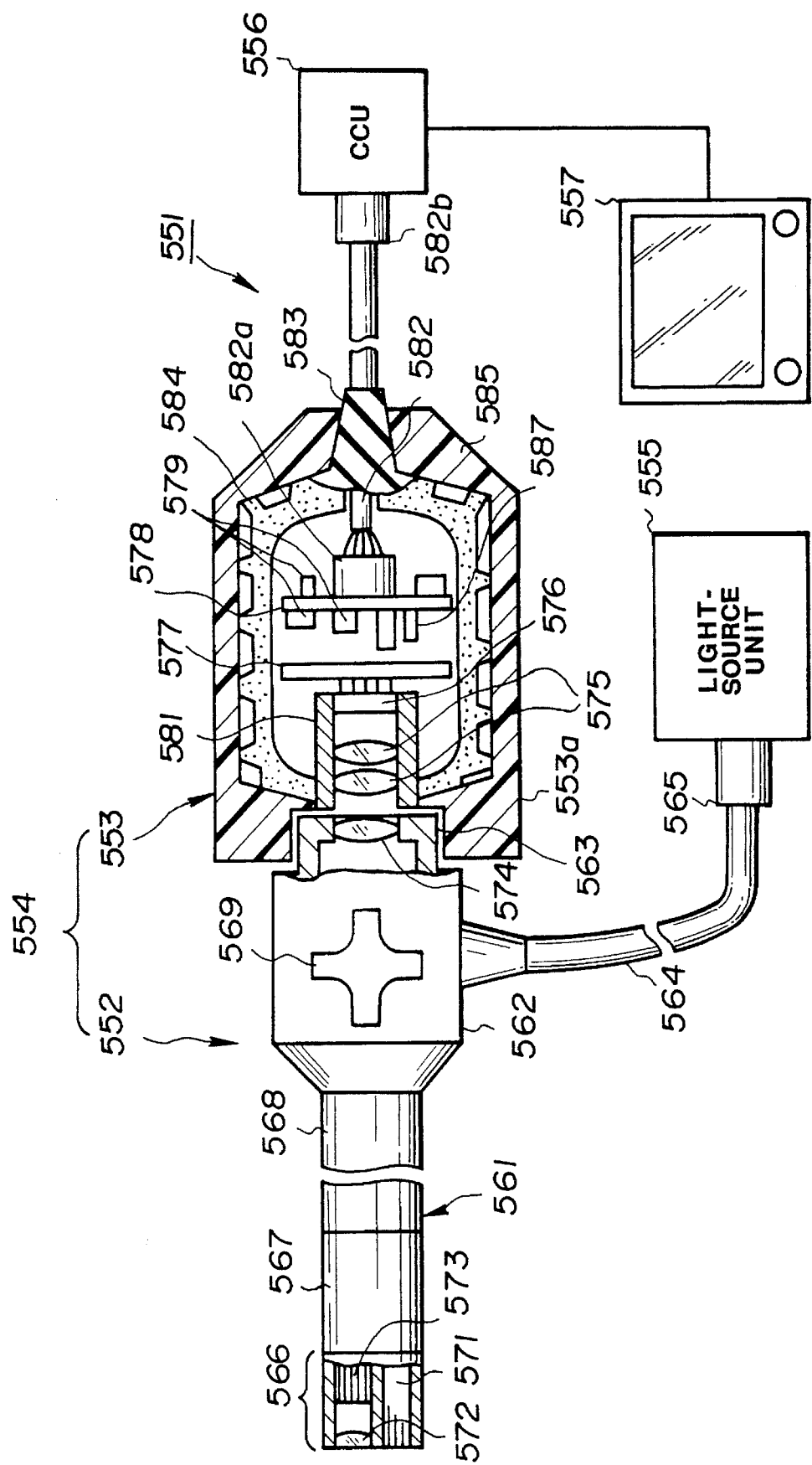
FIG. 43 is an arrangement view showing an endoscope system provided with means for prohibiting the use until a usable condition.

FIG. 43 shows an endoscope system provided with means for prohibiting the use until the medical instruments such as the endoscope and the like reaches a condition capable of being used after the autoclave processing.

The endoscope system 551 illustrated in FIG. 43 comprises a camera outside mounted endoscope 554 having a soft endoscope (referred also to as a "fiber scope") 552 and an outside mounted camera 553 mounted on the fiber scope 552, a light-source unit 555 for supplying an illuminating light to the fiber scope 552, a camera control unit (simply referred to as a "CCU") 556 for executing signal processing with respect to the outside mounted camera 553, and a monitor 557 for displaying an image signal outputted from the CCU 556.

The fiber scope 552 has an elongated inserting section 561 having elasticity, an operating section 562 large in diameter connected to a rearward end of the inserting section 561, an ocular section 563 formed at a rear end of the operating section 562, and a light cable 564 extending from the side of the operating section 562. A connector 565 provided at a proximal end of the light guide cable 564 can be detachably connected to the light-source unit 555.

The inserting section 561 has, from its forward end side, a hard forward end portion 566, a curved portion 567 capable of being curved, and a flexible tube portion 568 having elasticity. A curved knob 569 provided at the operating section 562 is operated whereby the curved portion 567 can be curved.

The connector 565 of the light guide cable 564 is connected to the light-source unit 555, whereby a white light due to a lamp (not shown) within the light-source unit 555 is irradiated upon an end surface of the light guide 571. The illuminating light transmitted by the light guide 571 is projected forwardly from an illuminating window whose end surface adjacent to the forward end portion 566 is mounted, to illuminate a subject (not shown).

By the projected illuminating light, the illuminated subject is arranged such that an optical image is imaged on a forward end surface of the image guide 573 fixedly mounted on a focus surface of the objective lens 572 provided at the forward end portion 566. The optical image is transmitted to the end surface adjacent to the ocular portion 563, and can be observed in magnification or enlargement through the objective lens 574 which is arranged in opposed relation to the end surface.

A camera head portion 553a of the outside mounted camera 553 can detachably be mounted on the ocular portion 563. The camera head portion 553a can be imaged onto a photoelectric transfer surface of the CCD 576 serving as an image pickup element, by an imaging lens system 575 which is opposed against the ocular lens 574. The CCD 576 is packaged or mounted on a printed circuit board 577. Electric parts 579 such as an IC, a capacitor, a resistor and the like for operating the CCD 576 are packaged on the printed circuit board 578 which is arranged in parallel relation to the printed circuit board 577 to form a peripheral circuit.

The imaging lens system 575 and the CCD 576 are fixedly mounted on the frame 581. The printed circuit boards 577 and 578 are also fixedly mounted on the frame 581 through a spacer (not shown). Further, a connector 582a of the signal cable 582 can be connected to the printed circuit board 578. The signal cable 582 passes through a rubber-like bushing 583, and is provided with a connector 582b capable of being connected to the CCU 556.

The printed circuit boards 577 and 578 on which the CCD 576 and the electronic parts 579 are packaged are received within the heat insulator 584 formed into a box-like configuration by polystyrene foam or the like. When the CCD 576 and the electronic parts 579 are thermally processed in sterilization, the printed circuit boards 577 and 578 and the electronic parts 579 are of a structure preventing conduction of heat into the heat insulator 584 from the outside by the heat insulator 584 as far as possible, that is, of an adiabatic structure, to prevent a temperature within the insulator 584 from rising. The circumference of the insulator 584 is covered with a mold element 585 formed into a box-like configuration by a plastic material or the like.

In the present embodiment, an irregular portion is formed on an outer surface of the insulator 584 to extremely reduce a contact area with a mold element 585 serving as an armored housing, thereby not to conduct the heat from the outside mold element 585 to the heat insulator 584 as far as possible.

The CCU 556 has means for generating a drive signal for adequately driving the CCD 576, and signal processing means for converting an electric signal outputted from the CCD 576 to a standard image signal (an NTSC image signal, for example) by application of the drive signal. The image output outputted from the CCU 556 is inputted into the monitor 557, and a subject image is displayed by the monitor 557.

Figure 44:
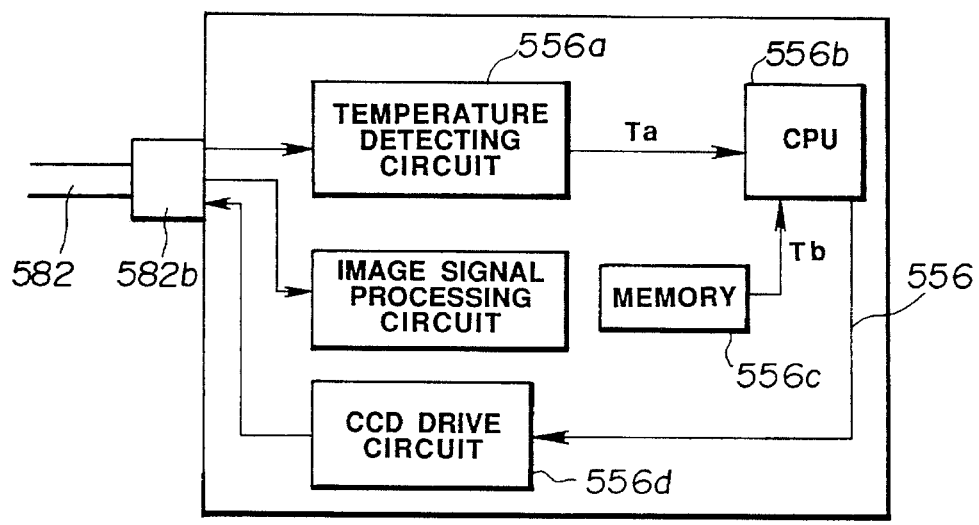
FIG. 44 is a block diagram showing an arrangement of a CCU.

A temperature sensor 587 is arranged between the printed circuit boards 577 and 578, for example, within the outside mounted camera 553. An output from the temperature sensor 587 is inputted into the temperature detecting circuit 556a within the CCU 556 as illustrated in FIG. 44. The output from the temperature sensor 587 is converted to temperature information Ta by the temperature detecting circuit 556a. The temperature information is transmitted to the CPU 556b at a constant interval of time, for example, and is compared with temperature information Tb read out from the memory 556c which stores therein temperature information Tb permitted in use. It is judged whether or not the detected temperature information Ta is a temperature equal to or less than the temperature information Tb. The CPU 556b prohibits operation of the CCD drive 556d until the temperature information Ta becomes a value equal to or less than the temperature information Tb.

When the detected temperature information Ta becomes a temperature equal to or less than the temperature information Tb, the CPU 556b releases prohibition of operation of the CCD drive circuit 556d so that the CCD drive signal is applied to the CCD 556 from the CCD drive circuit 556d. The CCD 576 inputs the photoelectrically transferred image signal to the image-signal processing circuit 556f within the CCU 556, by application of the CCD drive signal, so as to be transferred into a standard image signal, thereafter, the subject image is displayed on the monitor 557.

In the endoscope system 551, the insulator 584 is incorporated within the armored housing. By the insulator 584, the CCD 576 and the electronic parts 579 are adiabatically housed or received. Accordingly, in a case where the camera outside mounted endoscope 554 is received within the autoclave unit and is thermally processed in sterilization, the temperature rise of the inside CCD 576 and electronic parts 579 can be considerably restrained by the insulator 584 so that it is possible to restrain an inside temperature rise to the minimum. Thus, it is possible to prevent the inside CCD 576 and electronic parts 579 from being thermally destroyed and retrograded or degraded or the like.

For example, a typical example of a thermal sterilization process of the autoclave is to maintain 135° C. for five (5) minutes. It is known that almost all of bacteria are sterilized under this condition. Even if the thermal sterilization is executed under this condition, a temperature rise within the CCD 576 and electronic parts 579 can be kept to a minimum by the insulator 584.

Furthermore, in a case where, after the autoclave processing, the camera outside mounted endoscope 554 is connected to the CCU 556 as shown in FIG. 43 so that the electric power switch is turned ON, if the temperature Ta detected by the temperature sensor 587 is not lowered to a temperature equal to or less than the temperature information Tb permitted in use, the CCD drive circuit 556d is maintained under a condition that its operation is prohibited. Accordingly, it is possible to effectively prevent that a characteristic of the CCD 576 or the like is deteriorated to cause a malfunction.

Figure 45:
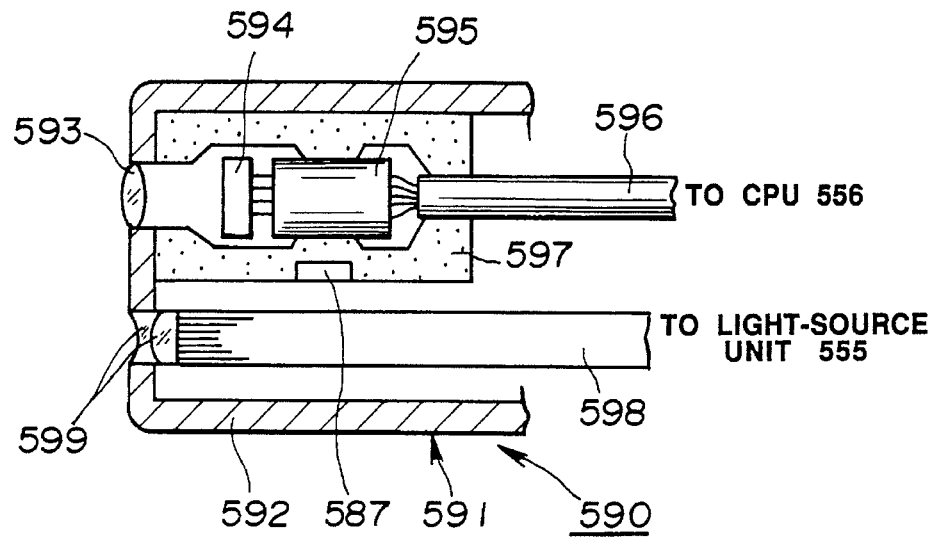
FIG. 45 is a cross-sectional view showing a location adjacent to a forward end of an electronic scope provided with a temperature sensor.

FIG. 45 shows that a temperature sensor 587 is provided on the electronic scope 591 in place of the camera outside mounted endoscope 554 illustrated in FIG. 43.

An objective lens 593 is mounted on an observation window in the forward end surface of the armored frame 592 which forms the inserting section 591 of the electronic scope 590. The CCD 594 has a photoelectric transfer surface which is arranged on the focus surface of the objective lens 593. The CCD 594 is of a structure integrated with the hybrid substrate 595. A signal photoelectrically transferred by the CCD 594 passes through the hybrid substrate 595, passes through a transmitting cable 596 connected to the hybrid substrate 595 and is inputted to the CPU 556 illustrated in FIG. 44.

A heat insulating element 597 is received in the armored frame 592. By the heat insulating element 597, the CCD 597 and the hybrid substrate 595 are covered. The heat insulating element 597 is formed by polystyrene foam, for example. The polystyrene foam has a thermal conductive thereof which is equal to or less than $1/10$ as compared with the armored frame 592. A material low in thermal conductivity may be used in place of the polystyrene foam.

A light guide 598 for transmitting an illuminating light is inserted in the armored frame 592. An end of the light guide 598 at a hand is connected to a light-source unit 555 illustrated in FIG. 43. The illuminating light from the light-source unit 555 is transmitted and is outgone toward the forward subject through the illuminating lens 599 further from the forward end surface. A temperature sensor 587 is further arranged adjacent to the hybrid substrate 595. An output from the temperature sensor 587 is inputted to the temperature detecting circuit 556a through the transmitting cable 596.

Also with the electronic endoscope 590, the CCD 597 and the hybrid substrate 595 are covered by the heat or thermal insulator 597. Accordingly, advantages similar to those of the camera outside mounted endoscope 554 illustrated in FIG. 43 are produced.

Figure 46:
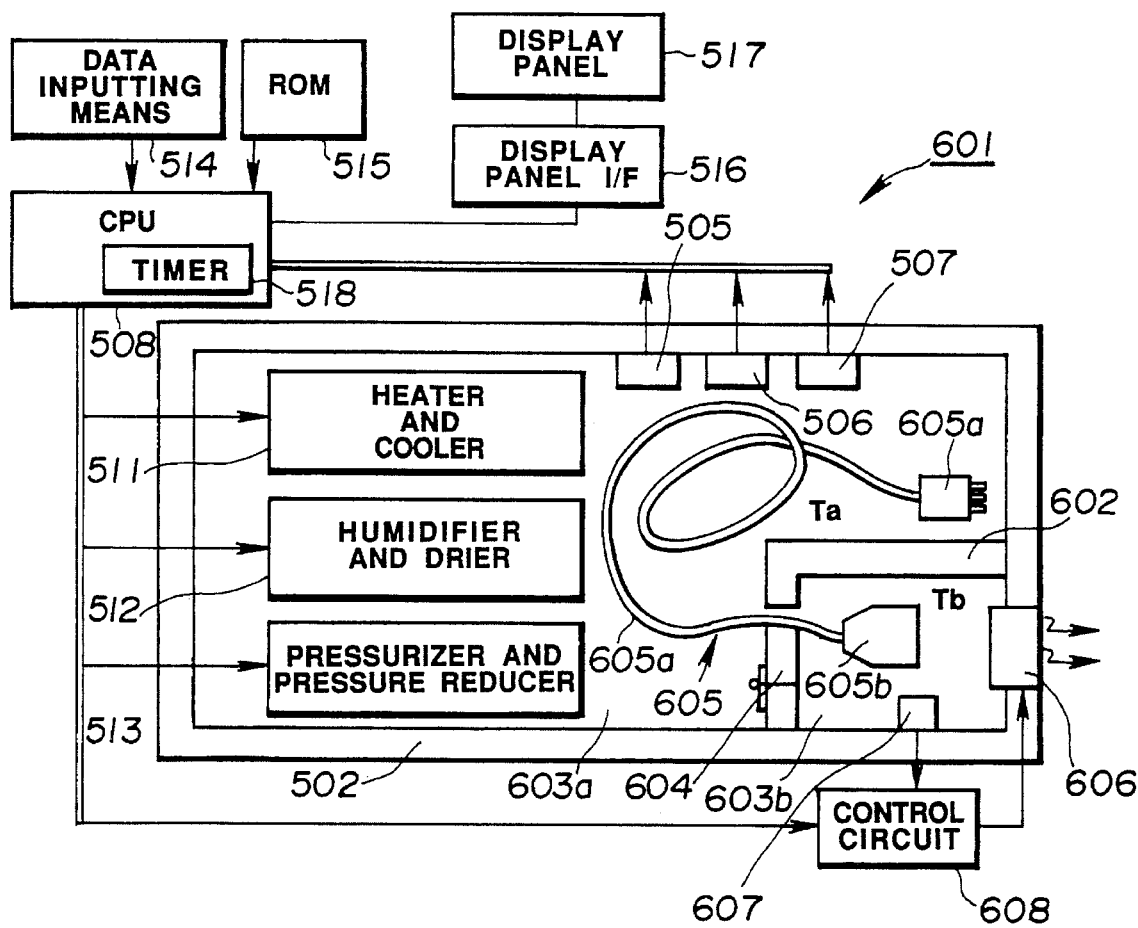
FIG. 46 is an arrangement view showing an autoclave unit in accordance with a fourth embodiment of the invention, which is capable of being set in a plurality of temperature areas.

FIG. 46 shows an autoclave unit 601 so arranged as to be capable of setting the temperature within the autoclave unit to a plurality of temperature ranges. For example, in the autoclave unit 501 illustrated in FIG. 36, the autoclave unit 502 is partitioned by a division or partition wall 602 formed by an insulating material, to form two receiving spaces 603a and 603b. Further, a door 604 is provided on a part of the partition wall 602, so that a part of the instruments processed in autoclave can be received and taken out from one of the receiving spaces 603a to other receiving space 603b. Furthermore, in a case where the door 604 is closed, the receiving space 603a is maintained to a condition communicating with the receiving space 603b through a minute or small communicating portion.

The inside of one receiving space 603a is controlled similarly to FIG. 36, so as to be maintained to the temperature Ta or the like of the condition selectively set by the data inputting means 514 in accordance with the instrument (the outside mounted camera 605, for example, in a case of FIG. 46) received at processing in autoclave. The other receiving space 603b is provided with a fan 606 forming cooling means, within an outer wall of the receiving space 603b, for example. The fan 606 is operated by an output from the temperature sensor 607 through a control unit 608.

The control circuit 608 is connected to an output port of the CPU 508, and can set a temperature of the receiving space 603b at autoclave processing, by the data inputting means 514. That is, when data inputting of a temperature (a value thereof) Tb desired to be set is executed, the CPU 508 sets a temperature to be held in the control circuit 608 to the value Tb, and controls a rotational speed of the fan 606 such that the output from the temperature sensor 607 is brought to this value Tb.

The temperature Ta in the one receiving space 603a is set higher than the temperature Tb within the other receiving space 603b. Accordingly, the temperature Tb within the other receiving space 603b can be retained to the temperature Tb by control of an amount of heat radiated by the fan 606.

A head portion 605b of the outside mounted camera 605 low in heat resistance is received within the receiving space 603b. The greater part of the cable 605a and a connector 605c provided at a forward end of the cable 605a are higher in heat resistance than the head portion 605b, so that the cable 605a and the connector 605c are received within the receiving space 603a. Thus, the cable 605a and the connector 605c can be processed in autoclave.

According to the unit 601, in a case where an instrument to be processed in autoclave is formed by a portion lower in heat resistance and a portion higher in heat resistance, the portions are received respectively in receiving spaces held or retained to temperatures suitable respectively for the heat resistances, and the portions can be processed in autoclave at temperatures different from each other. Accordingly, the autoclave processing can be executed more efficiently than the unit 501 illustrated in FIG. 36.

Figure 47:
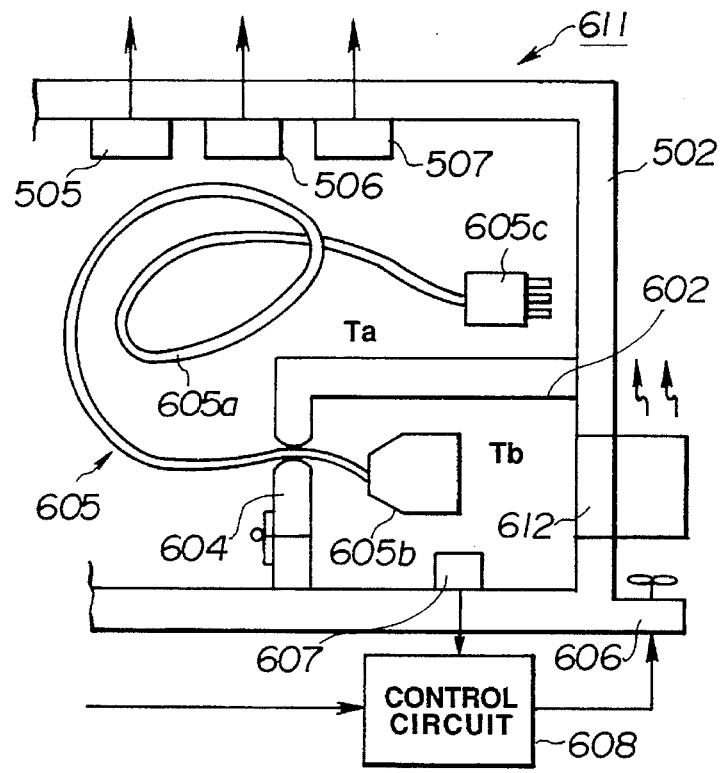
FIG. 47 is an arrangement view showing a portion of an autoclave unit in accordance with a modification of FIG. 46.

Other functions and advantages are similar to those of the unit 501 illustrated in FIG. 36. FIG. 47 shows a portion of the autoclave unit 611 in accordance with a modification of FIG. 46. In the autoclave unit 611, in FIG. 46, when the door 604 is closed, the cable 605a of the outside mounted camera 605 can pass under an urging or pressing condition, and a condition is brought to a condition under which the receiving space 603a is substantially isolated from the receiving space 603b. Further, a radiating fin 612 is provided on the outer wall surface in place of the fan 606, and a fan 606 is provided adjacent to the outer wall surface. The fan 606 is controlled in operation of rotation and stop of rotation by a control unit 608, to control an amount of radiation of the radiating fin 612, thereby holding or retaining the temperature of the receiving space 603b to Tb.

In this unit 611, since the receiving space 603a and the receiving space 603b are substantially isolated from each other, it is possible that, for example, instrument parts received within the receiving space 603a are executed in autoclave processing only for a short period of time ta at a higher temperature Ta, while instrument parts received within the other receiving space 603b are processed in autoclave for a longer period of time tb at a lower temperature Tb.

This unit 611 can be set to a condition different from the outside more than the case of the unit 601 illustrated in FIG. 46 so as to execute autoclave processing (in the unit 601 illustrated in FIG. 46, since a portion including the fan 606 communicates with the outside, there is a possibility that it is difficult to set and maintain a condition to a condition largely different from the outside).

In connection with the above, it is possible that the humidity sensor and the pressure sensor are further received within the receiving space 603b, the inside of the receiving space 603b are maintained to desired temperature, humidity and pressure conditions by outputs from the sensors.

Figure 48:
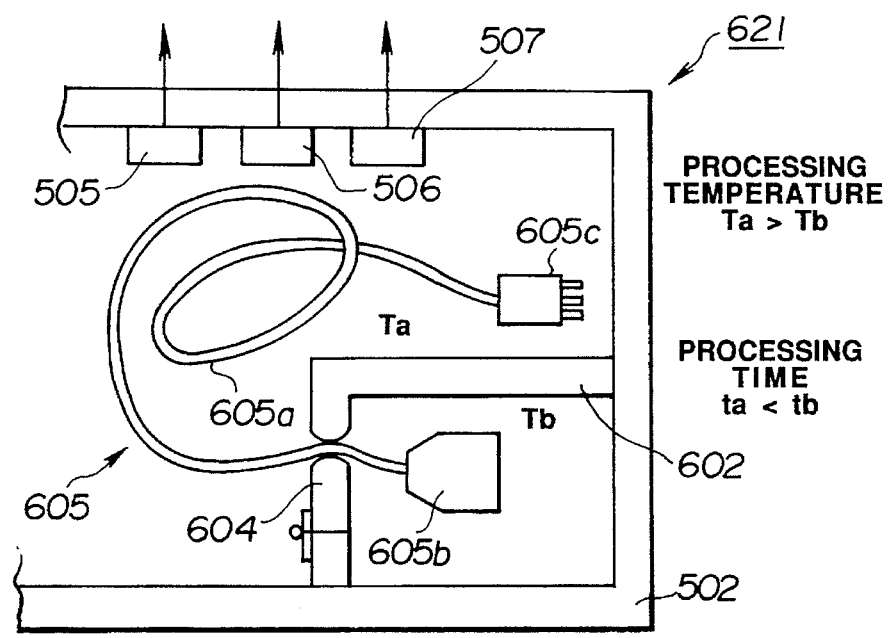
FIG. 48 is an arrangement view showing a portion of an autoclave unit in accordance with another modification of FIG. 46.

In connection with the above, the autoclave unit 621 illustrated in FIG. 48 adopts an arrangement having the fan 606 and the like. That is, two receiving spaces 603a and 603b are formed within the autoclave unit 502 by a partition wall 602 formed by a heat insulating material. A door 604 is provided on a part of the partition wall 602. One receiving space 603a and the other receiving space 603b can be set to a condition where one receiving space 603a and the other receiving space 603b communicate with each other.

In a case where the door 604 is closed, the cable 605a of the outside mounted camera 605 can pass under a biased condition, for example. When, for example, the autoclave processing starts, the temperature within the receiving space 603a rises and the temperature thereof rises to Tb, the door 604 is closed by a drive mechanism (not shown), whereby it is possible to set the temperature within the receiving space 603b to Tb. On the other hand, the temperature within the receiving space 603b is set to Ta.

Since, also for the unit 621, the receiving space 603a and the receiving space 603b are substantially isolated from each other, it is possible that the instrument part received within the receiving space 603a, for example, is processing in autoclave only for a short period of time ta at higher temperature Ta, and the instrument part received within the other receiving space 603b is processed in autoclave for a longer period of time tb at a lower temperature Tb.

Figure 49:
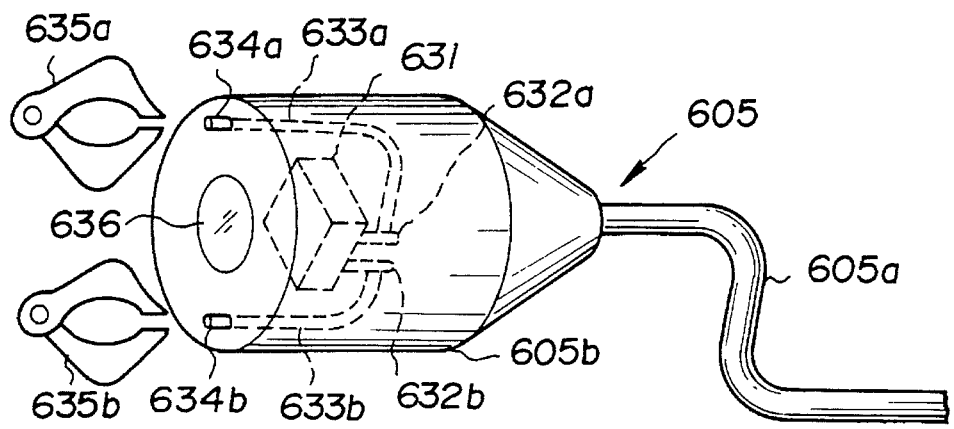
FIG. 49 is a perspective view showing an outside mounted camera provided with means for protecting a portion lower in heat resistance.

FIG. 49 shows an outside mounted camera 605 provided with means for locally protecting a portion low in heat resistance. As shown in FIG. 49, a pair of radiating pins 634a and 634b are so provided as to project to a forward end surface, for example, through a pair of conductors 633a and 633b superior in heat from the signal pins 632a and 632b of the CCD 631 in the camera head 605b. A pair of heat radiation clamp elements 635a and 635b are mounted on the heat radiating pins 634a and 634b, thereby preventing heat from being transmitted to the CCD 631 in a case of the autoclave processing.

In a case where the camera head 605b is received within the receiving space 603b illustrated in FIG. 46, for example, if the minimum temperature required for the autoclave processing is Tb and the CCD 631 has no heat resistance with respect to the temperature Tb, the clamp elements 635a and 635b are mounted and are arranged adjacent to the fan 606 so that the clamp elements 635a and 635b can be brought to a temperature equal to or less than the temperature Tb.

In this case, almost all of the interior of the receiving space 603b is retained to the temperature Tb, a part is locally retained to a temperature equal to or less than the temperature Tb. In this case, the CCD 631 is arranged inside. In a case where the CCD 631 is used in insertion into an organism, a portion of the CCD 631 does not become dirty.

Accordingly, the temperature may be a temperature equal to or less than the minimum temperature Tb required for autoclave processing.

In connection with the above, the imaging lens 636 is arranged in front of the CCD 131, to focus an optical image onto the CCD 631.

Figure 50:
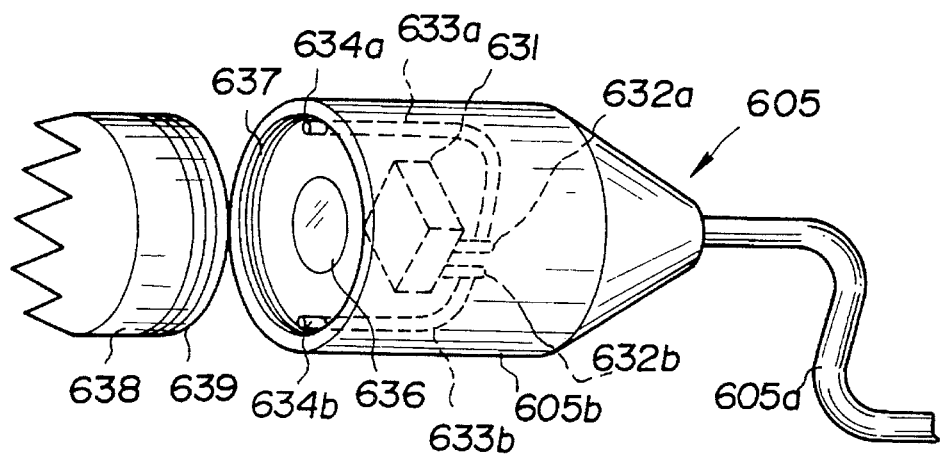
FIG. 50 is a perspective view showing a modification of FIG. 49.

FIG. 50 shows an arrangement in which a female threaded portion 637 is provided on the forward end surface of a camera head 605b, and a male thread 639 of a heat sink 638 is threadedly engaged with the female threaded portion 637 so that the heat sink 638 is mounted. By this mounting, a pair of heat radiating pins 634a and 634b are abutted against the heat sink 638 so that heat can be radiated.

In connection with the above, in FIGS. 49 and 50, the signal pins 632a and 632b are connected to the heat radiating pins 634a and 634b. However, the arrangement may be such that a pin is provided exclusively for heat radiation, which is in thermally constant with the CCD 631, heat radiation is executed by the pin, and the pin is connected to the heat radiation pins 634a and 634b to execute heat radiation.

Further, although it is shown that heat radiation is executed with respect to the CCD 631, the arrangement may be such that semiconductor parts such as an amplifier for amplifying output signals from IC, CCD forming a drive circuit for the CCD, for example, and an electronic part such as a capacitor and the like are similarly heat-radiated.

Figure 51:
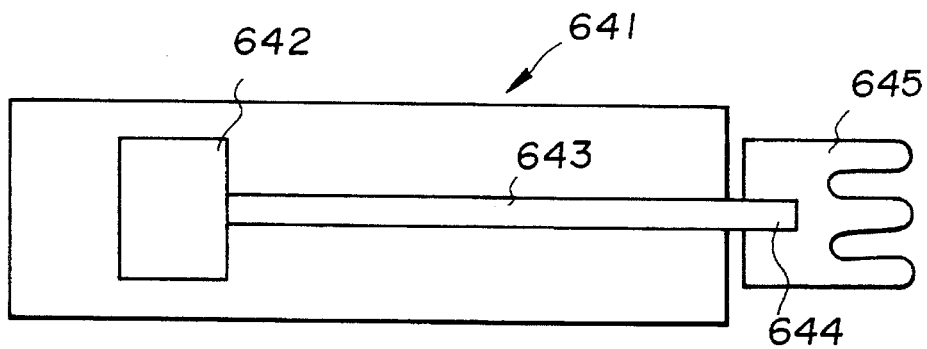
FIG. 51 is a view showing a conceptional arrangement of means for protecting a portion lower in heat resistance.

Means for heat-radiation or cooling provided in FIG. 49 and the like becomes a concept view illustrated in FIG. 51. A portion 642 weak in heat exists in the medical instrument 641. The portion 642 is connected to a conductor 643 superior in heat. There is a pin 644 exposed to the outside which exists in the conductor 643. A heat radiating element 645 is connected to the pin 644 to execute heat radiation, thereby protecting thermally the portion 642 weak in heat.

An autoclave unit provided with a function of prohibiting the use until the temperature of the endoscope or the like processed in autoclave by the autoclave unit is lowered to a temperature capable of being used will next be described.

Figure 52:
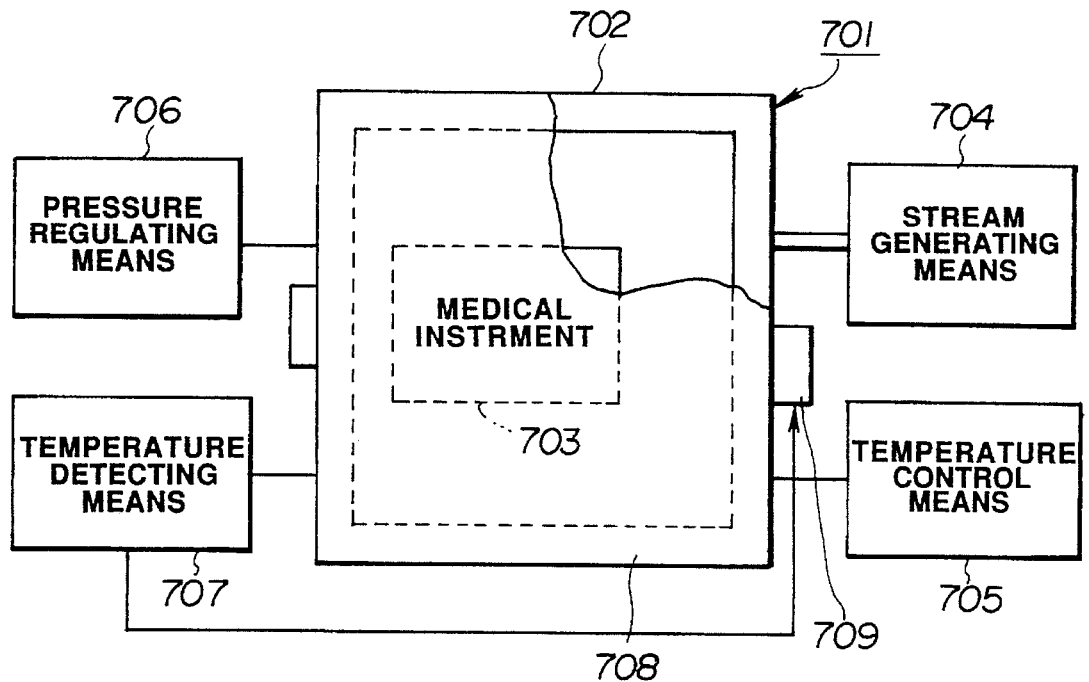
FIG. 52 is a schematic arrangement view showing an autoclave unit in accordance with a fifth embodiment of the invention.

First, outline will be described with reference to FIG. 52. As shown in FIG. 52, an autoclave unit 701 has an autoclave unit body 702 formed by a pressure-proof container capable of withstanding a high pressure. Electrical medical instruments 703 such as an endoscope and the like are received within the autoclave unit body 702. Steam having a high temperature and a high pressure generated by steam generating means 704 is injected into the autoclave unit 702.

The injected steam is maintained to a predetermined temperature by temperature control means 705 connected to the autoclave unit body 702. Further, a pressure within the autoclave unit body 702 is controlled to a predetermined or constant pressure by pressure regulating means 706 connected to the autoclave unit body 702.

Furthermore, a temperature within the autoclave unit body 702 and a temperature of the medical instrument 703 after the autoclave processing are detected by the temperature detecting means 707 connected to the autoclave unit body 702. A door lock/unlock mechanism 709 for opening and closing the door 708 of the autoclave unit body 702 is locked to a closed condition and is prohibited in opening until the temperature is lowered to a temperature equal to or less than the temperature at which the medical instrument 703 can be used. In a case where the temperature is lowered to a temperature equal to or less than a usable temperature, the lock is released.

Figure 53:
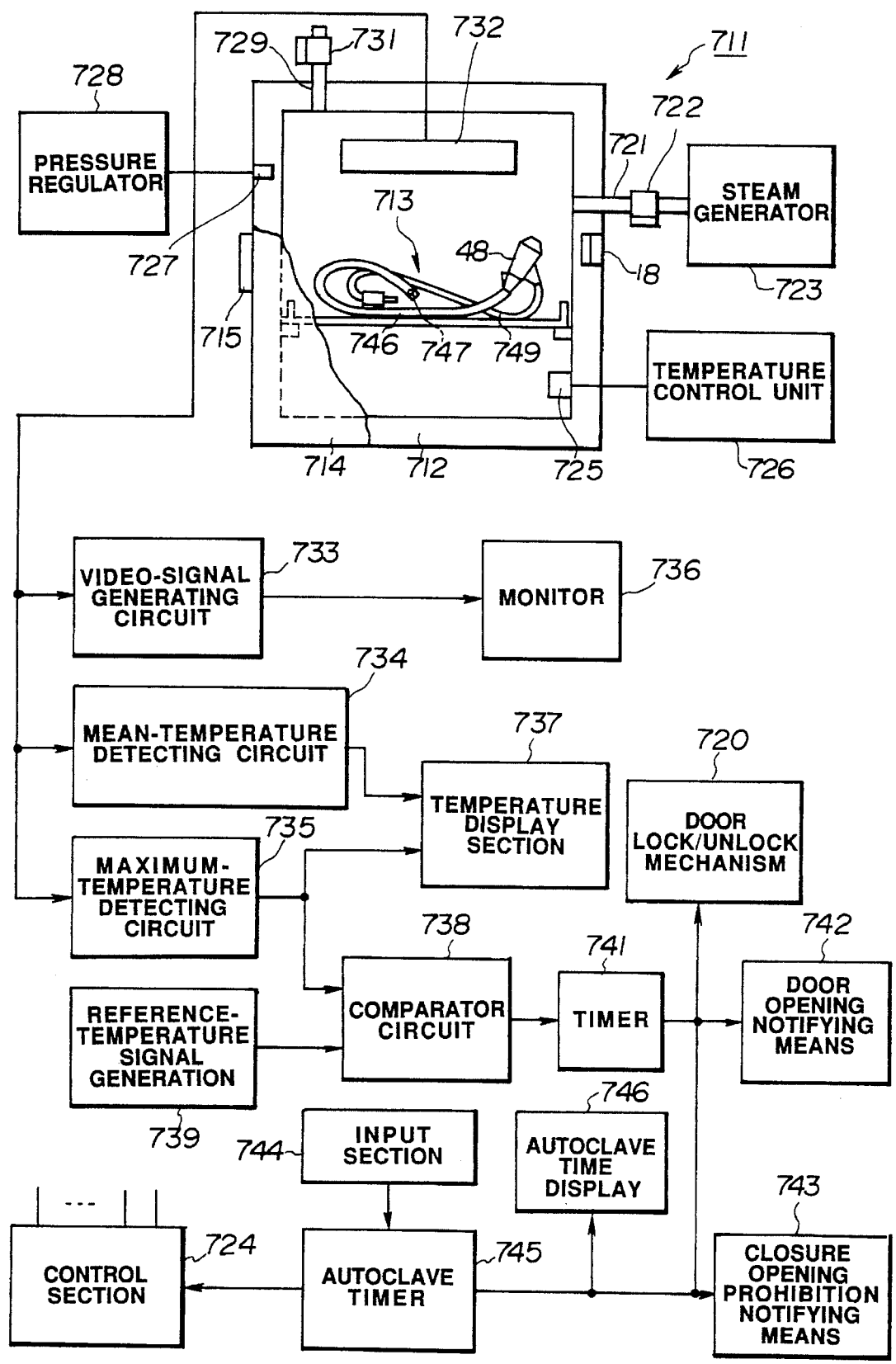
FIG. 53 is a specific arrangement view showing the fifth embodiment of the invention.

Description will next be made with reference to FIG. 53. As shown in FIG. 53, in the autoclave unit 711 in accordance with the fifth embodiment, an autoclave unit body (or an autoclave tank) 712 is formed by a receiving container capable of withstanding a high pressure and a high temperature. A door 714 provided for angular movement in a front surface of the autoclave unit body 712 is opened so that electrical medical instrument such as an endoscope 713 or the like can be received.

Figure 54A:
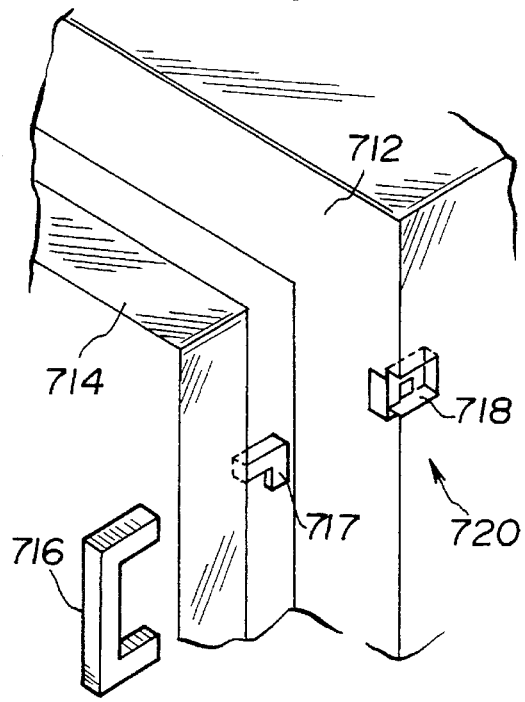
FIGS. 54a and 54b are perspective views showing a mechanism for opening and closing a door, in the fifth embodiment of the invention.

One of opposite ends of the door 714 is mounted for angular movement on the autoclave unit body 712 by a hinge 715. As shown in FIG. 54a, a knob 716 for executing opening and closing operation is mounted on a front surface of the other end. A hook 717 in the form of a letter L, for example, is provided in projection on the rear surface. The hook 717 can be received in a groove 718 which is provided on a corresponding location in the autoclave unit body 712.

Figure 54B:
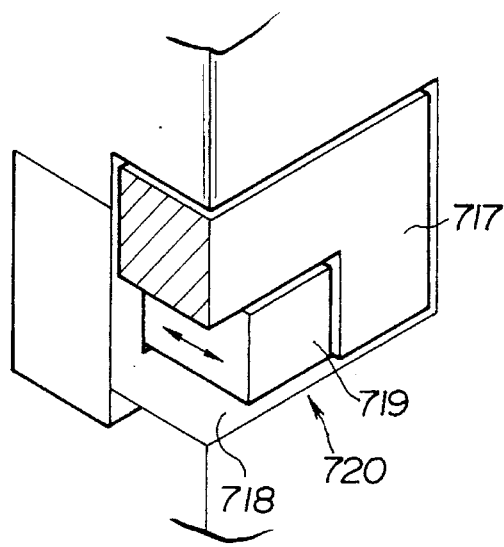

As shown in FIG. 54b, an electromagnetic plunger 719 projecting into the groove 718 and retracting from the groove 718 by current flowing through the electromagnetic coil, for example, is provided on a side surface of the groove 718. Moreover, a door lock/unlock mechanism 720 capable of locking the door 714 to a closed condition and releasing (unlock) the locking to open the door 714 is formed. For example, when the door 714 is brought to the lock condition, the electromagnetic plunger 719 projects into the groove 718, as illustrated in FIG. 54b, so that the hook 717 cannot be withdrawn from the groove 718.

As shown in FIG. 53, a bore is provided in a wall surface of the autoclave unit body 712. One opening end of the pipe 721 is fixed. The other end of the pipe 721 is connected to a steam generator 723 such as a boiler or the like for generating steam of a high temperature and a high pressure through a first electromagnetic valve 722. The first electromagnetic valve 722 is controlled in opening and closing by a control portion 724. When sterilization using steam of a high temperature and a high pressure, that is, autoclave processing is executed, the first electromagnetic valve 722 is opened so that steam is injected. Further, the steam generator 723 has a temperature control portion (not shown) for controlling a temperature of the steam generated to a constant temperature to maintain or retain the temperature to a temperature in accordance with a temperature command signal on the basis of a signal from the control portion 724.

A temperature sensor 725 is arranged within the autoclave unit body 712, and detects an internal temperature to output the detected temperature to an outside temperature control unit 726. The temperature control unit 726 controls the temperature within the autoclave unit 712 so as to be maintained to a constant temperature, for example, 135° C. in a case where the autoclave processing is executed. The temperature control unit 726 is connected to a control portion 724. When a user sets a temperature to be maintained, a temperature signal representing the former temperature is transmitted to the steam generator 723 through the control portion 724, for example, to control the temperature of the generated steam to become this temperature.

Further, a pressure sensor 727 is arranged within the autoclave unit body 712, to detect an inside pressure to output the inside pressure to the outside pressure regulator 728. In a case where the pressure regulator 728 executes autoclave processing, the pressure regulator 728 controls the pressure within the autoclave unit body 712 to a constant pressure, for example, to approximately 2 atms, suitable for autoclave processing.

In a case where the pressure regulator 728 regulates a pressure, the pressure regulator 728 executes regulation by control of opening and closing of the second electromagnetic valve 731 mounted on a pipe 729 provided so as to extend through a wall surface of the autoclave unit body 712, through a control portion 724, and controls opening and closing of the first electromagnetic valve 722 through a control section 724. For example, in a case where the internal pressure is reduced, the second electromagnetic valve 731 is closed, and the first electromagnetic valve 722 is opened to inject steam, thereby controlling opening and closing so that the inside pressure reaches a pressure to be held or retained.

Furthermore, an infrared camera 732 for detecting the whole temperature within the autoclave unit body 712 after the autoclave processing, that is, a temperature of a wall surface within the autoclave unit body 712 and a temperature of an endoscope 713, for example, serving as a medical instrument received within the autoclave unit 713 is received and arranged within the autoclave unit body 712. An output signal from the infrared camera 732 is inputted to the video signal generating circuit 733, a mean-temperature detecting circuit 734, and a maximum-temperature detecting circuit 735. The video-signal generating circuit 33 executes signal processing with respect to the output signal from the infrared camera 732, to display a temperature image on a monitor 736.

Furthermore, the mean-temperature detecting circuit 734 detects a mean temperature from the output signal from the infrared camera 732, and displays the mean temperature on the temperature display portion 737. Moreover, the maximum-temperature detecting circuit 735 detects a maximum temperature from the output signal of the infrared camera 732. The maximum temperature is displayed on the temperature display portion 737, and is outputted to the comparator circuit 738. A reference temperature signal corresponding to a set reference temperature from the reference-temperature signal generating circuit 739 capable of variably setting a reference temperature capable of opening a door 714 is also inputted to the comparator circuit 738. The comparator circuit 738 compares two input signals with each other.

The comparator circuit 738 outputs a signal starting a timer 741 when a detected maximum temperature is lowered than the reference temperature. If it is judged by the comparator circuit 738 that the detected maximum temperature is lowered less than the reference temperature, it can be deemed that the temperature is lowered to a temperature so that there has no objection so that the door 714 is open, and the internal or inside endoscope 723 is taken out and is used. In order to further secure the safety, however, in the present embodiment, the arrangement may be such that, when the above judgment is executed, the timer 741 starts, and the door 714 is open after a predetermined period of time elapses so that the temperature is further lowered.

Specifically, when preset time and several minutes, for example, elapses from time that the timer 741 starts, the timer 741 output an elapse signal of "L" for example By this elapse signal, the door lock/unlock mechanism 720 is brought to an unlock condition, and door-open notifying means 742 formed by a buzzer or the like is operated, to notify the user that the door 714 may be opened.

When the above elapse signal is not outputted, the door lock/unlock mechanism 720 retains the lock condition. Further, the door lock/unlock mechanism 720 notifies the user by the fact that it is indicated that it is prohibited that the door 714 is opened, as "during prohibition of door opening" or the like by door-open prohibition notifying means 743 which is formed by an LCD or LED display portion, for example.

Furthermore, a user can input how time the autoclave processing is executed, from the input portion 744. When the inputting of the time is executed, the autoclave timer 745 is set. Its time is displayed by the autoclave time display portion 746. Its time is transmitted to the control portion 724. When the autoclave processing starts, the autoclave timer 745 brings the door lock/unlock mechanism 720 to a lock condition. It is notified that the door-open prohibition notifying means 743 is under an operative condition, that is, opening of the door 714 is prohibited.

In connection with the above, the endoscope 713 housed within the autoclave unit body 712 and executed in autoclave processing is an electronic scope in which a CCD 747 is built which forms image pickup means at a forward end portion of the elongated inserting section 746. The inserting section 746 has a proximal end thereof at which an operating section 748 wide in width is formed. A universal cable 749 extends from the operating section 748. A connector mounted on a forward end of the universal cable 749 can be connected to a video processor (not shown). By the fact that the connector is connected to the video processor, an illuminating light is supplied to the light guide from the light-source unit within the video processor. Furthermore, an output signal from the CCD 747 is processed in signal so that an image signal capable of executing display on a monitor is generated.

According to the autoclave unit 711 according to the fifth embodiment, the interior of the autoclave unit body 712 is monitored as a whole by the infrared camera 732. If there are locally portions high in temperature, the temperature is detected by the maximum temperature detecting circuit 735. After the maximum temperature reaches a temperature equal to or less than a temperature at which it is judged that the door 714 should be open, the door 714 is open after several minutes further in anticipation of safety. It is not prohibited that the door 714 is open until now. Accordingly, the medical instruments built therein electronic components or parts such as the endoscope 713 and the like after having been taken out is lowered in temperature to a temperature at which there is no problem in using the medical instruments. For this reason, in a case where the medical instruments are used after having been taken out of the unit 711, it is possible that a characteristic is deteriorated due to the use, and a malfunction may occur.

Figure 55:
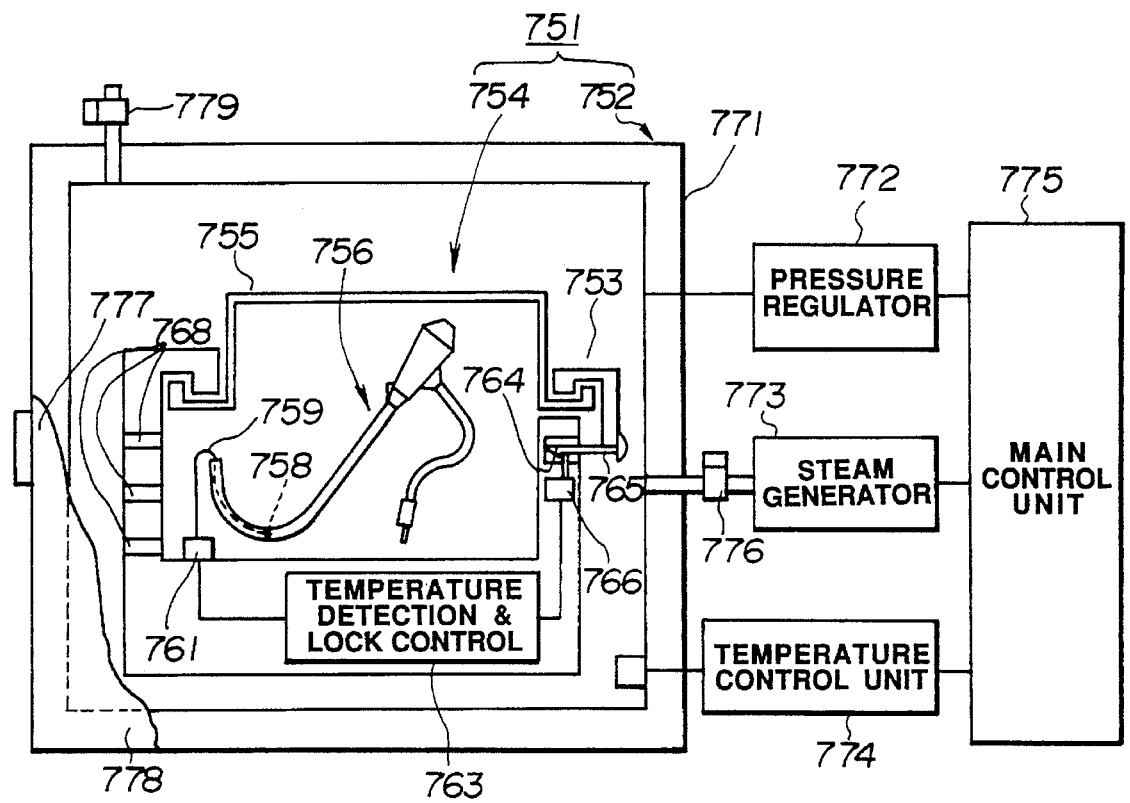
FIG. 55 is an arrangement view showing a sixth embodiment of the invention.
Figure 56:
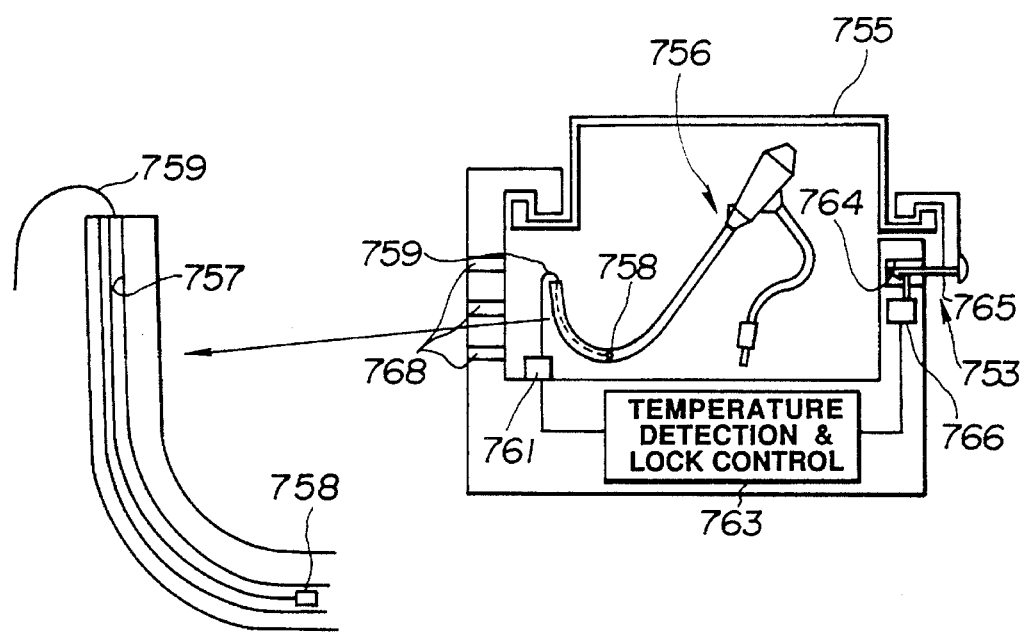
FIG. 56 is an arrangement view showing a structure of an endoscope autoclave tray in the sixth embodiment of the invention.

FIG. 55 shows an autoclave unit 751 according to a sixth embodiment of the invention. The embodiment comprises an ordinary or normal autoclave unit 752 (a unit from which a portion of the endoscope autoclave tray 754 illustrated in FIG. 56 has been removed from FIG. 55), and an endoscope autoclave tray 754 received in the autoclave unit 752 and provided with a lock/unlock mechanism 753. The lid 755 is open whereby, as shown also in FIG. 56, it is possible for the endoscope autoclave tray 754 to accommodate the endoscope 756 within the endoscope autoclave 754.

Further, a temperature sensor 759 capable of being accommodated within the channel 757 of the endoscope 756 is mounted to a forward end of a lead wire 759, at a location within the endoscope autoclave tray 754. A connector 761 provided at a proximal end of the lead wire 759 is connected to a connector receptor provided on a wall surface of a bottom of the endoscope autoclave tray 754, whereby the temperature sensor 758 is electrically connected to a temperature detection and lock control circuit 763 which is embedded within the wall surface.

The temperature detection and lock control circuit 763, for example, compares and judges as to whether a temperature detected on the basis of the output from the temperature sensor 758 is lowered equal to or less than a reference temperature. In a case where the temperature is not lowered to a temperature equal to or less than the reference temperature, a signal that the lock/unlock mechanism 753 is retained under a lock condition is outputted. The lock/unlock mechanism 753 is retained under a lock condition that the lid 755 is closed.

The lock/unlock mechanism 753 comprises a pin 765 inserted into, for example, a groove 764 in the endoscope autoclave tray 754, and an electromagnetic plunger 766 engaged with the hook provided at the forward end of the pin 765 to restrict that the pin 765 slips out from the groove 764. The electromagnetic plunger 766 is engaged with the hook by a lock signal. The electromagnetic plunger 766 is released from the engagement when the lock signal is not outputted. Thus, it is possible to draw the pin 765 out of the groove 764. When a condition is brought to a condition that the pin 765 is released from the groove 764, it is possible to open the lid 755.

In connection with the above, the endoscope autoclave tray 754 is provided with ventilation bores 768, 768, . . . Steam enters into the endoscope autoclave tray 754 to enable sterilization to be executed. In a case where the endoscope autoclave tray 754 is taken out to the outside after the autoclave processing, the endoscope autoclave tray 754 can quickly be cooled (cooled by air).

A pressure regulator 772 for regulating a pressure with respect to the autoclave tank 771, a steam generator 773 for generating steam, and a temperature control unit 774 for controlling a temperature are connected to the autoclave unit 752 in which the endoscope autoclave tray 754 is received, and are controlled by a main control unit 775. Furthermore, a pipe provided with an electromagnetic valve 776 is mounted on the autoclave tank 771.

The autoclave unit 752 is capable of being open and closed by a door 778 which is movable angularly by a hinge 777. Moreover, a discharge pipe provided with an electromagnetic valve 779 is mounted on the autoclave tank 771, and is open at the outside.

The embodiment is advantageous in that the ordinary or normal autoclave unit 752 can be utilized, and has functional advantages similar to those of the fifth embodiment in other aspects.

Figure 57:
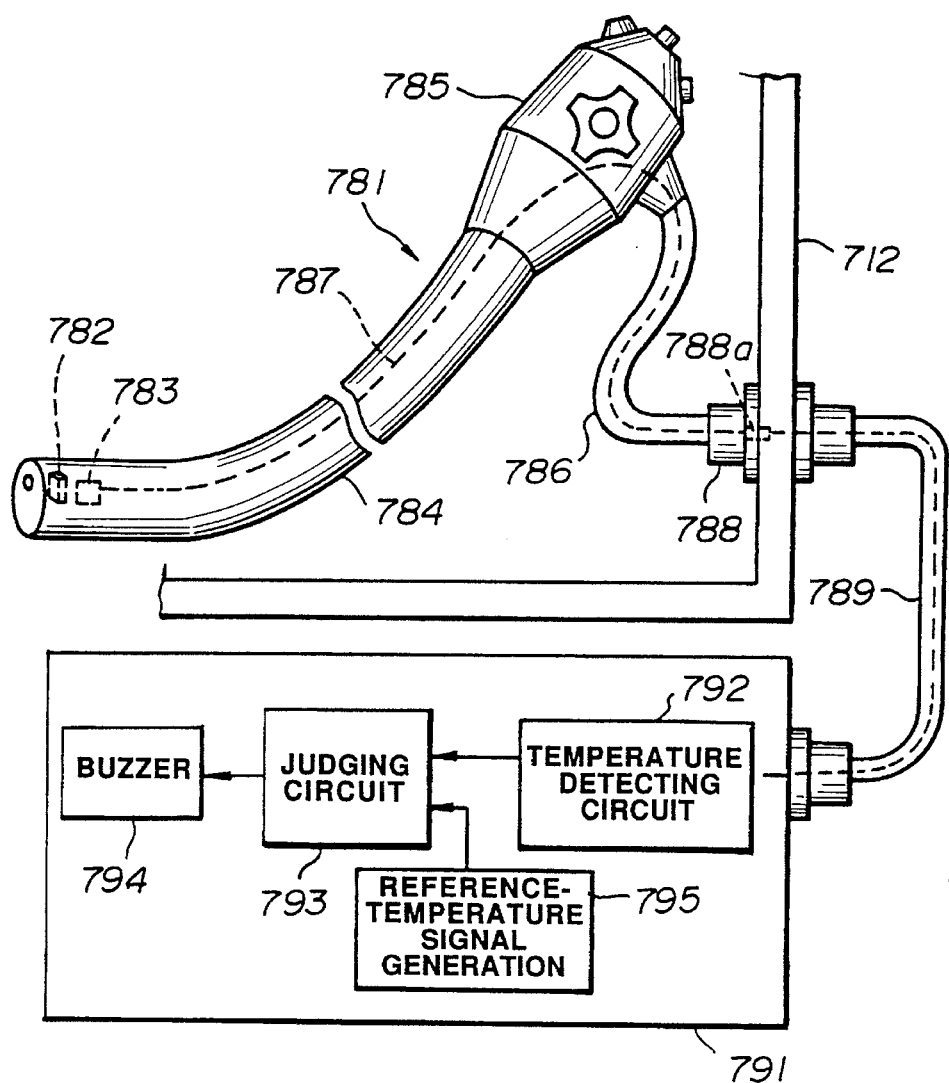
FIG. 57 is an arrangement view showing a portion of an autoclave unit in accordance with a seventh embodiment of the invention.

An autoclave unit according to a seventh embodiment is characterized in that when semiconductor components or parts, for example, reach a permitted low limit temperature which is low in resistance with respect to a temperature in a medical instrument processed in autoclave at the autoclave processing an abnormal detecting signal is generated to notify the user will be described with reference to FIG. 57.

In this embodiment, a CCD 782 forming image pickup means is built in an electronic scope 781 which is received within an autoclave unit body 712 of an autoclave unit 711 according to, for example, a fifth embodiment, and a temperature sensor 783 for detecting a temperature is built in a location adjacent to the CCD 782.

The temperature sensor 783 reaches a temperature detecting connector pin 788a of a connector 788 through an inserting section 784, an operating section 785, and a signal line 787 inserted in a universal cable 786. The temperature detecting connector pin 788a is capable of being connected to a connector receptor which is provided on a wall surface of the autoclave unit body 712. A connector is connected to the connector receptor from the outside. The cable 789 provided with the connector is connected to the temperature detecting circuit 792 within the abnormal detecting means 791.

Temperature information detected by the temperature detecting circuit 792 is connected to the buzzer 794 through a (temperature abnormality) judging circuit 793. In a case where temperature information detected during the autoclave processing becomes equal to or greater than a temperature set by the reference-temperature signal generating circuit 795, the buzzer 794 is set to ring to notify an operator that the temperature is approaching the maximum temperature permitted with respect to the CCD 782.

Figure 58:
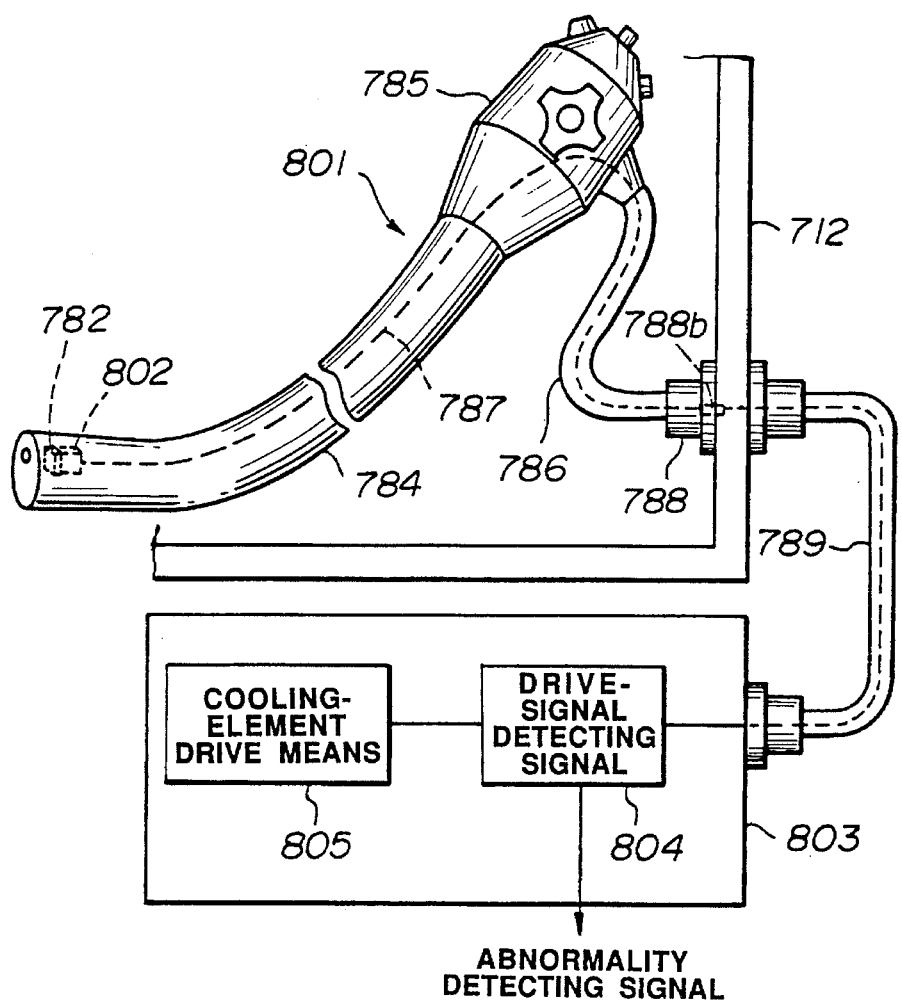
FIG. 58 is an arrangement view showing a portion of an autoclave unit in accordance with an eighth embodiment of the invention.

FIG. 58 shows a principal portion of the autoclave unit according to an eighth embodiment of the invention. In this embodiment, an electronic scope 801 in which autoclave processing is executed is arranged such that, in the electronic scope 781 illustrated in FIG. 57, a cooling element 802 (such as a Peltier element or the like, for example) for cooling the CCD 782 is built in place of the temperature sensor 783. The cooling element 802 reaches a cooling-element drive pin 788b of a connector 788 through a signal line 787.

The cooling-element drive pin 788b is connected to drive-signal (condition) detecting means 804 within the abnormality detecting means 803 through a cable 789. The drive-signal detecting means 804 is further connected to cooling-element drives means 805. The drive-signal condition detecting means 804 detects voltage and current of the drive signal outputted to the cooling element 802 from the cooling-element drive means 805, and an impedance and the like of the drive signal line 787, to detect abnormality of the drive signal for cooling the cooling element 802. In a case where abnormality is detected, an abnormality detecting signal is outputted.

Figure 59:
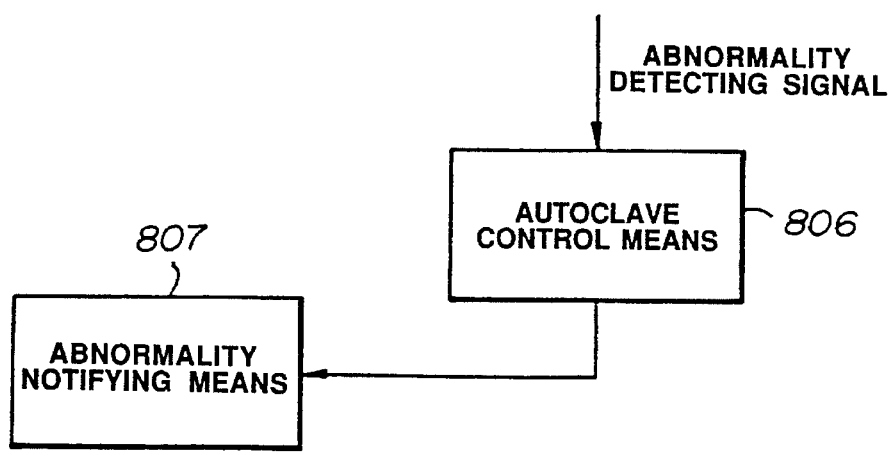
FIG. 59 is a view showing a portion of a treatment or processing system in a case where abnormality is detected.

As shown in FIG. 59, the abnormality detecting signal is inputted to the autoclave control means (a control portion 724 in the embodiment illustrated in FIG. 53) 806. When the signal is inputted to the autoclave control means 806, the autoclave control means 806 commands that abnormality notifying means 807 such as a buzzer, a display panel or the like is operated, to issue a warning of the abnormality by a buzzer, or to execute display of the abnormality by a display panel or the like. In a case where there is the warning, the autoclave processing, for example, should stop.

Figure 60:
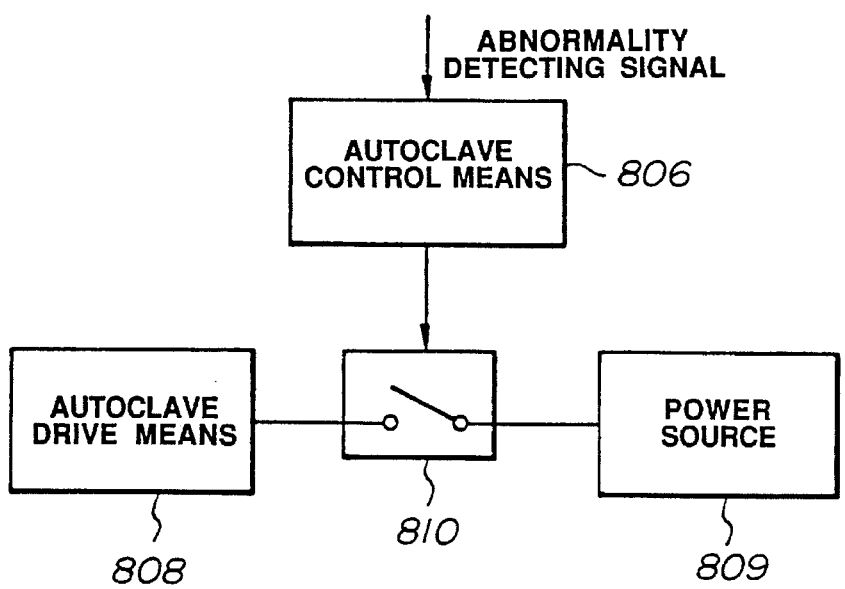
FIG. 60 is a view showing a portion of a processing system in a case where abnormality different from FIG. 59 is detected.

FIG. 60 shows a first modification of the informing means illustrated in FIG. 59. In the first modification, when an abnormality informing signal is inputted to the autoclave control means 806, the autoclave control means 806 automatically shuts down power supply from the power source 809 operating the autoclave drive means 808 by turning-off of a switch 810.

Figure 61:
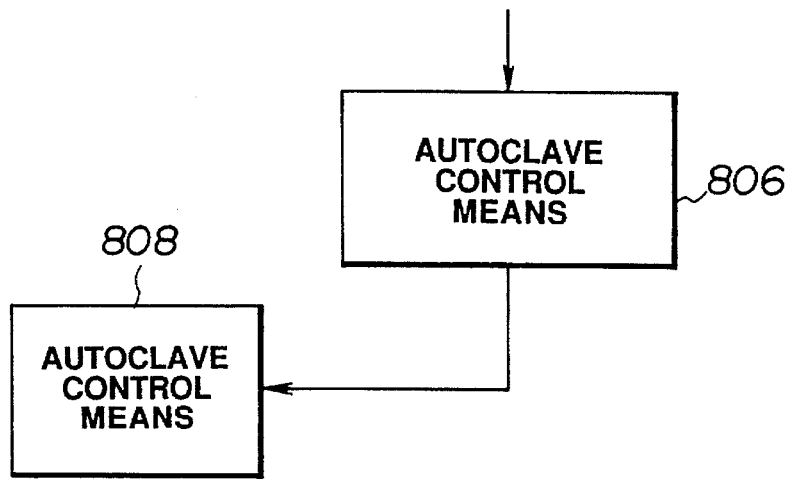
FIG. 61 is a view showing a portion of a processing system in a case where abnormality different from FIG. 60 is detected.

Further, in the second modification illustrated in FIG. 61, when the abnormality detecting signal is inputted to the autoclave control means 806, the autoclave control means 806 outputs a control signal of driving stoppage to the autoclave drive portion 808, to stop the autoclave processing. In this manner, it is possible to prevent the CCD 782 from being destroyed by an abnormal operational condition, to prevent a characteristic from being deteriorated, or the like.

An embodiment in which a drive signal line for driving the cooling means for cooling the image pickup element utilizes a part of the CCD driving signal line will next be described with reference to FIG. 62. An objective lens 823 is mounted on an observation window provided in a forward end surface of an inserting-section armored frame 822 which forms an inserting section 821 of the electronic scope 820 illustrated in FIG. 62. The CCD 824 has a photoelectric transfer surface which is arranged at a focus surface of the objective lens 823.

The CCD 824 is of a structure integrated with a hybrid substrate 825. A signal photoelectrically-transferred by the CCD 824 passes through the hybrid substrate 825, passes through a signal transmitting line 826 connected to the hybrid substrate 825, and is inputted to a video processor (not shown). The video processor transfers the output signal from the CCD 824 to a standard image signal.

A light guide 828 for transmitting an illuminating light is inserted in the inserting-section armored frame 822. The light guide 828 is connected to a proximal end of the inserting-section armored frame 822, and is inserted in the operating-section armored frame 830 forming the operating section 829, and a universal cable 831 which extends from the operating-section armored frame 830.

A connector 838 at the proximal end of the universal cable 831 is connected to a light-source unit (not shown), whereby an illuminating light from the light-source unit is transmitted and is outdone toward a forward subject further through the illuminating lens 832 from the forward end surface.

A pair of tubes 833 and 834 for forcibly cooling are received within the inserting-section armored frame 822 and the operating-section armored frame 822 and the operating-section armored frame 830 wide in width. The tubes 833 and 834 have respective forward-end openings respectively which are arranged adjacent to the CCD 824 and the hybrid substrate 825. An opening at the hand is connected to a cooler 835 which is received in the operating-section armored frame 830. Cooling air cooled by the cooler 835 passes through the tube 833 and is discharged from the forward-end opening in the cube 833 to be enabled to cool the CCD 824 and the hybrid substrate 825 which are arranged adjacent to the forward-end opening.

Air which has cooled the CCD 824 and the hybrid substrate 825 passes through the tube 834, and is returned to the cooler 835, and is again cooled and is capable of being supplied to a location adjacent to the forward end of the electronic scope 820. The cooler 835 is formed by a Peltier element.

The cooler 835 is connected to a power source line 826*a* in a signal transmitting line 826, through the voltage converter 836. The voltage converter 836 converts the power source voltage driving the CCD 824, to voltage driving the cooler 835, to drive the cooler 835.

The signal transmitting line 826 is inserted in a universal cable 831 extending from the operating-section armored frame 830, and is connected to a connector 838.

The electronic scope 820 comprises cooling means for cooling the CCD 824 and the hybrid substrate 825. Since a drive signal for electrically driving the cooling means is driven by the use of a power source line 826*a* of the CCD 824, it is not required to newly provide a cable in order to drive the cooler 835, but can use both for driving and cooling of the CCD 824. Further, the CCD 824 and the hybrid substrate 825 can be driven simultaneously.

In connection with the above, the arrangement may be such that, in a case where the electronic scope 820 is received in, for example, an autoclave unit body 712 illustrated in FIG. 53 to execute autoclave, the autoclave unit body 712 is provided with a connector receptor conducting with the power source line 826*a* in the connector 838, is connected to a power source (not shown) through a connector receptor, and a drive signal of direct current voltage equal to power source voltage of the CCD 824 is supplied from the power source to drive the cooler 835.

Figure 62:
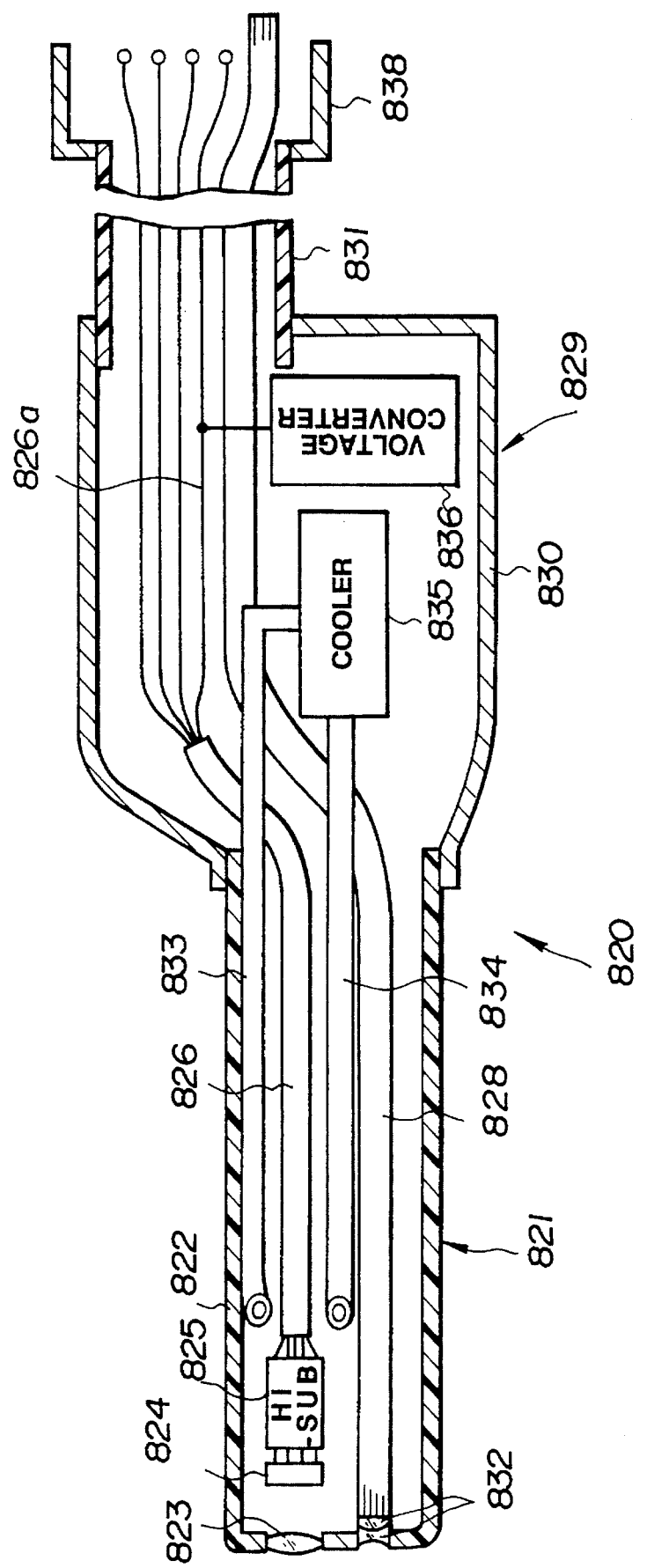
FIG. 62 is an arrangement view showing an electronic scope provided with means for cooling an image pickup element.

FIG. 63 shows a modification of FIG. 62. The modification is arranged such that, in an electronic scope 820 illustrated in FIG. 62, a power source line 826*a* connected to a drive power source terminal of the CCD 824 is set capable of being switched to a drive signal line (power source line) for driving a cooler 835 within an operating section 829, by a switch 841*a* which is provided within the operating section 829, switching of the switch 841*a* is executed by an output signal from the CCD drive-signal detecting circuit 843*a*, through a switching circuit 842*a*. A signal line 826' connected to a common contact of the switch 841*a* reaches a connector 838 through a universal cable 831.

The CCD drive-signal detecting circuit 843*a* is connected to a signal line 826*b* for transmitting a pulse-like drive signal such as a horizontal transfer pulse, a vertical transfer pulse and the like to the CCD. It is judged whether a drive signal for driving the CCD 824 is applied to the signal line 826*b*, to control selection (switching) of the switching circuit 842*a*.

On the other hand, the video processor 845 to which the connector 838 is connected is arranged such that the power source line conducting with the power source line 826' is connected to a common contact of a switch 841*b*. A CCD power source 847 and a cooling power source 848 are connected respectively to two contacts of the switch 841*b*. Furthermore, the CCD drive signal line other than the power source line 826' is connected to the CCD drive-signal generating circuit 849. When the CCD 824 is driven, the CCD drive signal is outputted from the CCD drive-signal generating circuit 849.

Moreover, a signal line through which a signal outputted from the CCD 824 is transmitted is connected to a signal processing circuit 850. A standard image signal is generated by the signal processing circuit 850, and is outputted to a monitor (not shown).

Further, the signal line 826*b* is connected to the CCD drive-signal detecting circuit 843*b*. The CCD drive-signal detecting circuit 843*b* judges that a drive signal is applied to the CCD 824 with reference to the signal line 826*b*, to output a signal controlling selection (switching) to a switching circuit 842*b*. The switching circuit 842*b* executes switching of the switch 841*b* in accordance with the signal. Further, an illuminating light from the light-source lamp 851 built in the video processor 845, for example, is supplied to an end portion adjacent to the connector 838 of the light guide 828.

Figure 64A:
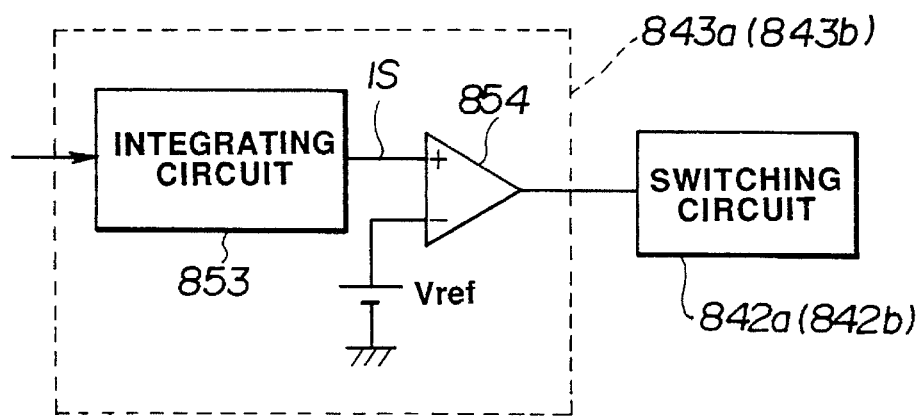
FIGS. 64a and 64b are block diagrams showing an arrangement of a CCD drive-signal detecting circuit.
Figure 64B:
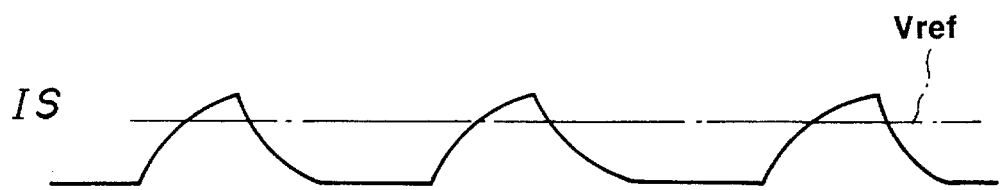

FIG. 64*a* shows an arrangement of a CCD drive-signal detecting circuit 843*a* or 843*b*. An input terminal is connected to an integrating circuit 853. An output signal from the integrating circuit 853 is connected to a non-converted input terminal of the comparator 854. A reference voltage value Vref is applied to a converted input terminal. The reference voltage value Vref is set to a value lower than a peak value of an integrating signal IS in which the CCD drive signal transmitted by the signal line 826*b* is integrated as illustrated in FIG. 64*b*, and is set to a value larger than zero.

An output from the comparator 854 controls switching of a switch 841*a* or 841*b* through a switching circuit 842*a* or 842*b* which is formed by a one-shot multi vibrator of again trigger type, for example. That is, in a case where image pickup is executed, a drive signal is outputted. In this case, accordingly, an integrating signal IS as shown in FIG. 64*b* is outputted. On the other hand, when image pickup is not executed, the drive signal is not outputted. Accordingly, the integrating signal IS becomes substantially zero.

Figure 65:
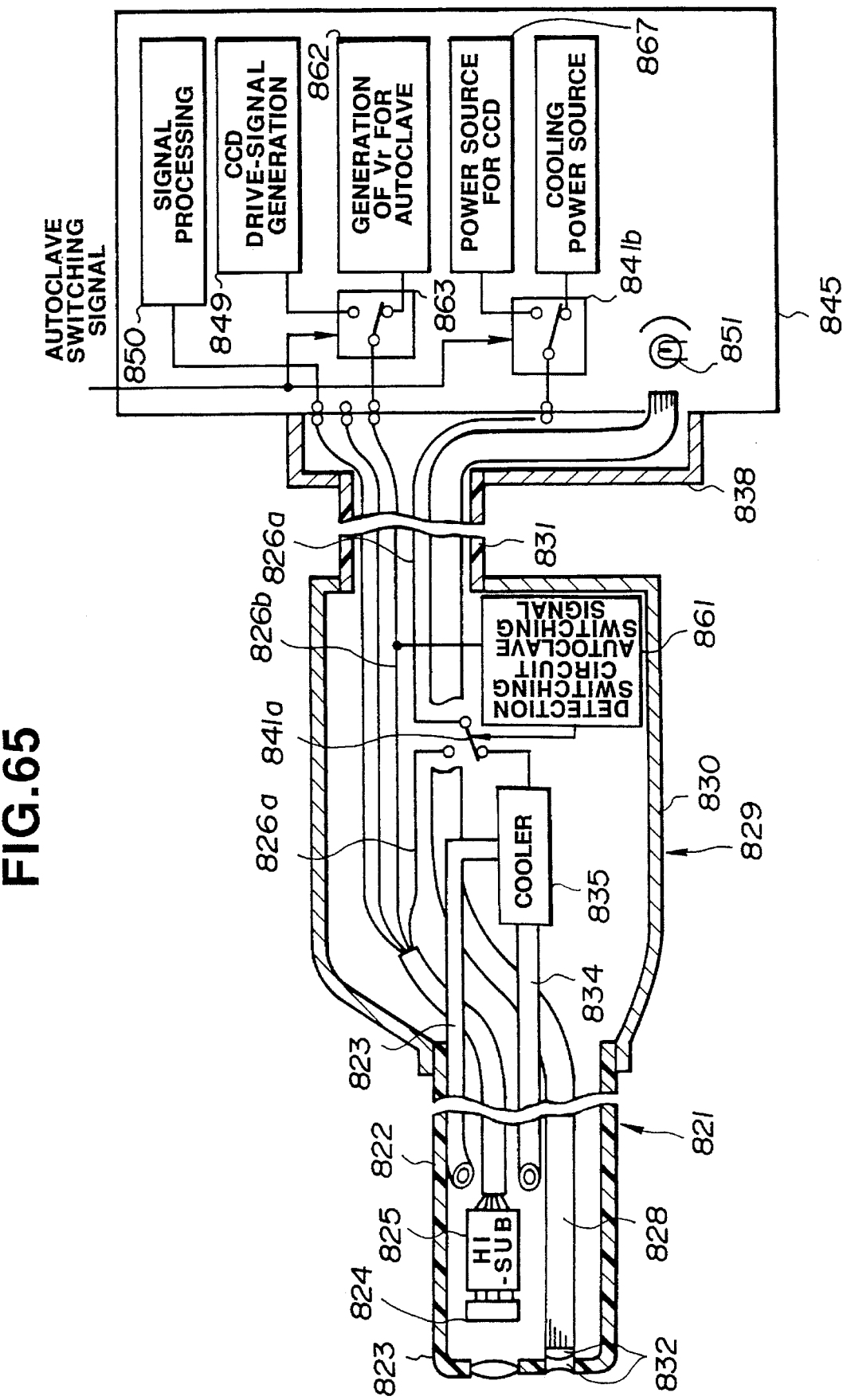
FIG. 65 is an arrangement view showing an electronic scope in accordance with a modification of FIG. 62.

FIG. 65 shows a modification of FIG. 63. In FIG. 63, the modification is arranged such that the switching circuit 841*a* within the operating section 829 and the CCD drive-signal detecting circuit 843a are replaced by a detecting switching circuit 861. Further, an autoclave reference-voltage generating circuit (an autoclave Vr generating circuit) 862, and a switch 863 are arranged adjacent to a video processor 845. The switches 863 and 841b are switched in interlocking with an autoclave switching signal (a signal of "H" being outputted at autoclave).

Figure 66A:
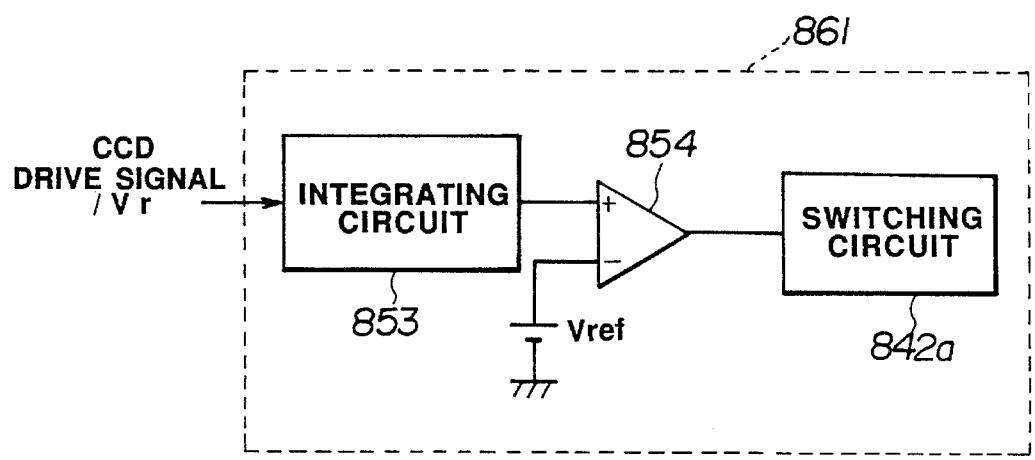
FIGS. 66a and 66b are block diagrams showing an arrangement of a detection switching circuit.
Figure 66B:
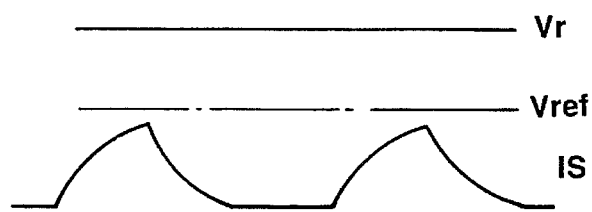

When the autoclave processing is executed, the switch 863 is arranged such that an autoclave reference-voltage generating circuit 862 is selected by an autoclave switching signal. The switch 841b is arranged such that a cooling power source 847 is selected. The autoclave reference-voltage generating circuit 862 generates an autoclave reference voltage Vr of a level larger than the reference voltage Vref as illustrated in FIG. 66b.

Moreover, the level of the reference voltage Vref is set to a value greater than an integrating signal IS in which the CCD drive signal is integrated. A detection switching circuit 861 executes switching of a switch 841a by an arrangement illustrated in FIG. 66a. The arrangement of the detection switching circuit 861 is similar to that illustrated in FIG. 65a, and the description thereof will be omitted. Further, other arrangements are similar to those illustrated in FIG. 63.

An autoclave switching signal executing switching in interlocking with the switch 863 and the switch 841b may automatically be issued at autoclave processing. Alternatively, a use may manually interlock the switch 863 and the switch 841b with each other.

In connection with the above, the electronic scope builds therein semiconductor components or parts such as a CCD and the like. Since electronic parts such as these semiconductor components or parts are low in heat resistance, there is a possibility that, even if protection for heat resistance is conducted, if the autoclave processing is repeatedly executed, deterioration in characteristic of the electronic components or parts occurs. There is a possibility that, by the deterioration in characteristic, an image obtained is deteriorated in quality, and malfunction may occur. In order to prevent such deterioration in characteristic, the arrangement may be such that a function of counting a number of the autoclave processing cycles is provided, and a warning is issued in a case where the number of autoclave processing cycles reaches a permissible number.

Figure 67:
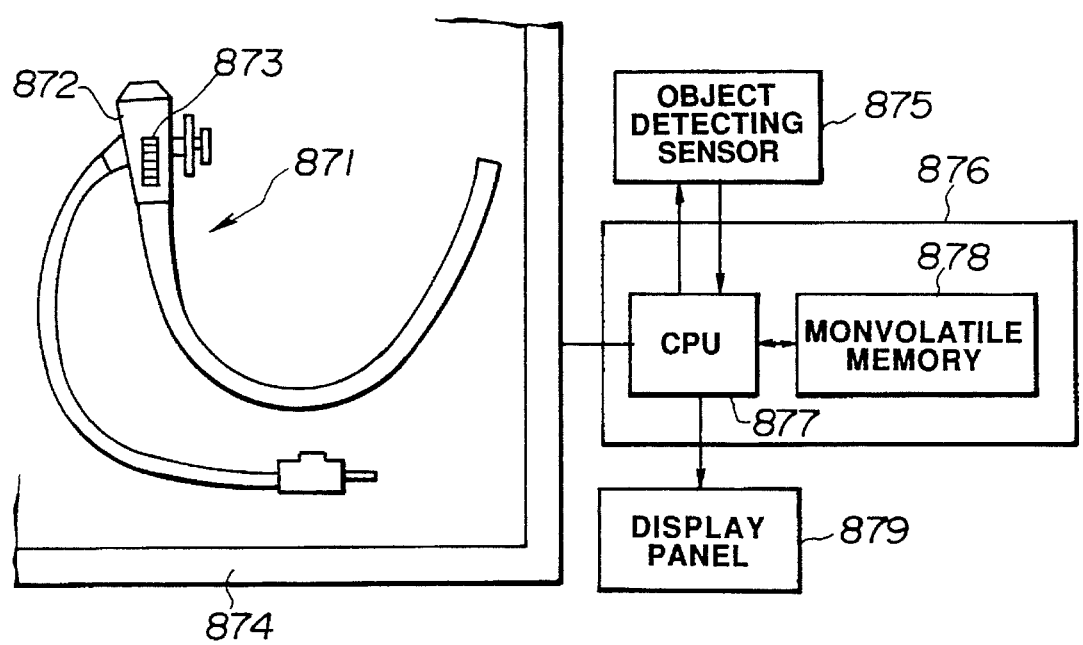
FIG. 67 is an arrangement view showing a portion of a unit provided with means for counting the number of times of autoclave processing.

In order to execute this, as shown in FIG. 67, an ID code for identification is provided in terms of bar codes 873 and color marks, in an operating section 872, for example, of an electronic scope 871 (or a fiber scope on which a TV camera is mounted). Before reception is executed within the autoclave unit body 874 in order to execute autoclave processing with respect to the electronic scope 871, the ID code is read out by a subject detecting sensor 875 such as a bar code reader or the like, and information representing the same is transmitted to the CPU 877 forming the autoclave control means 876.

The CPU 877 refers to non-volatile memory 878 and the like, and the electronic scope 871 of the ID code reads out how many times the autoclave processing cycle is executed prior to this time, and judges whether or not the number is less than a predetermined number. If it is judged that the number is less than the predetermined number, the CPU 877 executes display on the display panel 879 that the autoclave processing may be done. The electronic scope 871 is received in the autoclave unit body 874. When the autoclave processing starts, the CPU 877 renews such that the autoclave processing number of the non-volatile memory 878 increases by one. Further, the CPU 877 executes setting to autoclave processing temperature and autoclave time suitable for the electronic scope 871 of the ID code, by the ID code, to control operation of steam generating means and the like (not shown) forming an autoclave processing mechanism.

On the other hand, in a case where the electronic scope 871 of the ID code judges that the autoclave processing is executed only by a predetermined number prior to this time, the CPU 877 executes display that the autoclave processing is executed by a predetermined number on the display panel 879, to warn the use. In this connection, means for identifying an object such as the electronic scope 871 or the like may be executed by image processing or the like.

In connection with the above, other arrangements of the various embodiments described above may be covered by the scope of the appended claims.

What is claimed is:

1. An electronic type endoscope comprising:

an endoscope body having an elongated inserting section;

illuminating-light projection means for projecting an illuminating light from a distal end portion of said inserting section;

an objective optical system provided at the distal end portion of said inserting section for imaging a subject illuminated by said illuminating light;

an image pickup unit provided with an image pickup element for photoelectrically transferring an optical image based on said objective optical system, to generate an image pickup signal;

a pickup unit receiving body which receives and fully encloses said image pickup unit including a first detaching means located on a distal end of said pickup unit receiving body for detachably mounting said pickup unit receiving body on said endoscope body; and a second detaching means for detaching said image pickup unit from said pickup unit receiving body, said second detaching means being located on a proximal end of said pickup unit receiving body wherein said image pickup unit is detachable from said pickup unit receiving body via said second detaching means while said pickup unit receiving body is mounted on said endoscope body, wherein said second detaching means forms a portion of an outer surface of said proximal end of said pickup unit receiving body when attached to said pickup unit receiving body.

2. An electronic type endoscope according to claim 1, wherein said electronic type endoscope is an endoscope of TV camera outside mounted type having an image guide for transmitting an optical image due to said objective optical system toward an ocular lens, an ocular portion at which said ocular lens is arranged, and a TV camera having a mount mechanism detachable with respect to said ocular portion and provided with said image pickup unit.

3. An electronic type endoscope according to claim 2, wherein said TV camera has a TV camera head having said mount mechanism and a cable extending toward the outside from said TV camera head and provided with a connector at a proximal end of said TV camera.

4. An electronic type endoscope according to claim 3, wherein said image pickup unit has a connecting means for detachably connecting said image pickup unit to a proximal end of said cable.

5. An electronic type endoscope according to claim 2, wherein said endoscope body is an optical endoscope.

6. An electronic type endoscope according to claim 2, wherein said pickup unit receiving body has said mount mechanism, and said pickup unit receiving body receives said image pickup unit within a housing which is opened and closed by a closure mechanism.

7. An electronic type endoscope according to claim 2, wherein said endoscope body is formed by an optical endoscope and an optical adaptor having said mount mechanism and an image pickup lens.

8. An electronic type endoscope according to claim 7, wherein said pickup unit receiving body is detachable with respect to said optical adaptor by said first detaching means.

9. An electronic type endoscope according to claim 7, wherein said image pickup unit is detachable with respect to said optical adaptor by said second detaching means.

10. An electronic type endoscope according to claim 1, wherein said inserting section of said endoscope body is rigid.

11. An electronic type endoscope according to claim 1, wherein said inserting section of said endoscope body is flexible.

12. An electronic type endoscope according to claim 1, wherein said endoscope body and said pickup unit receiving body are formed of a material having heat resistance higher than a temperature at which at least said image pickup element is deteriorated.

13. An electronic type endoscope according to claim 1, wherein said image pickup unit has a peripheral circuit for executing signal processing with respect to said image pickup element.

14. An electronic type endoscope according to claim 1, wherein said image pickup unit has a connecting means for detachably connecting said image pickup unit to a signal line.

15. An electronic type endoscope according to claim 1, wherein said endoscope body is constructed of a material which is capable of withstanding high temperature produced by an autoclave steam during thermal sterilization processing.

16. An electronic type endoscope according to claim 15, wherein said endoscope body is capable of withstanding said autoclave thermal sterilization processing by steam having pressure equal to or greater than 1 atmosphere.

* * * * *